(12) United States Patent
Barnham et al.

(10) Patent No.: US 9,302,993 B2
(45) Date of Patent: *Apr. 5, 2016

(54) 8-HYDROXY QUINOLINE DERIVATIVES

(71) Applicant: PRANA BIOTECHNOLOGY LIMITED, Parkville, Victoria (AU)

(72) Inventors: Kevin Jeffrey Barnham, Coburg (AU); Elisabeth Colette Louise Gautier, Bentleigh (AU); Gaik Beng Kok, North Carlton (AU); Guy Krippner, Glen Waverley (AU)

(73) Assignee: PRANA BIOTECHNOLOGY LIMITED, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/510,756

(22) Filed: Oct. 9, 2014

(65) Prior Publication Data

US 2015/0025108 A1 Jan. 22, 2015

Related U.S. Application Data

(63) Continuation of application No. 11/901,941, filed on Sep. 19, 2007, which is a continuation-in-part of application No. 10/521,902, filed as application No. PCT/AU03/00914 on Jul. 16, 2003, now Pat. No. 7,619,091.

(30) Foreign Application Priority Data

Jul. 16, 2002 (AU) .................................. 2002950217

(51) Int. Cl.
| | |
|---|---|
| *A61K 31/47* | (2006.01) |
| *C07D 215/00* | (2006.01) |
| *C07D 215/24* | (2006.01) |
| *C07D 215/26* | (2006.01) |
| *C07D 215/28* | (2006.01) |
| *C07D 215/38* | (2006.01) |
| *A61K 31/4709* | (2006.01) |
| *C07D 215/48* | (2006.01) |
| *A61K 45/06* | (2006.01) |
| *C07D 401/04* | (2006.01) |
| *C07D 401/12* | (2006.01) |
| *C07D 401/14* | (2006.01) |
| *C07D 409/04* | (2006.01) |
| *C07D 417/12* | (2006.01) |
| *C07D 417/14* | (2006.01) |
| *A61K 31/4725* | (2006.01) |

(52) U.S. Cl.
CPC .............. *C07D 215/48* (2013.01); *A61K 31/47* (2013.01); *A61K 31/4709* (2013.01); *A61K 31/4725* (2013.01); *A61K 45/06* (2013.01); *C07D 215/00* (2013.01); *C07D 215/24* (2013.01); *C07D 215/26* (2013.01); *C07D 215/28* (2013.01); *C07D 215/38* (2013.01); *C07D 401/04* (2013.01); *C07D 401/12* (2013.01); *C07D 401/14* (2013.01); *C07D 409/04* (2013.01); *C07D 417/12* (2013.01); *C07D 417/14* (2013.01)

(58) Field of Classification Search
CPC . A61K 31/47; A61K 31/4709; C07D 215/26; C07D 215/28; C07D 215/00; C07D 215/38; C07D 215/24

See application file for complete search history.

(56) References Cited

U.S. PATENT DOCUMENTS

| | | | |
|---|---|---|---|
| 3,682,927 | A | 8/1972 | Carissimi et al. |
| 5,980,914 | A | 11/1999 | Gerolymatos |
| 6,379,666 | B1 | 4/2002 | Tobinick |
| 7,619,091 | B2 | 11/2009 | Barnham et al. |
| 2008/0161353 | A1* | 7/2008 | Barnham et al. ............... 514/314 |

FOREIGN PATENT DOCUMENTS

| | | |
|---|---|---|
| DE | 3932338 A1 | 11/1991 |
| EP | 1074257 A1 | 2/2001 |
| RU | 2170730 | 12/1994 |
| RU | 2142454 | 10/1999 |
| WO | 9429274 | 12/1994 |
| WO | 9744036 | 11/1997 |
| WO | 9806403 | 2/1998 |
| WO | 9909981 | 3/1999 |
| WO | 9945907 | 9/1999 |

(Continued)

OTHER PUBLICATIONS

Emilien, et al. Arch Neurol. vol. 57, Apr. 2000, pp. 454-459.

(Continued)

*Primary Examiner* — Kara R McMillian
(74) *Attorney, Agent, or Firm* — Scully Scott Murphy and Presser; Frank Digiglio

(57) ABSTRACT

The present invention describes a method for the treatment of a neurological condition in a subject which comprises administering to a subject in need thereof a therapeutically effect amount of a compound of the formula

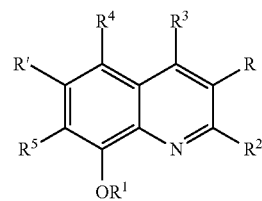

or pharmaceutically acceptable salts, hydrates, or solvates thereof.

6 Claims, 26 Drawing Sheets

(56) References Cited

FOREIGN PATENT DOCUMENTS

| WO | 0023421 |  | 4/2000 |
|---|---|---|---|
| WO | 0058344 |  | 5/2000 |
| WO | 0224701 | A2 | 3/2002 |
| WO | 0224702 | A1 | 3/2002 |
| WO | 02067939 | A1 | 9/2002 |
| WO | 03004016 | A1 | 1/2003 |
| WO | 03004483 | A1 | 1/2003 |
| WO | 03005038 | A1 | 1/2003 |
| WO | 03010146 | A1 | 2/2003 |
| WO | 03040096 | A2 | 5/2003 |
| WO | 03047572 | A1 | 6/2003 |

OTHER PUBLICATIONS

Shekunov et al. Journal of Crystal Growth, vol. 211, pp. 122-136, 2000.

Vippagunta et al. 2001, "Crystalline Solids", Advanced Drug Delivery Reviews, vol. 48, pp. 3-26.

Cherny, et al., "Treatment with a Copper-Zinc Chelator Markedly and Rapidly Inhibits β-Amyloid Accumulation in Alzheimer's Disease Transgernic Mice" Neuron; 30, 665-676 (2001).

Cuajungco, et al., "Metal Chelation as a Potential Therapy for Alzheimer's Disease", Ann N.Y. Acad. Sci., 920: 292-304 (2000).

nternational Preliminary Examination Report on Patentability issued in the corresponding International Application PCT/AU2003/00914.

Carrissimi, et al, "Derivatives of 5.7-Dichloro-8-Hydroxyquinoline with Antibacterial and Antifungal Activity", II Farmaco-Ed. Sc.; 24:5, 478-499 with English translation.

Tjaelve, "The Aetiology of Smon May Involve an Interaction Between Clioquinoland Environmental Metals", Medical Hypotheses; 15: 293-299 (1984).

* cited by examiner

A: R6/2 PBT2 treated
B: R6/2 SSV treated
wt: wildtype
m: male R6/2

8-HYDROXY QUINOLINE DERIVATIVES

CROSS REFERENCE TO RELATED APPLICATIONS

The present application is a continuation of U.S. patent application Ser. No. 11/901,941, filed on Sep. 19, 2007, which is a continuation in-part of application U.S. Ser. No. 10/521,902, filed on Aug. 10, 2005, now U.S. Pat. No. 7,619,901, granted on Nov. 17, 2009, the contents of which are incorporated by reference, which is a '371 of PCT Application PCT/AU03/00914, filed on Jul. 16, 2003, which claims the benefit of priority of Australian Patent Application No. 2002950217, filed on Jul. 16, 2002.

FIELD OF THE INVENTION

The present invention relates to 8-hydroxy quinoline derivatives, processes for their preparation and their use as pharmaceutical or veterinary agents, in particular for the treatment of neurological conditions, more specifically neurodegenerative conditions such as Alzheimer's disease, Huntington's disease and the like.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

The life span is thought to be biologically fixed for each species, and the length of the human life span is uncertain, but may be up to 120 years. Since life expectancy has risen significantly in this century, the elderly are an increasing segment of our population, and their health care needs will continue to grow for decades.

Although normal aging is characterized by modest reductions in the mass and volume of the human brain, which may be due to the atrophy and/or death of brain cells, these changes are far more profound in the brains of patients who succumb to a neurodegenerative condition. Most of these conditions are sporadic and of unknown cause, but hundreds of different mutations in many genes have been shown to cause familial (inherited) variants of several neurodegenerative conditions. Many of the dozen or more genes that harbour these mutations were discovered in the quest to determine the genetic basis of neurodegenerative conditions just in the last ten years. Neurodegenerative conditions evolve gradually after a long period of normal brain function, due to progressive degeneration (i.e., nerve cell dysfunction and death) of specific brain regions. Since symptomatic expression of disease occurs when nerve cell loss exceeds a "threshold" for the continuing function (e.g., memory, movement) performed by the affected brain region, the actual onset of brain degeneration may precede clinical expression by many years.

Intellectual and higher integrative cognitive faculties become progressively impaired and interfere with activities of daily living in neurological conditions resulting in dementia. The precise prevalence of dementia in the elderly population is unknown, but may be 15% of people over 65 years old with 5% severely and 10% mildly to moderately demented. The prevalence of severe dementia increases from 1% at 65 years to 45% at 85 years. There are many causes of dementia, but Alzheimer's Disease (AD) accounts for 50% of demented patients over 65 years of age.

AD is a primary degenerative disease of the brain. It is characterized by progressive decline of cognitive functions such as memory, thinking, comprehension, calculation, language, learning capacity and judgement. Dementia is diagnosed when the declines are sufficient to impair personal activities of daily living. AD shows an insidious onset with slow deterioration. This disease needs to be clearly differentiated from age-related normal decline of cognitive functions. The normal decline is much less, much more gradual and leads to milder disabilities. The onset of AD is usually after 65 years of age, although earlier onset is not uncommon. As age advances, the incidence increases rapidly (it roughly doubles every 5 years). This has obvious implications for the total number of individuals living with this disorder as life expectancy increases in the population.

The aetiology of AD is unclear. There is considerable evidence of a heritable predisposition for some forms of AD (reviewed in St George-Hyslop, 2000), and the expression of certain isoforms of ApoE has also been linked to a higher risk of AD (Corder et al, 1993; Czech et al 1994). The toxic accumulation of aluminium has been suggested as a causative agent in AD, although this hypothesis has now been superseded. The brains of AD patients display abnormal deposits which include (3-amyloid protein (Aβ).

Aβ is known to be present in the brains of individuals with certain neurodegenerative diseases, but it is not known whether it is symptomatic of an underlying disease process, or is actually involved in the aetiology of the disease. For example, some authors believe that the Aβ deposits may be indicative of a normal brain defence mechanism, wherein the brain attempts to sequester the Aβ; such deposits can be present in the brains of normal individuals. There is a mutation of tau protein wherein neurofibrillary tangles, but no amyloid plaques are present in the brain; this condition is known as tauopathy.

One proposed approach to AD therapy is to inhibit production of Aβ in the brain. Proteolytic cleavage of APP by BACE1 and γ-secretase generates the full-length Aβ, which is then released from cells (Nunan and Small, 2000). Alternatively, a number of studies have shown that cholesterol can influence Aβ release (Simons et al., 1998; Hartmann, 2001; Fassbender et al., 2001; Frears et al., 1999; Friedhoff et al., 2001). However, there is some disagreement in the art as to the value of lowering cholesterol levels, and some workers consider that cholesterol is actually beneficial. For example, Ji et al, (2002) have suggested that the binding of Aβ to cholesterol might prevent Aβ toxicity by inhibiting its oligomerization.

In an alternative approach, it has been proposed that by unravelling the proteolytic processing of the amyloid precursor protein (APP), which generates the Aβ amyloid monomer, a number of possible therapeutic targets may be possible (Shearman et al., 2000; Sinha et al., 1999);], and this approach is in an early stage of clinical development. Attempts to promote the clearance of Aβ from the brain through immunization with Aβ, while efficacious in a transgenic mouse model for AD (Schenk et al 1999), have been found to have significant adverse effects (Brower, 2002).

It has also been suggested that deposition of amyloid-like fibrils may also be important in other neurodegenerative diseases. These include Parkinson's disease, dementia with Lewy body formation, multiple system atrophy, Hallerboden-Spatz disease, and diffuse Lewy body disease.

One of the competing theories of the aetiology of AD is that the causative step(s) lies within the pathway of the intracerebral biogenesis and accumulation of the Aβ amyloid protein (see recent reviews by Selkoe, 2001; Beyreuther et al., 2001; Bush, 2001). However, to date no drugs or agents which target this pathway have been demonstrated to have a lasting effect on modifying the clinical expression of the disease or in preventing or ameliorating the decline in cognitive function associated with neurodegenerative disorders, including Alzheimer's disease.

A further hypothesis is that AD is caused by the toxic accumulation of Aβ amyloid, due in part to excess binding of copper and zinc, metal ions which are abundant in the regions most affected. Moreover, it has been suggested that when $Zn^{2+}$ and $Cu^{2+}$ ions interact with Aβ, aggregation of Aβ into fibrils and plaques occurs (Atwood et al., 1998; confirmed by recent data from animals deficient in synaptic $Zn^{2+}$ (Lee et al., 2002). It has also been suggested that redox-active $Cu^{2+}$-Aβ interactions can generate $H_2O_2$ from $O_2$ (Huang et al., 1999). Both $Cu^{2+}$ and $Zn^{2+}$ have been shown to affect Aβ-lipid membrane interactions (Curtain et al., 2001). The brain is an organ that concentrates metal ions and recent evidence suggests that a breakdown in metal homeostasis plays a critical role in a variety of age-related neurodegenerative diseases. Common features of these diseases include the deposition of misfolded protein (each disease has its own specific amyloid protein) and substantial cellular damage as a result of oxidative stress. Indeed data is now rapidly accumulating that met-allochemical reactions could emerge as the common denominator underlying amyloidogenic neurological disorders such as Alzheimer's disease, amylotrophic lateral sclerosis (ALS), prion diseases—including Creutzfeldt-Jakob Disease (CJD), transmissible spongioform encephalopathies (TSE), cataracts, mitochondrial disorders, Parkinson's disease and Huntington's disease. In these instances, the pathological aggregation of a specific protein is promoted by abnormal redox activity in a physiological environment typefied by the presence of transition metals and available reducing agents. [Bush, 2000 (Curr Opin Chem Biol. 2000 April; 4(2):184-91)].

Accordingly the present invention provides a means of treating neurological conditions, including those characterised by the abnormal interaction between proteins and metals.

A method of treatment of AD using iodochlorohydroxyquinoline an antibiotic [also known as clioquinol (CQ)], is disclosed and claimed in U.S. Pat. Nos. 5,994,323 and 6,001,852 by P. N. Geromylatos S. A. and in U.S. patent application Ser. No. 09/972,913 by Bush et al. CQ was withdrawn as an antibiotic in 1970, because of its association with an uncommon neurological syndrome, subacute myelo-optic neuropathy (SMON), which was observed only in Japan in the 1960s, in patients thought to have received the drug over long periods and probably at doses higher than those recommended at the time (Shiraki, 1975). However, recent evidence suggests that SMON was caused by an overuse-related vitamin B12 deficiency in an exceptionally vulnerable population, and therefore could be rehabilitated for study in a clinical setting (Yassin et al., 2000; Bush and Masters, 2001).

However, no in vivo results in animal models or in humans are provided in the Geromylatos and Bush patents. U.S. Pat. No. 5,994,323 discloses a composition comprising CQ and Vitamin B12, and its use for the treatment of "diseases or disorders responsive to CQ administration while inhibiting detrimental side effects" of CQ. These diseases include AD. U.S. Pat. No. 6,001,852 discloses a method of treatment of AD using CQ, preferably together with Vitamin B12. Both U.S. Pat. Nos. 5,994,323 and 6,001,852 suggest a dosage of 10-750 mg per day; U.S. Pat. No. 5,994,323 recommends that if treatment is over a long period, CQ should be given intermittently, for up to 3 weeks at a time followed by a "wash-out" period of 1-4 weeks.

In U.S. application Ser. No. 09/972,913, CQ is exclusively referred to in terms of its ability to disaggregate Aβ deposits. No other mechanism of neurotoxicity is discussed. PCT/US99/05291 assigned to General Hospital Corporation discloses the use of CQ in combination with specific copper and zinc chelators to promote dissolution of amyloid plaques and inhibition of amyloid plaque formation and/or the production of ROS by Aβ.

U.S. Pat. No. 6,001,852 also suggests that a composition comprising CQ and Vitamin B12 could be used in the treatment of Parkinson's disease; however, in this context it is suggested that CQ acts primarily via clearing iron from the substantia nigra.

The efficacy of CQ in the treatment of AD rests upon its ability to enter the CNS and then sequester the transition metals Cu, Zn and Fe from various Aβ entities, thereby reducing Aβ toxicity and liberating it for clearance. The effectiveness of CQ is restricted by its poor aqueous solubility, which limits its oral bioavailability. CQ is also known to undergo considerable conjugative metabolism and has a history of toxicity, as discussed above. The fact that CQ is a bidentate metal ligand makes necessary the commitment of at least two molecules for every metal ion captured.

We have now developed 8-hydroxyquinoline derivatives which are more efficacious than CQ through the collective optimization of one or more of the following properties:
(a) metal chelation (as herein defined);
(b) aqueous solubility;
(c) reduced cell toxicity;
(d) amyloid dispersion properties;
(e) membrane permeability appropriate for CNS penetration; and
(f) metabolic stability.

These derivatives include examples of therapeutics which are concentrated in the CNS through active transport, contain antioxidant activity in addition to their metal chelation properties which in some cases leads to enhanced metal chelation properties and demonstrate a prodrug strategy which masks the 8-hydroxy moiety to favour CNS penetration and make use of the known esterase activity which resides on the inner surface of the blood brain barrier (BBB).

SUMMARY OF THE INVENTION

According to the present invention there is provided a method for the treatment, amelioration and/or prophylaxis of a neurological condition which comprises the administration of an effective amount of a compound of formula I:

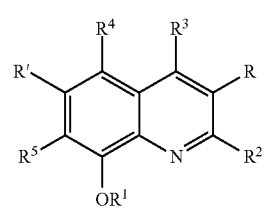

wherein

R¹ is H, optionally substituted alkyl, optionally substituted alkenyl, optionally substituted acyl, optionally substituted aryl, optionally substituted heterocyclyl, an antioxidant or a targeting moiety;

R² is H; optionally substituted alkyl; optionally substituted alkenyl; optionally substituted aryl; optionally substituted heterocyclyl; optionally substituted alkoxy; an antioxidant; a targeting moiety; COR⁶ or CSR⁶ wherein R⁶ is H, optionally substituted alkyl, optionally substituted alkenyl, hydroxy, optionally substituted aryl, optionally substituted heterocyclyl, an antioxidant, a targeting moiety, OR⁷, SR⁷ or NR⁷R⁸ wherein R⁷ and R⁸ are either the same or different and selected from H, optionally substituted alkyl, optionally substituted alkenyl, optionally substituted aryl and optionally substituted heterocyclyl; CN; (CH₂)ₙNR⁹R¹⁰, HCNOR⁹ or HCNNR⁹R¹⁰, wherein R⁹ and R¹⁰ are either the same or different and selected from H, optionally substituted alkyl, optionally substituted alkenyl, optionally substituted aryl and optionally substituted heterocyclyl and n is 1 to 4; OR¹¹SR¹¹ or NR¹¹R¹²; wherein R¹¹ and R¹² are either the same or different and selected from H, optionally substituted alkyl, optionally substituted alkenyl, optionally substituted aryl and optionally substituted heterocyclyl or together form optionally substituted heterocyclyl; or SO₂NR¹³R¹⁴ wherein R¹³ and R¹⁴ are either the same or different and selected from H, optionally substituted alkyl, optionally substituted alkenyl, optionally substituted aryl or optionally substituted heterocyclyl; and R³, R⁴, R⁵, R and R' are either the same or different and selected from H, optionally substituted alkyl, optionally substituted alkenyl, optionally substituted alkoxy, optionally substituted acyl, hydroxy, optionally substituted amino, optionally substituted thio, optionally substituted sulphonyl, optionally substituted sulphinyl, optionally substituted sulphonylamino, halo, SO₃H, amine, CN, CF₃, optionally substituted aryl, optionally substituted heterocyclyl, an antioxidant and a targeting moiety, salts, hydrates, solvates, derivatives, pro-drugs, tautomers and/or isomers thereof with the provisos that:

(a) when R¹ to R³, R and R' are H, then R⁴ is not Cl or I and R⁵ is not I;

(b) when R¹ to R³, R, R' and R⁵ are H, then R⁴ is not CHO, CHOHCCl₃,

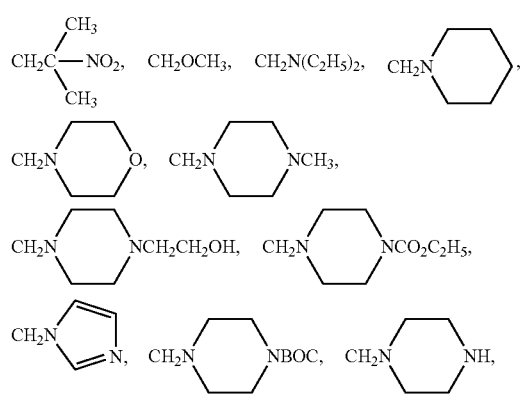

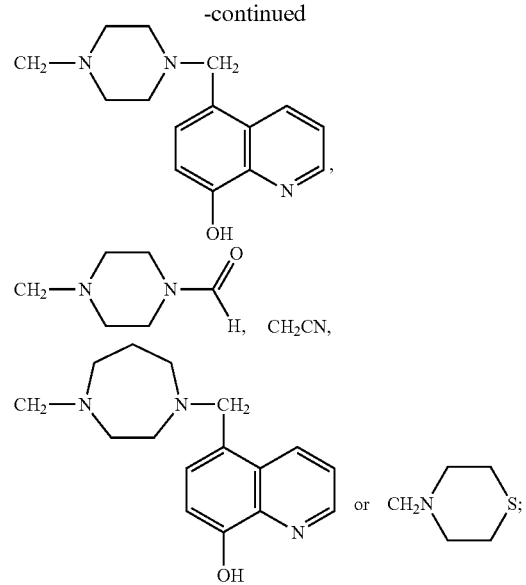

(c) when R¹, R⁵, R' and R are H, R² is CO₂H and R³ is OH, then R⁴ is not bromo, methyl, phenyl, hydroxymethyl or trifluoromethyl;

(d) when R¹, R⁴, R⁵ and R are H, R² is CO₂H and R³ is OH, then R' is not bromo, iodo, methyl, phenyl, propyl, phenethyl, heptyl, benzylaminomethyl, 3-aminopropyl, 3-hydroxypropyl, 4-methoxyphenyl, 3-methylphenyl, 4-chlorophenyl, 3,4-dichlorophenyl, pyridin-3-yl, furo-2-yl, 4-chlorophenyl, 3,4-dichlorophenyl, 2-chlorophenyl, 3-chlorophenyl, 2-chlorophenyl, 3-chlorophenyl, 2-methoxyphenyl or piperidin-2-yl;

(e) when R¹, R⁴, R and R' are H, R² is CO₂H and R³ is OH, then R⁵ is not phenyl, 3-hydroxypropyl, phenethyl, 3-aminoprop-1-yl or hex-1-yl;

(f) when R¹, R⁴, R' and R⁵ are H, R² is CO₂H and R³ is OH, then R is not N-morpholinomethyl, bromo or phenyl;

(g) when R¹, R and R' are H, R² is CO₂H and R³ is OH, then R⁴ and R⁵ are not chloro;

(h) when R¹, R⁴ and R' are H, R² is CO₂H and R³ is OH, then R and R⁵ are not bromo;

(i) when R¹, R, R' and R⁵ are H, R² is CO₂Me and R³ is OH, then R⁴ is not hydroxymethyl, phenyl or bromo;

(j) when R¹, R, R⁴ and R⁵ are H, R² is CO₂Me and R³ is OH, then R' is not 4-methoxyphenyl, 3-methylphenyl, pyridin-3-yl, benzyl, bromo, 4-chlorophenyl, 3,4-dichlorophenyl, 3-hydroxypropyl or 3-tert-butoxycarbonylaminopropyl;

(k) when R¹, R, R⁴ and R' are H, R² is CO₂Me and R³ is OH, then R⁵ is not phenyl or 3-tert-butoxycarbonylaminoprop-1-yl;

(l) when R¹, R, R⁴, R' and R⁵ are H and R² is CO₂Me, then R³ is not toluene-4-sulphonylamino, piperazin-1-yl, morpholin-1-yl, piperidin-1-yl, 4-methylpiperazin-1-yl, 3-benzoylaminoprop-1-yl, phenethyl, 3-tert-butoxycarbonylaminopropyl, 3-hydroxypropyl, amino or hex-1-yl;

(m) when R¹, R⁴, R' and R⁵ are H, R² is CO₂Na and R³ is OH, then R is not phenyl;

(n) when R¹, R, R⁴, R' and R⁵ are H and R² is CO₂H, then R³ is not phenyl, 4-chlorophenyl, phenethyl, 3-hydroxypropyl, amino, morpholin-1-yl, piperidin-1-yl, 4-methylpiperazin-1-yl, toluene-4-sulphonylamino, 3-benzoylaminoprop-1-yl, aminoprop-1-ynyl, hex-1-yl, 5-hydroxypent-1-yl, piperazin-1-yl or 2-(1-piperazinyl)pyrimidinyl;

(o) when $R^1$, R' and R are H, $R^2$ is $CO_2Me$ and $R^3$ is OH, then $R^4$ and $R^5$ are not chloro;

(p) when $R^1$, $R^4$, R' and $R^5$ are H, $R^2$ is $CO_2Me$ and $R^3$ is OH, then R is not bromo;

(q) when $R^1$, R' and $R^4$ are H, $R^2$ is $CO_2Me$ and $R^3$ is OH, then R and $R^5$ are not bromo;

(r) when $R^1$, R, $R^3$, R' and $R^5$ are H and $R^2$ is $CO_2H$, then $R^4$ is not phenyl, 4-chlorophenyl or phenylethyl;

(s) when $R^1$, $R^5$, R', $R^4$, $R^3$ and R are H, then $R^2$ is not 2H-tetrazol-1-yl;

(t) when $R^1$, $R^5$, $R^4$ and R are H, $R^2$ is $CO_2H$ and $R^3$ is OH, then R' is not 3,5-dichlorophenyl or 4-fluorophenyl; and (u) at least one of $R^1$ to $R^5$, R and R' is other than H, to a subject in need thereof.

Further according to the present invention there is provided use of the compound of formula I in the manufacture of a medicament for the treatment, amelioration and/or prophylaxis of a neurological condition.

The invention also provides use of the compound of formula I for the treatment, amelioration and/or prophylaxis of a neurological condition.

The invention further provides the compound of formula I for use in the treatment, amelioration and/or prophylaxis of a neurological condition.

The invention still further provides use of the compound of formula I as a pharmaceutical, preferably a neurotherapeutic or neuroprotective agent, more preferably an antiamyloidogenic agent. Preferably, the neurological condition is a neurodegenerative condition, more preferably neurodegenerative amyloidosis such as Alzheimer's disease, Huntington's disease, and the like.

Preferred compounds of formula I are as follows:

(i) Formula Ia

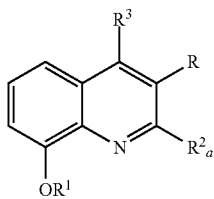

Ia wherein:

R, $R^1$ and $R^3$ are as defined in formula I above; and $R^2_a$ is H; optionally substituted $C_{1-6}$ alkyl; optionally substituted $C_{1-6}$ alkenyl; optionally substituted aryl; optionally substituted heterocyclyl; an antioxidant; a targeting moiety; $COR^6_a$ or $CSR^6_a$, wherein $R^6_a$ is H, optionally substituted $C_{1-6}$ alkyl, optionally substituted $C_{2-6}$ alkenyl, hydroxy, optionally substituted aryl, optionally substituted heterocyclyl or $OR^7_a$, $SR^7_a$ or $NR^7_a R^8_a$ wherein $R^7_a$ and $R^8_a$ are either the same or different and selected from H, optionally substituted $C_{1-6}$ alkyl, optionally substituted $C_{2-6}$ alkenyl, optionally substituted aryl and optionally substituted heterocyclyl; CN; $CH_2NR^9_a R^{10}_a$, $HCNOR^9_a$ or $HCNNR^9_a R^{10}_a$, wherein $R^9_a$ and $R^{10}_a$ are either the same or different and selected from H, optionally substituted $C_{1-6}$ alkyl, optionally substituted $C_{2-6}$ alkenyl, optionally substituted aryl or optionally substituted heterocyclyl; $OR^{11}_a$, $SR^{11}_a$ or $NR^{11}_a R^{12}_a$ wherein $R^{11}_a$ and $R^{12}_a$ are either the same or different and selected from H, optionally substituted $C_{1-6}$ alkyl, optionally substituted $C_{2-6}$ alkenyl, optionally substituted aryl and optionally substituted heterocyclyl or together form optionally substituted heterocyclyl; or $SO_2NR^{13}_a R^{14}_a$ wherein $R^{13}_a$ and $R^{14}_a$ are either the same or different and selected from H, optionally substituted $C_{1-6}$ alkyl, optionally substituted $C_{2-6}$ alkenyl, optionally substituted aryl and optionally substituted heterocyclyl.

Another embodiment of the present invention is a compound of the formula:

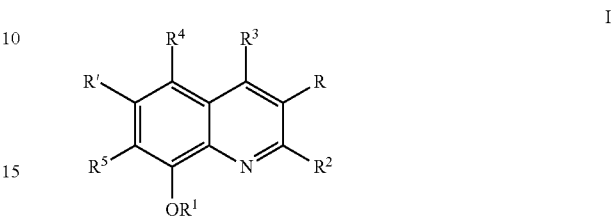

I or pharmaceutically acceptable salts, hydrates, or solvates and/or prodrugs thereof in which $R^1$ is H;

$R^2$ is optionally substituted $C_{1-6}$ alkyl; optionally substituted $C_{2-6}$ alkenyl; optionally substituted aryl; optionally substituted heterocyclyl; optionally substituted $C_{1-6}$ alkoxy; $COR^6$ or $CSR^6$, in which $R^6$ is H, optionally substituted $C_{1-6}$ alkyl, optionally substituted $C_{2-6}$ alkenyl, hydroxy, optionally substituted aryl, optionally substituted heterocyclyl, $OR^7$, $SR^7$ or $NR^7R^8$ in which $R^7$ and $R^8$ are either the same or different and selected from H, optionally substituted $C_{1-6}$ alkyl, optionally substituted $C_{2-6}$ alkenyl, optionally substituted aryl and optionally substituted heterocyclyl; CN; $(CH_2)_n NR^9R^{10}$, $HCNOR^9$ or $HCNNR^9R^{10}$ in which $R^9$ and $R^{10}$ are either the same or different and selected from H, optionally substituted $C_{1-6}$ alkyl, optionally substituted $C_{2-6}$ alkenyl, optionally substituted aryl and optionally substituted heterocyclyl and n is 1 to 4; $OR^{11}$, $SR^{11}$ or $NR^{11}R^{12}$ in which $R^{11}$ and $R^{12}$ are either the same or different and selected from H, optionally substituted $C_{1-6}$ alkyl, optionally substituted $C_{2-6}$ alkenyl, optionally substituted aryl and optionally substituted heterocyclyl or together form optionally substituted heterocyclyl; or $SO_2NR^{13}R^{14}$ in which $R^{13}$ and $R^{14}$ are either the same or different and selected from H, optionally substituted $C_{1-6}$ alkyl, optionally substituted $C_{2-6}$ alkenyl, optionally substituted aryl and optionally substituted heterocyclyl;

$R^3$, R and R' are either the same or different and selected from H, optionally substituted $C_{1-6}$ alkyl, optionally substituted $C_{2-6}$ alkenyl, optionally substituted $C_{1-6}$ alkoxy, optionally substituted acyl, hydroxy, optionally substituted amino, optionally substituted thio, optionally substituted sulphonyl, optionally substituted sulphinyl, optionally substituted sulphonylamino, halo, $SO_3H$, amine, CN, $CF_3$, optionally substituted aryl and optionally substituted heterocyclyl; and $R^4$ and $R^5$ are chloro, wherein the optional substituent is $C_{1-6}$ alkyl, $CF_3$, fluorine, chlorine, iodine, cyano, $C_{1-6}$ alkoxy, 5 or 6-membered aryl, saturated 5- or 6-membered heteromonocyclic group containing 1 or 3 nitrogen atoms, an unsaturated condensed heterocyclic group, saturated 3 to 6-membered heteromonocyclic group containing 1 to 4 nitrogen atoms, indolyl, isoindolyl, indolizinyl, benzimidazolyl, quinolyl, isoquinolyl, indazolyl, benzotriazolyl, tetrazolopyridazinyl, benzoxazolyl, benzoxadiazolyl, benzothiazolyl, benzothiadiazolyl, an unsaturated 5-membered heteromonocyclyl group containing 1 or 2 sulphur atoms; an unsaturated 5- or 6-membered heteromonocyclyl group containing 1 or 2 sulphur atoms and 1 or 2 nitrogen atoms, amino or $C_{1-6}$ alkylamino with the proviso that when R and R' are H and $R^2$ is $CO_2H$ or $CO_2Me$, then $R^3$ is not OH.

In an embodiment, it is preferred that $R^2$ is optionally substituted $C_{1-6}$ alkyl; optionally substituted $C_{2-6}$ alkenyl; optionally substituted aryl; optionally substituted heterocyclyl; optionally substituted $C_{1-6}$ alkoxy; $COR^6$ or $CSR^6$ in which $R^6$ is H, optionally substituted $C_{1-6}$ alkyl, optionally substituted $C_{2-6}$ alkenyl, hydroxy, optionally substituted aryl, optionally substituted heterocyclyl, $SR^7$ or $NR^7R^8$ in which $R^7$ and $R^8$ are either the same or different and selected from H, optionally substituted $C_{1-6}$ alkyl, optionally substituted $C_{2-6}$ alkenyl, optionally substituted aryl and optionally substituted heterocyclyl; CN; $(CH_2)_nNR^9R^{10}$, $HCNOR^9$ or $HCNNR^9R^{10}$, in which $R^9$ and $R^{10}$ are either the same or different and selected from H, optionally substituted $C_{1-6}$ alkyl, optionally substituted $C_{2-6}$ alkenyl, optionally substituted aryl and optionally substituted heterocyclyl and n is 1 to 4; $OR^{11}$, $SR^{11}$ or $NR^{11}R^{12}$ in which $R^{11}$ and $R^{12}$ are either the same or different and selected from H, optionally substituted $C_{1-6}$ alkyl, optionally substituted $C_{2-6}$ alkenyl, optionally substituted aryl and optionally substituted heterocyclyl or together form optionally substituted heterocyclyl; or $SO_2NR^{13}R^{14}$ in which $R^{13}$ and $R^{14}$ are either the same or different and selected from H, optionally substituted $C_{1-6}$ alkyl, optionally substituted $C_{2-6}$ alkenyl, optionally substituted aryl and optionally substituted heterocyclyl.

Another embodiment includes compounds wherein at least one of $R^2$, R, $R^3$ and R' is optionally substituted $C_{1-6}$ alkyl, optionally substituted aryl, optionally substituted heterocyclyl, $CH_2NR^9R^{10}$, $COR^6$ or $NR^{11}R^{12}$ in which $R^6$ is $NR^7R^8$.

Preferred compounds of formula Ia are as follows:

(a) Formula IIa

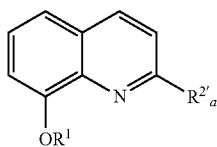

IIa wherein:

$R^1$ is as defined in formula I above; and $R^{2'}_a$ is optionally substituted $C_{1-6}$ alkyl, optionally substituted $C_{2-6}$ alkenyl, optionally substituted aryl or optionally substituted heterocyclyl.

Formula IIa may represent compounds wherein an antioxidant moiety is attached to the C2 position of the 8-hydroxyquinoline in such a way that exposure to a prooxidative environment, that is, hydroxy radicals, will result in a molecule with enhanced metal chelation properties.

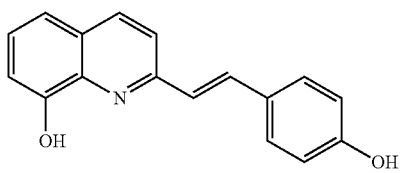

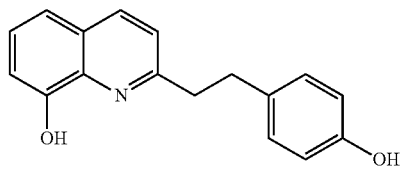

Representative examples are shown below:

(b) Formula IIIa

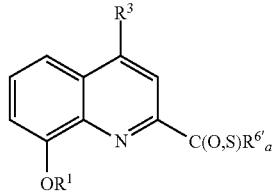

IIIa wherein:

$R^1$ and $R^3$ are as defined in formula I above; and $R^{6'}_a$ is optionally substituted $C_{1-6}$ alkyl, optionally substituted $C_{2-6}$ alkenyl, hydroxy, $OR^{7'}_a$, $SR^{7'}_a$, $N_2R^{7'}_aR^{8'}_a$, or $NR^{7'}_aR^{8'}_a$ wherein $R^{7'}_a$ and $R^{8'}_a$ are either the same or different and selected from H, optionally substituted $C_{1-6}$ alkyl, optionally substituted aryl and optionally substituted heterocyclyl.

Formula IIIa represents compounds wherein a hydrophilic amide moiety is attached to the C2 position of the 8-hydroxyquinoline so as to generally enhance solubility, while maintaining membrane permeability. Compounds of formula IIIa also show enhanced metal chelation properties.

Representative examples are shown below:

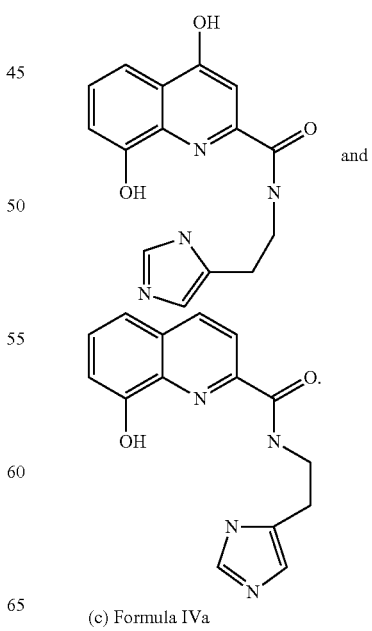

and (c) Formula IVa

-continued

IVa

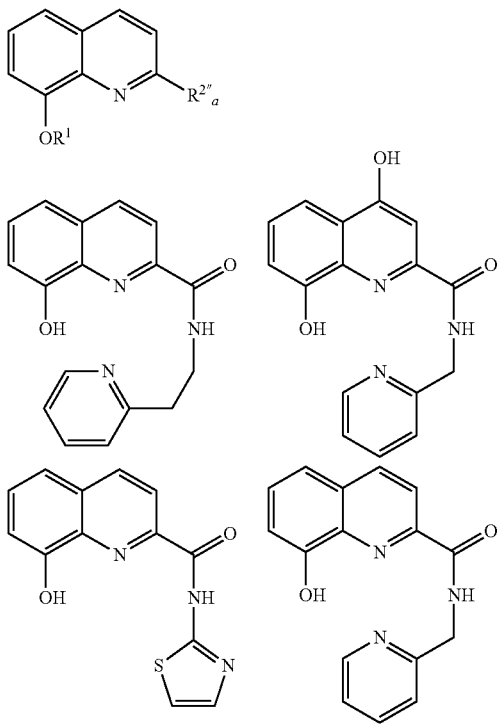

wherein:

R¹ is as defined in formula I above; and $R^{2''}_a$ is CN; $CH_2NR^{9'}_aR^{10'}_a$, $HCNOR^{9'}_a$ or $HCNNR^{9'}_aR^{10'}_a$ wherein $R^{9'}_a$ and $R^{10'}_a$ are either the same or different and selected from H, optionally substituted $C_{1-6}$ alkyl, optionally substituted alkenyl, optionally substituted aryl and optionally substituted heterocyclyl.

Formula IVa represents compounds which have improved metal chelation and optimised activity in the panel of assays described hereinafter.

Representative examples are shown below:

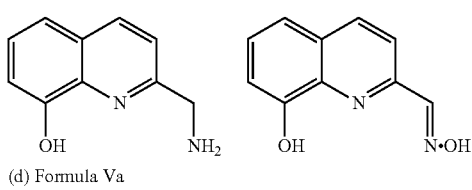

(d) Formula Va

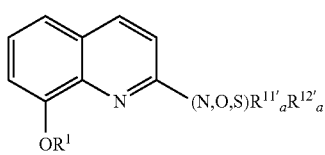

Va wherein:

R¹ is as defined in formula I above; and $R^{11'}_a$ and $R^{12'}_a$ are either the same or different and selected from H, optionally substituted $C_{1-6}$ alkyl, optionally substituted $C_{2-6}$ alkenyl, optionally substituted aryl and optionally substituted heterocyclyl or together form optionally substituted heterocyclyl.

(e) Formula VIa

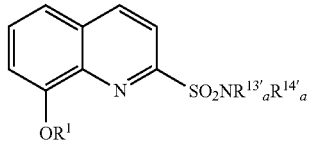

VIa wherein:

R¹ is as defined in formula I above; and $R^{13'}_a$ and $R^{14'}_a$ are either the same or different and selected from H, optionally substituted $C_{1-6}$ alkyl, optionally substituted $C_{2-6}$ alkenyl, optionally substituted aryl or optionally substituted heterocyclyl.

Preferred compounds of the present invention also include compounds of (ii) Formula Ib

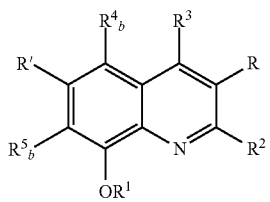

Ib wherein:

R¹, R', R, R² and R³ are as defined in formula I above;

$R^4_b$ and $R^5_b$ are either the same or different and selected from H; optionally substituted $C_{1-6}$ alkyl; optionally substituted $C_{2-6}$ alkenyl; halo; CN; $CF_3$; optionally substituted aryl; optionally substituted heterocyclyl; an antioxidant; a targeting moiety; $SO_3H$; $SO_2NR^{13}_aR^{14}_a$ wherein $R^{13}_a$ and $R^{14}_a$ are as defined in formula Ia above; $OR^{15}_b$, $SR^{15}_b$, $SO_2R^{15}_b$, $CONR^{15}_bR^{16}_b$ and $NR^{15}_bR^{16}_b$ wherein $R^{15}_b$ and $R^{16}_b$ are either the same or different and selected from H, optionally substituted $C_{1-6}$ alkyl, optionally substituted $C_{2-6}$ alkenyl, optionally substituted $C_{1-6}$ acyl, optionally substituted aryl and optionally substituted heterocyclyl, including provisos (a) to (c), (e), (g), (h), (I), (k), (o), (q), (r), and (u) as defined above.

Preferred compounds of formula Ib are as follows:

(a) Formula IIb

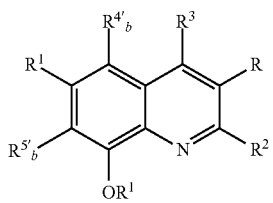

IIb wherein:

R¹, R', R, R² and R³ are as defined in formula I above; and $R^4_b$ and $R^5_a$ are as defined in formula Ib above provided that at least one is halo, including provisos (a), (c), (g), (h), (i), (o), (q) and (u) defined above.

(b) Formula IIIb

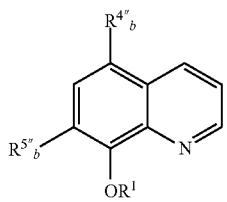

wherein:

$R^1$ is as defined in formula I above;

$R^{4''}_b$ is H or halo; and $R^{5''}_b$ is optionally substituted aryl or optionally substituted heterocyclyl.

A representative example is shown below:

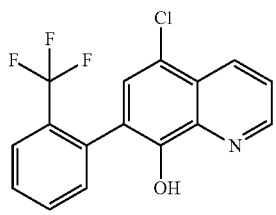

(c) Formula IVb

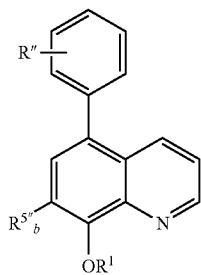

wherein:

$R^1$ is as defined in formula I above;

R" is $C_{1-6}$ alkoxy, halo, $C_{1-6}$ alkyl, $C_{2-6}$ alkenyl or $C_{1-6}$ haloalkyl; and $R^{5''}_b$ is H or halo.

A representative example is shown below:

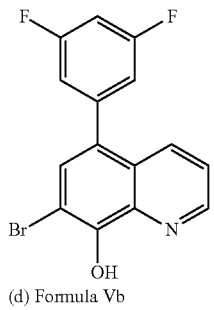

(d) Formula Vb

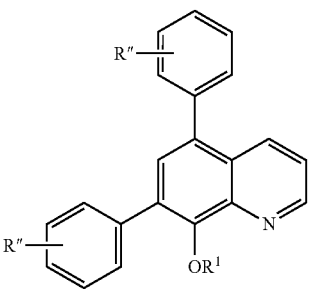

wherein $R^1$ is as defined in formula I above; and

R" is as defined in formula IVb above.

(e) Formula VIb

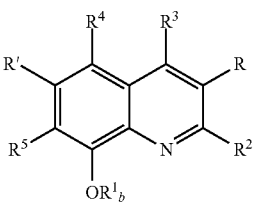

wherein:

$R^2$ to $R^5$, R and R' are as defined in formula I above; and $R^{1''}_b$ is optionally substituted $C_{1-6}$ alkyl, optionally substituted aryl, optionally substituted aryl acyl, $C_{1-6}$ alkyl acyl or optionally substituted heterocyclyl.

Formula VIb represents compounds wherein the 8-hydroxyl group on the quinoline is blocked to form a prodrug, in particular an ester prodrug. The 8-hydroxy represents a principal site of metabolism for the compound of Formula I: conjugation with glucuronic acid or sulphate gives a hydrophilic species ready to be excreted. Such conjugates probably do not pass the blood brain barrier. The ester prodrug may protect the compound of Formula I from conjugation. Esterases integral to the blood brain barrier may then release the C8-hydroxy on passage through that barrier activating the compound for its role in the CNS.

Another preferred compound of the present invention is a compound of (iii) Formula Ic

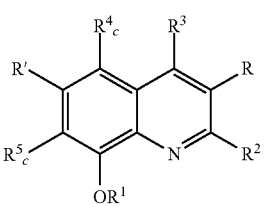

wherein $R^1$, $R^2$, $R^3$, R and R' are as defined in formula I; and at least one of $R^4_c$ and $R^5_c$ is halo and the other is selected from H, optionally substituted alkyl, optionally substituted alkenyl, optionally substituted alkoxy, optionally substituted acyl, hydroxy, optionally substituted amino, optionally substituted thio, optionally substituted sulphonyl, optionally substituted sulphinyl, optionally substituted sulphonylamino, $SO_3H$, amine, CN, $CF_3$, optionally substituted aryl, optionally substituted heterocyclyl, an antioxidant and a targeting moiety, salts, hydrates, solvates, derivatives, pro-drugs, tautomers and/or isomers thereof with the provisos that:

(a) when $R^1$ to $R^3$, R and R' are H, then $R^4_c$ is not chloro or iodo and $R^5_c$ is not iodo;

(b) when $R^1$, $R^5_c$, R' and R are H, $R^2$ is $CO_2H$ and $R^3$ is OH, then $R^4_c$ is not bromo;

(c) when $R^1$, R and R' are H, $R^2$ is $CO_2H$ and $R^3$ is OH, then $R^4_c$ and $R^5_c$ are not chloro;

(d) when $R^1$, $R^4_c$ and R' are H, $R^2$ is $CO_2H$ or $CO_2Me$ and $R^3$ is OH, then R and $R^5_c$ are not bromo;

(e) when $R^1$, R, R' and $R^5_c$ are H, $R^2$ is $CO_2Me$ and $R^3$ is OH, then $R^4_c$ is not bromo; and (f) when $R^1$, R and R' are H, $R^2$ is $CO_2Me$ and $R^3$ is OH, then $R^4_c$ and $R^5_c$ are not chloro.

Preferred compounds of Formula Ic are as follows:

(a) Formula IIc

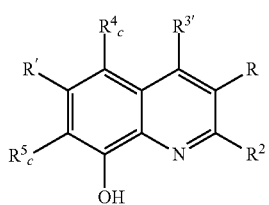

IIc wherein $R^2$, R, R', $R^4_c$ and $R^5_c$ are as defined in formula Ic; and $R^{3'}$ is H, optionally substituted alkyl, optionally substituted alkenyl, optionally substituted alkoxy, optionally substituted acyl, optionally substituted amino, optionally substituted thio, optionally substituted sulphonyl, optionally substituted sulphinyl, optionally substituted sulphonylamino, halo, $SO_3H$, amine, CN, $CF_3$, optionally substituted aryl, optionally substituted heterocyclyl, an antioxidant or a targeting moiety, with the proviso that at least one of R, $R^2$ and $R^{3'}$ is other than H.

Representative examples are shown below:

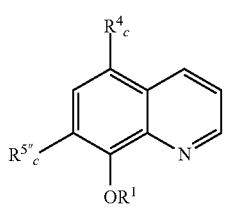

IIIc wherein $R^1$ is as defined in formula I and $R^4_c$ is as defined in formula Ic; and $R^{5''}_c$ is optionally substituted aryl or optionally substituted heterocyclyl;

(b) Formula IVc

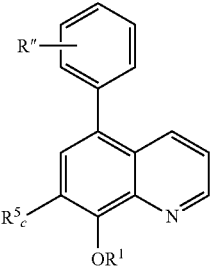

IVc wherein $R^1$ is as defined in formula I, $R^5_c$ is as defined in formula Ic and R'' is as defined in formula IVb; and (c) Formula Vc

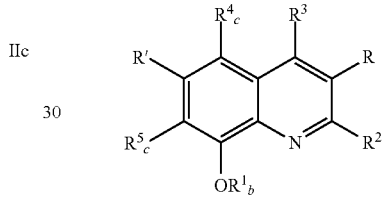

Vc wherein $R^2$, $R^3$, R and R' are as defined in formula I, $R^4_c$ and $R^5_c$ are as defined in formula Ic and $R^1_b$ is as defined in formula VIb.

In a particularly preferred embodiment, the compound of formula I is a compound of formula Ib, IIb or Ic wherein $R^4_b$ and $R^5_b$, $R^4_b{'}$ and $R^5_b{'}$ or $R^4_c$ and $R^5_c$, respectively are both halo, more preferably chloro substituents. Preferably, at least one of $R^2$, R, $R^3$ and R' is optionally substituted alkyl, optionally substituted aryl, optionally substituted heterocyclyl, $(CH_2)_nNR^9R^{10}$ wherein $R^9$ and $R^{10}$ are as defined above and n is 1 to 4, $COR^6$ wherein $R^6$ is $NR^7R^8$, $OR^7$ or $SR^7$ wherein $R^7$ and $R^8$ are as defined above or $NR^{11}R^{12}$, $OR^{11}$, $SR^{11}$ wherein $R^{11}$ and $R^{12}$ are as defined above.

While not wishing to be bound by theory, it is believed that substituents R, $R^3$ and R' have a limited effect, electronically or sterically, in the chelating properties of the compounds of the present invention. Substitution at those positions can therefore be used to modulate other parameters such as cytotoxicity and physicochemical properties including the number of hydrogen bond donors and acceptors, lipophilicity (C log P, E log P and Log D), solubility and polar surface area. Modulation of these parameters contribute to the optimisation of the pharmacokinetic profile of the compounds. It is also postulated that substituent $R^2$ in addition to modulating cytotoxicity and physicochemical properties could also affect activity if the substituent provides chelating properties. Examples of particularly preferred compounds having $R^2$ substituents with chelating properties are shown below.

PBT 1038

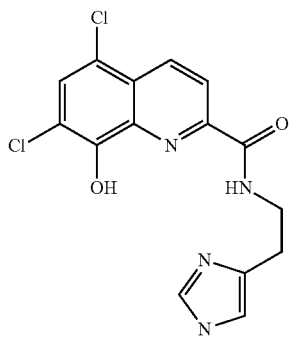

PBT 1050

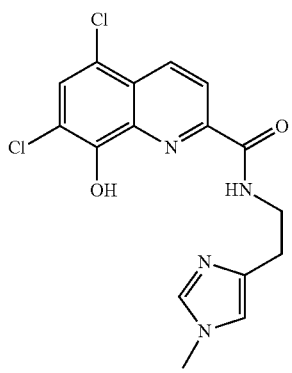

PBT 1052

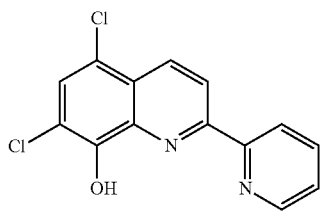

PBT 1033

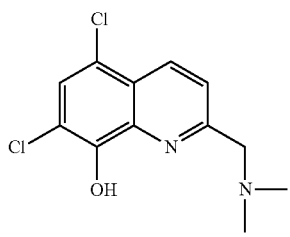

PBT 1056

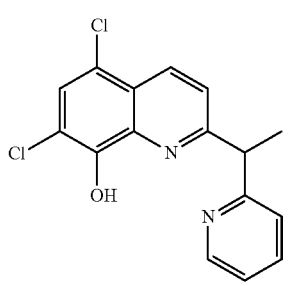

PBT 1051

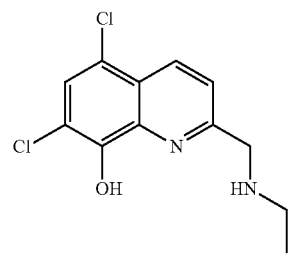

Other preferred compounds have the formula:

PBT 1058

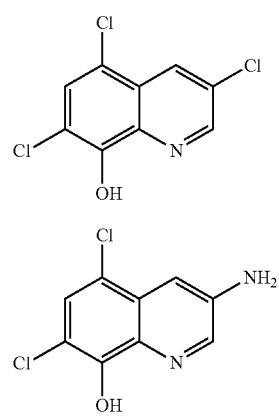

PBT 1060

PBT 1031

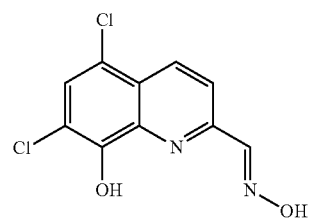

PBY 1032

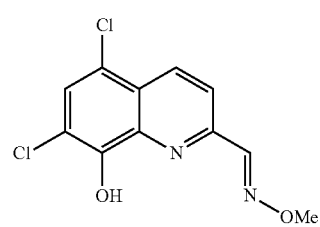

In a further aspect, the invention provides a pharmaceutical or veterinary composition comprising the compound of formula I as defined above, together with a pharmaceutically or veterinarily acceptable carrier.

Accordingly, the invention provides a compound of formula II which is a compound of formula I with the provisos that:

(a) when $R^1$ and $R^3$ to $R^5$, R and R' are H, then $R^2$ is not H, methyl,

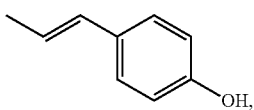

CO₂H, CN, CONCH₂CO₂H, COCH₃, CH₂NH₂, CNOH, (pyrid-2-yl), 2-hydroxyphenyl, CHNNH₂, NH-(pyrid-2-yl),

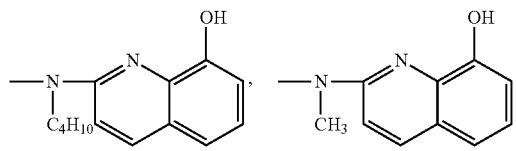

(b) when $R^1$ and $R^4$ to $R^7$ are H, then $R^3$ is not OH and $R^2$ is not CO₂H;

(c) when $R^1$ to $R^3$, $R^6$ and $R^7$ are H, then (i) when $R^5$ is I, $R^4$ is not Cl, SO₃H or I; (ii) when $R^5$ is H, $R^4$ is not SO₃H, NH₂ or Cl; (iii) $R^4$ and $R^5$ are both not Cl, Br or CH₃; and (iv) when $R^2$ to $R^7$ are H, then $R^1$ is not

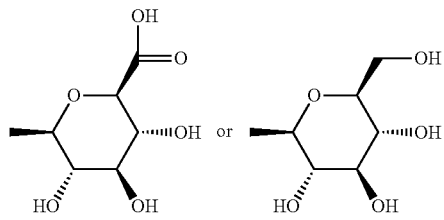

(d) when R1 to $R^3$, R and R' are H, then $R^4$ is not Cl or I and $R^5$ is not I;

(e) when R1 to $R^3$, R, R' and $R^5$ are H, then $R^4$ is not CHO, CHOHCCl₃,

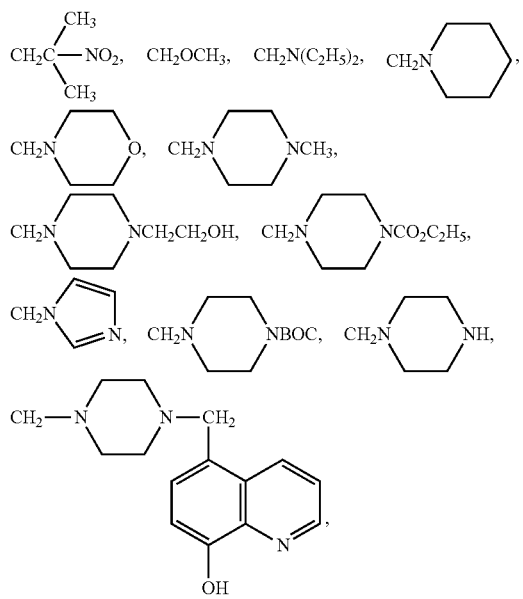

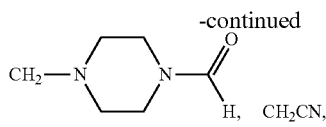

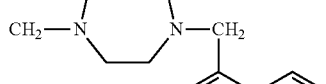

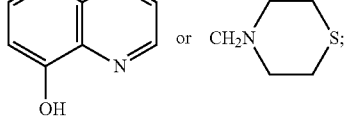

(f) when $R^1$, $R^5$, R' and R are H, $R^2$ is CO₂H and $R^3$ is OH, then $R^4$ is not bromo, methyl, phenyl, hydroxymethyl or trifluoromethyl;

(g) when $R^1$, $R^4$, $R^5$ and R are H, $R^2$ is CO₂H and $R^3$ is OH, then R' is not bromo, iodo, methyl, phenyl, propyl, phenethyl, heptyl, benzylaminomethyl, 3-aminopropyl, 3-hydroxypropyl, 4-methoxyphenyl, 3-methylphenyl, 4-chlorophenyl, 3,4-dichlorophenyl, pyridin-3-yl, furo-2-yl, 4-chlorophenyl, 3,4-dichlorophenyl, 2-chlorophenyl, 3-chlorophenyl, 2-chlorophenyl, 3-chlorophenyl, 2-methoxyphenyl or piperidin-2-yl;

(h) when $R^1$, $R^4$, R and R' are H, $R^2$ is CO₂H and $R^3$ is OH, then $R^5$ is not phenyl, 3-hydroxypropyl, phenethyl, 3-aminoprop-1-yl or hex-1-yl;

(i) when $R^1$, $R^4$, R' and $R^5$ are H, $R^2$ is CO₂H and $R^3$ is OH, then R is not N-morpholinomethyl, bromo or phenyl;

(j) when $R^1$, R and R' are H, $R^2$ is CO₂H and $R^3$ is OH, then $R^4$ and $R^5$ are not chloro;

(k) when $R^1$, $R^4$ and R' are H, $R^2$ is CO₂H and $R^3$ is OH, then R and $R^5$ are not bromo;

(l) when $R^1$, R, R' and $R^5$ are H, $R^2$ is CO₂Me and $R^3$ is OH, then $R^4$ is not hydroxymethyl, phenyl or bromo;

(m) when $R^1$, R, $R^4$ and $R^5$ are H, R2 is CO2Me and R3 is OH, then R' is not 4-methoxyphenyl, 3-methylphenyl, pyridin-3-yl, benzyl, bromo, 4-chlorophenyl, 3,4-dichlorophenyl, 3-hydroxypropyl or 3-tert-butoxycarbonylaminopropyl;

(n) when $R^1$, R, $R^4$ and R' are H, $R^2$ is CO₂Me and $R^3$ is OH, then $R^5$ is not phenyl or 3-tert-butoxycarbonylaminoprop-1-yl;

(o) when $R^1$, R, $R^4$, R' and $R^5$ are H and $R^2$ is CO₂Me, then $R^3$ is not toluene-4-sulphonylamino, piperazin-1-yl, morpholin-1-yl, piperidin-1-yl, 4-methylpiperazin-1-yl, 3-benzoylaminoprop-1-yl, phenethyl, 3-tert-butoxycarbonylaminopropyl, 3-hydroxypropyl, amino or hex-1-yl;

(p) when $R^1$, $R^4$, R' and $R^5$ are H, $R^2$ is CO₂Na and $R^3$ is OH, then R is not phenyl;

(q) when $R^1$, R, $R^4$, R' and $R^5$ are H and $R^2$ is CO₂H, then $R^3$ is not phenyl, 4-chlorophenyl, phenethyl, 3-hydroxypropyl, amino, morpholin-1-yl, piperidin-1-yl, 4-methylpiperazin-1-yl, toluene-4-sulphonylamino, 3-benzoylaminoprop-1-yl, aminoprop-1-ynyl, hex-1-yl, 5-hydroxypent-1-yl, piperazin-1-yl or 2-(1-piperazinyl)pyrimidinyl;

(r) when $R^1$, R' and R are H, $R^2$ is CO₂Me and $R^3$ is OH, then $R^4$ and $R^5$ are not chloro;

(s) when $R^1$, $R^4$, R' and $R^5$ are H, $R^2$ is CO₂Me and $R^3$ is OH, then R is not bromo;

(t) when $R^1$, R' and $R^4$ are H, $R^2$ is CO₂Me and $R^3$ is OH, then R and $R^5$ are not bromo;

(u) when $R^1$, R, $R^3$, R' and $R^5$ are H and $R^2$ is CO₂H, then $R^4$ is not phenyl, 4-chlorophenyl or phenylethyl;

(v) when $R^1$, $R^5$, R', $R^4$, $R^3$ and R are H, then $R^2$ is not 2H-tetrazol-1-yl;

(w) when $R^1$, $R^5$, $R^4$ and R are H, $R^2$ is $CO_2H$ and $R^3$ is OH, then R' is not 3,5-dichlorophenyl or 4-fluorophenyl; and (x) at least one of $R^1$ to $R^5$, R and R' is other than H;

(y) when $R^1$ to $R^3$, $R^5$, R' and R are H, then $R^4$ is not chloro, $NH_2$ or $SO_3H$; and (z) when $R^1$, $R^3$ to $R^5$, R and R' are H, then $R^2$ is not $CH_3$.

Preferably, the invention provides a compound of formula Ic, with the additional provisos that:

(d) when $R^1$ to $R^3$, R and R' are H, then $R^4_c$ and $R^5_c$ are both not chloro or bromo; and (e) when $R^1$ to $R^3$, $R^5_c$, R and R' are H, then $R^4_c$ is not chloro, more preferably a compound of formula IIc.

The compound of formula II defined above may be prepared using the processes described in detail hereinafter.

DETAILED DESCRIPTION OF THE INVENTION

Figure 1:
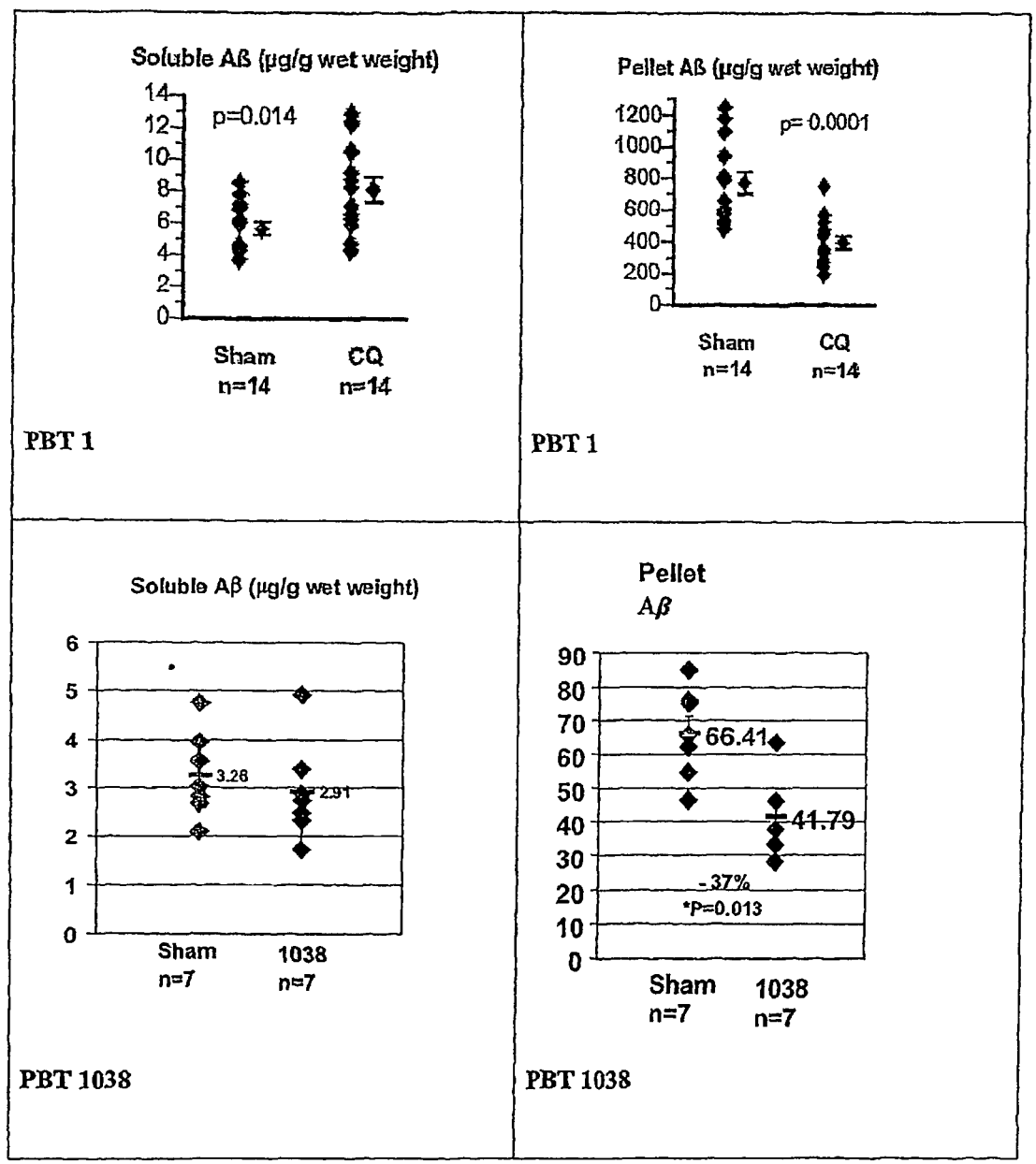
FIG. 1 is a scatterplot showing the levels of soluble and insolule Aβ fractions obtained from transgenic mice brains following treatment with PBT 1 and PBT 1038 [methodology as per assay 11]
Figure 2:
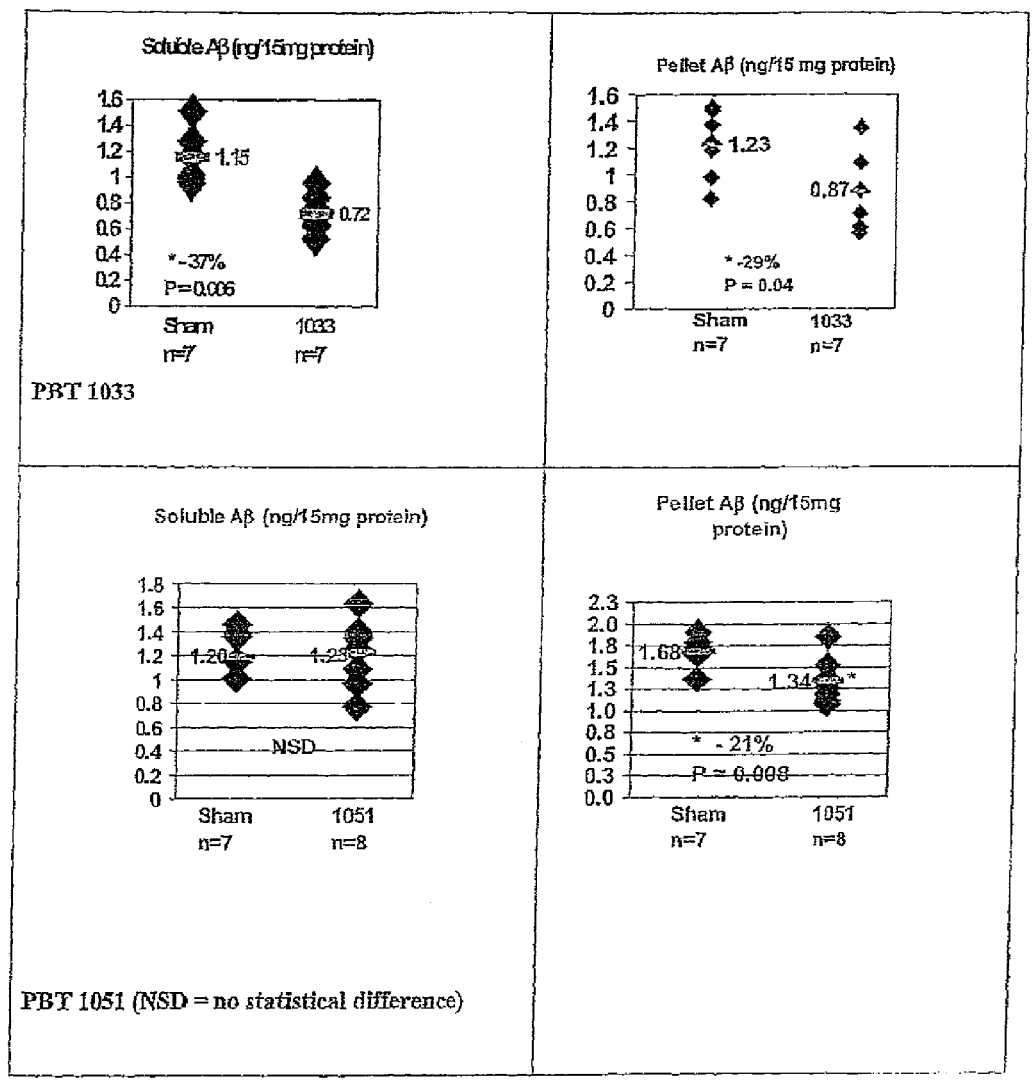
FIG. 2 is a scatterplot showing the levels of soluble and insolule Aβ fractions obtained from transgenic mice brains following treatment with PBT 1033 and PBT 1051 [methodology as per assay 11]
Figure 3:
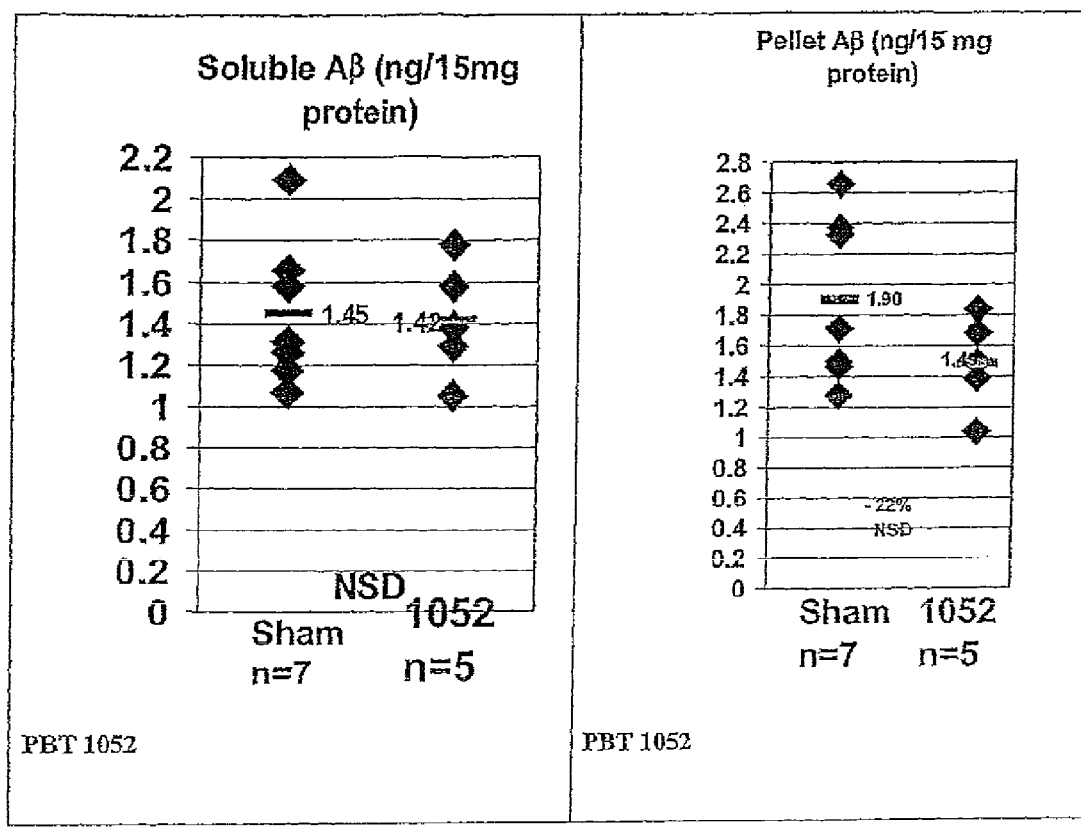
FIG. 3 is a scatterplot showing the levels of soluble and insolule Aβ fractions obtained from transgenic mice brains following treatment with PBT 1052 [methodology as per assay 11]

For the purposes of this specification it will be clearly understood that the word "comprising" means "including but not limited to", and that the word "comprises" has a corresponding meaning.

The term "alkyl" used either alone or in combination with terms such as "optionally substituted alkyl" "haloalkyl" or "alkyl acyl" refers to straight chain, branched chain or cyclic hydrocarbon groups having from 1 to 10 carbon atoms, preferably 1 to 6 carbon atoms, more preferably 1 to 4 carbon atoms. Illustrative of such alkyl groups are methyl, ethyl, propyl, isopropyl, butyl, isobutyl, sec-butyl, tert-butyl, pentyl, neopentyl, hexyl, cyclopropyl, cyclobutyl, cyclopentyl or cyclohexyl.

The term "alkenyl" used either alone or in combination with other terms such as "optionally substituted alkenyl", denotes linear, branched or mono- or poly-cyclic radicals having at least one carbon-carbon double bond of 2 to 20 carbon atoms, preferably 2 to 14 carbon atoms, and more preferably 2 to 6 carbon atoms. Examples of alkenyl radicals include allyl, ethenyl, propenyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cyclooctatetraenyl and the like.

The term "acyl" used either alone or in combination with other terms such as "optionally substituted acyl", "aryl acyl" or "alkyl acyl", denotes as part of a carboxylic acid or derivative thereof, e.g., amides, esters, anhydrides, and the like. It includes carbamoyl, aliphatic acyl group, acyl group containing an aromatic ring which is referred to as aromatic acyl or an acyl group containing a heterocyclic ring which is referred to as heterocyclic acyl. The acyl group preferably contains 1 to 20 carbon atoms, and more preferably 1 to 14 carbon atoms. Examples of acyl include carbamoyl; straight chain or branched alkanoyl, such as, formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl or icosanoyl; alkoxycarbonyl, such as, methoxycarbonyl, ethoxycarbonyl, t-butoxycarbonyl, t-pentyloxycarbonyl or heptyloxycarbonyl; cycloalkylcarbonyl, such as, cyclopropylcarbonyl, cyclobutylcarbonyl, cyclopentyl, carbonyl or cyclohexylcarbonyl; alkylsulfonyl, such as, methylsulfonyl or ethylsulfonyl; alkoxysulfonyl, such as, methoxysulfonyl or ethoxysulfonyl; aroyl, such as, benzoyl, toluoyl or naphthoyl; aralkanoyl, such as, phenylalkanoyl, for example, phenylacetyl, phenylpropanoyl, phenylbutanoyl, phenylisobutyl, phenylpentanoyl or phenylhexanoyl or naphthylalkanoyl, for example, naphthylacetyl, naphthylpropanoyl or naphthylbutanoyl; aralkenoyl, such as, phenylalkenoyl, for example, phenylpropenoyl, phenylbutenoyl, phenylmethacrylyl, phenylpentenoyl or phenylhexenoyl or naphthylalkenoyl, for example, naphthylpropenoyl, naphthylbutenoyl or naphthylpentenoyl; aralkoxycarbonyl, such as, phenylalkoxycarbonyl, for example, benzyloxycarbonyl; aryloxycarbonyl, such as, phenoxycarbonyl or naphthyloxycarbonyl, aryloxyalkanoyl, such as, phenoxyacetyl or phenoxypropionyl, arylcarbamoyl, such as, phenylcarbamoyl; arylthiocarbamoyl, such as, phenylthiocarbamoyl, arylglyoxyloyl, such as, phenylglyoxyloyl or naphthylglyoxyloyl; arylsulfonyl, such as, phenylsulfonyl or naphthylsulfonyl; heterocycliccarbonyl; heterocyclicalkanoyl, such as, thienylacetyl, thienylpropanoyl, thienylbutanoyl, thienylpentanoyl, thienylhexanoyl, thiazolylacetyl, thiadiazolylacetyl or tetrazolylacetyl, heterocyclicalkenoyl, such as, heterocyclicpropenoyl, heterocyclicbutenoyl, heterocyclicpentenoyl or heterocyclichexenoyl; or heterocyclicglyoxyloyl, such as, thiazolylglyoxyloyl or thienylglyoxyloyl.

The term "heterocyclyl group" used either alone or in combination with other terms such as "optionally substituted heterocyclyl" refers to monocyclic or polycyclic heterocyclic groups containing at least one heteroatom ring atom selected from nitrogen, sulphur and oxygen and containing up to 18 ring atoms and up to 17 carbon ring atoms. It is preferred that the heterocyclyl group is mono or bicyclic or tricyclic heterocyclic group containing up to 20 ring atoms and up to 17 ring carbon atoms, and at least 1 ring heteroatom selected from nitrogen, oxygen and sulphur The preferred heterocyclic group contains two or more ring heteroatoms; it is preferred that at least one of the ring heteroatoms is nitrogen.

The term heterocyclic, as used herein, also includes heteroaromatics that is an aryl, as defined herein, with at least one of the carbon ring atoms being replaced with at least one oxygen, sulfur or nitrogen ring atom.

The terms "saturated heterocyclic", or "saturated heteromonocyclic", and the like, whether in combination or alone as used herein, refers to a heterocyclic group in which there are no double or triple bonds present in or bonded to the heterocyclic ring.

But, the terms "unsaturated heterocyclic", "unsaturated heteromonocyclic" and the like, as used herein, whether in combination or alone, refers to a heterocyclic group which contains at least one double or triple bond and preferably at least one double bond, present in or bonded to the heterocyclic ring. Unless indicated to the contrary, these terms include heteroaromatics.

Suitable heterocyclic groups include N-containing heterocyclic groups, such as, unsaturated 3 to 6-membered and more preferably 5 or 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

saturated 3 to 6-membered and more preferably 5 or 6 membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 3 to 6-membered and more preferably 5 or 6 membered heteromonocyclic group containing an oxygen atom, such as, pyranyl or furyl;

unsaturated 3 to 6-membered and more preferably 5 to 6 membered heteromonocyclic group containing 1 or 2 sulphur atoms, such as, thienyl;

unsaturated 3 to 6-membered heteromonocyclic group and more preferably 5 or 6 membered containing 1 or 2 oxygen atoms and/or 1 to 3 nitrogen atoms, such as, oxazolyl, isoxazolyl or oxadiazolyl;

saturated 3 to 6-membered and more preferably 5-6 membered heteromonocyclic group containing 1 or 2 oxygen atoms and 1 or 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered and more preferably 5-6 membered heteromonocyclic group containing 1 or 2 sulphur atoms and 1 or 3 nitrogen atoms, such as, thiazolyl or thiadiazolyl;

saturated 3 to 6-membered and more preferably 5-6 membered heteromonocyclic group containing 1 or 2 sulphur atoms and 1 or 3 nitrogen atoms, such as, thiazolidinyl; and unsaturated condensed heterocyclic group containing 1 or 2 sulphur atoms and 1 or 3 nitrogen atoms, such as, benzothiazolyl or benzothiadiazolyl.

Preferably the heterocyclyl is an unsaturated 5- or 6-membered heteromonocyclic group containing 1, 2 or 3 nitrogen ring atoms such as imidazolyl, triazolyl, pyrazolyl or pyridinyl; an unsaturated condensed heterocyclic group such as quinolyl or benzothiadiazolyl; an unsaturated 5-membered heteromonocyclyl group containing 1 or 2 sulphur ring atoms such as thiophenyl; or an unsaturated 5- or 6-membered heteromonocyclyl group containing 1 or 2 sulphur atoms and 1 or 2 nitrogen atoms such as thiazolyl.

The term "aryl" used either alone or in combination with other terms such as "optionally substituted aryl" or "aryl acyl" denotes a carbocyclic aromatic system containing one, two or three rings wherein such rings may be attached together in a pendent manner or may be fused and containing up to 18 ring carbon atoms. This term excludes heteroaromatics. In addition, as defined, this term includes cyclic compounds in which at least one of the rings is aromatic, while any additional ring structures may be unsaturated or saturated. The term "aryl embraces aromatic radicals such as phenyl, naphthyl, tetrahydronaphthyl, indanyl and biphenyl. Preferably, the aryl is a 5- or 6-membered aryl such as phenyl.

The term "halo", used alone or in combination with other groups refers to fluorine, chlorine, bromine or iodine.

The term "optionally substituted thio," when used alone or in combination with other terms, refers to optional substituents, such as radicals containing a linear or branched alkyl of 1 to 10 carbon atoms, preferably 1 to 6 carbon atoms, more preferably 1 to 4 carbon atoms, attached to a divalent sulphur atom. Examples of alkylthio radicals include methylthio, ethylthio, propylthio, butylthio and hexylthio.

The term optionally substituted "sulfinyl" alone or in combination with other groups, refers to optional substituents such radicals containing a linear or branched alkyl radical, of 1 to 10 carbon atoms, preferably 1 to 6 carbon atoms, more preferably 1 to 4 carbon atoms, attached to a divalent —S(=O)— radical. Examples include methylsulfinyl, ethylsulfinyl, butylsulfinyl and hexylsulfinyl.

The term "optionally substituted sulfonyl" refers to optional substituents such as radicals containing a linear or branched alkyl radical of 1 to 10 carbon atoms, preferably 1 to 6 carbon atoms, more preferably 1 to 4 carbon atoms, attached to a divalent —SO$_2$— radical. Examples include methylsulfonyl, ethylsulfonyl and propylsulfonyl.

The term "alkoxy" when used alone or in combination with other groups, refers to straight chain or branched oxy-containing radicals preferably each having alkyl portions of 1 to about 6 carbon atoms. Examples of alkoxy include methoxy, ethoxy, propoxy, butoxy and tert-butoxy.

The term "optionally substituted" when used to modify a substituent refers to a group which may or may not be further substituted with one or more groups selected from alkyl, alkenyl, alkynyl, aryl, aldehyde, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, cyano, phosphorus-containing groups and the like. Preferably, the optional substituent is $C_{1-6}$ alkyl, more preferably $C_{1-4}$ alkyl; $CF_3$; fluorine; chlorine; iodine; cyano; $C_{1-6}$ alkoxy, more preferably $C_{1-4}$ alkoxy; aryl; heteroaryl; amino; or alkylamino.

The term "antioxidant" is used herein in its broadest sense and refers to a group which has the capacity to react with a reactive oxygen species such as a hydroxyl radical in such a way as to generate a non toxic product. Examples include phenols such as 3,4,5-trimethoxyphenyl and 3,5-di-t-butyl-4-hydroxyphenyl, indole amines such as melatonin and flavonoids. Other examples may be found the literature (Wright, 2001; Karbownik, 2001; Gilgun-Sherki, 2001).

The term "targeting moiety" is used herein in its broadest sense and refers to a group which will facilitate the brain delivery of the drug by way of an active transport mechanism. The targeting moiety is recognised by specific transporter enzymes integral to the blood brain barrier and these transporter enzymes then provide a mechanism for the drug to be imported into the brain. Typically such transporters are sodium dependant and their substrates contain carboxylic acids such as ascorbic acid and L-glutamate. Conjugation of the targeting moiety to the drug is enacted so as to retain the acid moiety. Examples can be found in the literature (Manfredini, 2002, Tamia, 1999).

The term "metal chelator" is used herein in its broadest sense and refers to compounds having two or more donor atoms capable of binding to a metal atom, preferably Cu, Zn or Fe wherein at least two of the donor atoms are capable of simultaneous binding to the metal atom and the resultant metal complex has a thermodynamic stability greater than or equal to that of the metal ion; biological ligand complex. The said use of metal chelators as treatments for neurological disorders in accordance with the present invention is distinguished from the previously known concept of "chelation therapy". "Chelation therapy" is a term associated clinically with the removal of bulk metals such as in Wilson's disease, β-thallesemia and haemochromatosis. The break down in metal homeostasis in these diseases can be described as a catastrophic event, much like a dam bursting, leading to overwhelming flooding of the problem metal. The mechanism of action of such compounds is that bulk metal is sequestered by the chelators and cleared by excretion. By way of comparison the breakdown in metal homeostasis associated with neurological conditions of the present invention is more akin to the constant drip of a leaky tap, which if left long enough will eventually cause local damage over a long period of time. The intention of the "metal chelator" of the present invention is to disrupt an abnormal metal-protein interaction to achieve a subtle repartitioning of metals and a subsequent normalization of metal distribution with the aim that once the toxic cycle is short-circuited, endogenous clearance processes can cope more effectively with the accumulating amyloidogenic protein.

The salts of the compound of Formula I or II are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water or common organic solvents. Such solvates are encompassed within the scope of the invention.

By "pharmaceutically acceptable derivative" is meant any pharmaceutically acceptable salt, hydrate, ester, amide, active metabolite, analogue, residue or any other compound which is not biologically or otherwise undesirable and induces the desired pharmacological and/or physiological effect.

The term "pro-drug" is used herein in its broadest sense to include those compounds which are converted in vivo to compounds of Formula I or II. Use of the pro-drug strategy optimises the delivery of the drug to its site of action, for example, the brain. In one aspect, the term refers to the presence of a $C_{1-6}$ alkyl or arylester moiety which is designed to resist hydrolysis until the pro-drug has crossed the blood-brain barrier ("BBB"), where esterases on the inner surface of the BBB act to hydrolyse the ester and liberate the C8 hydroxyl of the compounds of formula I or II. In a second aspect, the term refers to the attachment at C2 of the 8-hydroxyquinoline core of an antioxidant group, in particular the 3,4,-5-trimethoxyphenyl moiety or derivatives thereof. Exposure to the prooxidative environment of the brain will then lead to hydroxylation of the 3,4,5-trimethoxyphenyl group to give a 2-hydroxy-3,4,5-trimethoxyphenyl substituent, the hydroxyl group of which acts to enhance the chelation properties of the compounds of formula I or II.

The term "tautomer" is used herein in its broadest sense to include compounds of Formula I or II which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereoisomers. As the compound of Formula I or II may have one or more chiral centres, it is capable of existing in enantiomeric forms.

The compositions of the present invention comprise at least one compound of Formula I or II together with one or more pharmaceutically acceptable carriers and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

The term "neurological condition" is used herein in its broadest sense and refers to conditions wherein various cell types of the nervous system are degenerated and/or have been damaged as a result of neurodegenerative disorders or injuries or exposures. In particular, compounds of formula I or II can be used for the treatment of resulting conditions, wherein damage to cells of the nervous system has occurred due to surgical interventions, infections, exposure to toxic agents, tumours, nutritional deficits or metabolic disorders. In addition, compounds of the formula I or II can be used for the treatment of the sequelae of neurodegenerative disorders, such as Alzheimer's disease, Parkinson's disease, multiple sclerosis, amylotrophic lateral sclerosis, epilepsy, drug abuse or drug addiction (alcohol, cocaine, heroin, amphetamine or the like), spinal cord disorders and/or injuries, dystrophy or degeneration of the neural retina (retinopathies) and peripheral neuropathies, such as diabetic neuropathy and/or the peripheral neuropathies induced by toxins The term "neurodegenerative disorder" as used herein refers to an abnormality wherein neuronal integrity is threatened. Neuronal integrity can be threatened when neuronal cells display decreased survival or when the neurons can no longer propagate a signal. Neurological disorders that can be treated with the compounds of the present invention include but are not limited to acute intermittent porphyria; adriamycin-induced cardiomyopathy; AIDS dementia and HIV-1 induced neurotoxicity; Alzheimer's disease; amylotrophic lateral sclerosis; atherosclerosis; cataract; cerebral ischaemia; cerebral palsy; cerebral tumour; chemotherapy-induced organ damage; cisplatin-induced nephrotoxicity; coronary artery bypass surgery; Creutzfeldt-Jacob disease and its new variant associated with "mad cow" disease; diabetic neuropathy; Down's syndrome; drowning; epilepsy and post-traumatic epilepsy; Friedrich's ataxia; frontotemporal dementia; glaucoma; glomerulopathy; haemochromatosis; haemodialysis; haemolysis; haemolytic uraemic syndrome (Weil's disease); haemorrhagic stroke; Hallerboden-Spatz disease; heart attack and reperfusion injury; Huntington's disease; Lewy body disease; intermittent claudication; ischaemic stroke; inflammatory bowel disease; macular degeneration; malaria; methanol-induced toxicity; meningitis (aseptic and tuberculous); motor neuron disease; multiple sclerosis; multiple system atrophy; myocardial ischaemia; neoplasia; Parkinson's disease; peri-natal asphyxia; Pick's disease; progressive supra-nuclear palsy; radiotherapy-induced organ damage; restenosis after angioplasty; retinopathy; senile dementia; schizophrenia; sepsis; septic shock; spongiform encephalopathies; subharrachnoid haemorrhage/cerebral vasospasm; subdural haematoma; surgical trauma, including neurosurgery; thalassemia; transient ischaemic attack (TIA); traumatic brain injury (TBI); traumatic spinal injury; transplantation; vascular dementia; viral meningitis; and viral encephalitis.

Additionally, compounds of the present invention may also be used to potentiate the effects of other treatments, for example to potentiate the neuroprotective effects of brain derived nerve growth factor.

The invention is particularly directed to conditions which induce oxidative damage of the central nervous system, including acute and chronic neurological disorders such as traumatic brain injury, spinal cord injury, cerebral ischaemia, stroke (ischaemic and haemorragic), subharrachnoid haemorrage/cerebral vasospasm, cerebral tumour, Alzheimer's disease, Creutzfeldt-Jacob disease and its new variant associated with "mad cow" disease, Huntington's disease, Parkinson's disease, Friedrich's ataxia, cataract, dementia with Lewy body formation, multiple system atrophy, Hallerboden-Spatz disease, diffuse Lewy body disease, amylotrophic lateral sclerosis, motor neuron disease, multiple sclerosis, fatal familial insomnia, Gertsmann Straussler Sheinker disease and hereditary cerebral haemorrhage with amyoidoisis-Dutch type.

More particularly, the invention is directed to the treatment of neurodegenerative amyloidosis. The neurodegenerative amyloidosis may be any condition wherein neurological damage results from an abnormal interaction between a biological ligand such as a protein and redox active metal ions promoting reactive oxygen species formation, radicalization and/or the deposition of amyloid. The amyloid may be formed from a variety of protein or polypeptide precursors, including but not limited to Aβ, synuclein, huntingtin, SOD, amyloid precursor protein (APP) or prion protein.

Thus the condition is preferably selected from the group consisting of sporadic or familial Alzheimer's disease, amyotrophic lateral sclerosis, motor neuron disease, cataract, Parkinson's disease, Creutzfeldt-Jacob disease and its new variant associated with "mad cow" disease, Huntington's disease, dementia with Lewy body formation, multiple system atrophy, Hallerboden-Spatz disease, and diffuse Lewy body disease.

More preferably the neurodegenerative amyloidosis is an Aβ-related condition, such as Alzheimer's disease or dementia associated with Down syndrome or one of several forms of autosomal dominant forms of familial Alzheimer's disease (reviewed in St George-Hyslop, 2000). Most preferably the Aβ-related condition is Alzheimer's disease.

In a particularly preferred embodiment of all aspects of the invention, prior to treatment the subject has moderately or severely impaired cognitive function, as assessed by the Alzheimer's Disease Assessment Scale (ADAS)-cog test, for example an ADAS-cog value of 25 or greater.

In addition to slowing or arresting the cognitive decline of a subject, the methods and compounds of the invention may also be suitable for use in the treatment or prevention of neurodegenerative conditions, or may be suitable for use in alleviating the symptoms of neurodegenerative conditions. The compounds may be able to provide at least a partial reversal of the cognitive decline experienced by patients. If administered to a subject who has been identified as having an increased risk of a predisposition to neurodegenerative conditions, or to a subject exhibiting pre-clinical manifestations of cognitive decline, such as Mild Cognitive Impairment or minimal progressive cognitive impairment, these methods and compounds may be able to prevent or delay the onset of clinical symptoms, in addition to the effect of slowing or reducing the rate of cognitive decline.

Currently Alzheimer's disease and other dementias are usually not diagnosed until one or more warning symptoms have appeared. These symptoms constitute a syndrome known as Mild Cognitive Impairment (MCI), which was recently defined by the American Academy of Neurology, and refers to the clinical state of individuals who have memory impairment, but who are otherwise functioning well, and who do not meet clinical criteria for dementia (Petersen et al., 2001). Symptoms of MCI include:

(1) Memory loss which affects job skills
(2) Difficulty performing familiar tasks
(3) Problems with language
(4) Disorientation as to time and place (getting lost)
(5) Poor or decreased judgement
(6) Problems with abstract thinking
(7) Misplacing things
(8) Changes in mood or behaviour
(9) Changes in personality
(10) Loss of initiative MCI can be detected using conventional cognitive screening tests, such as the Mini Mental Status Exam, and the Memory Impairment Screen, and neuropsychological screening batteries.

The term "subject" as used herein refers to any animal having a disease or condition which requires treatment with a pharmaceutically-active agent. The subject may be a mammal, preferably a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates.

Suitable mammals include members of the Orders Primates, Rodentia, Lagomorpha, Cetacea, Carnivora, Perissodactyla and Artiodactyla. Members of the Orders Perissodactyla and Artiodactyla are particularly preferred because of their similar biology and economic importance.

For example, Artiodactyla comprises approximately 150 living species distributed through nine families: pigs (Suidae), peccaries (Tayassuidae), hippopotamuses (Hippopotamidae), camels (Camelidae), chevrotains (Tragulidae), giraffes and okapi (Giraffidae), deer (Cervidae), pronghorn (Antilocapridae), and cattle, sheep, goats and antelope (Bovidae). Many of these animals are used as feed animals in various countries. More importantly, many of the economically important animals such as goats, sheep, cattle and pigs have very similar biology and share high degrees of genomic homology.

The Order Perissodactyla comprises horses and donkeys, which are both economically important and closely related. Indeed, it is well known that horses and donkeys interbreed.

As used herein, the term "therapeutically effective amount" is meant an amount of a compound of the present invention effective to yield a desired therapeutic response, for example, to prevent or treat a neurological condition.

The specific "therapeutically effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

The compounds of the present invention may additionally be combined with other medicaments to provide an operative combination. It is intended to include any chemically compatible combination of pharmaceutically-active agents, as long as the combination does not eliminate the activity of the compound of formula I or II. It will be appreciated that the compound of the invention and the other medicament may be administered separately, sequentially or simultaneously.

Other medicaments may include, for example, where the condition is a β-amyloid related condition, particularly Alzheimer's disease, an inhibitor of the acetylcholinesterase active site, for example phenserine, galantamine, or tacrine; an antioxidant, such as Vitamin E or Vitamin C; an anti-inflammatory agent such as flurbiprofen or ibuprofen optionally modified to release nitric oxide (for example NCX-2216, produced by NicOx) or an oestrogenic agent such as 17-β-oestradiol.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA.

As used herein, a "pharmaceutical carrier" is a pharmaceutically acceptable solvent, suspending agent or vehicle for delivering the compound of formula I or II to the subject. The carrier may be liquid or solid and is selected with the planned manner of administration in mind. Each carrier must be pharmaceutically "acceptable" in the sense of being compatible with other ingredients of the composition and non injurious to the subject.

The compound of formula I or II may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection or infusion techniques.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and U.S. Pat. No. 4,265,874 to form osmotic therapeutic tablets for control release.

The compound of formula I or II as well as the pharmaceutically-active agent useful in the method of the invention can be administered, for in vivo application, parenterally by injection or by gradual perfusion over time independently or together. Administration may be intravenously, intraarterial, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

Generally, the terms "treating", "treatment" and the like are used herein to mean affecting a subject, tissue or cell to obtain a desired pharmacologic and/or physiologic effect. The effect is therapeutic in terms of a partial or complete cure of a disease and/or alleviation of symptoms associated with the disease. "Treating" as used herein covers any treatment of, amelioration of, or prevention of disease in a vertebrate, a mammal, particularly a human, and includes: (a) preventing the disease from worsening in a subject that may, have the disease, or (b) inhibiting the disease, i.e., arresting its development; or (c) relieving or ameliorating the effects of the disease, i.e., cause regression of the effects of the disease. Prophylaxis or synonym thereto refers to reducing the risks of a subject from having the disease, especially those predisposed to the disease.

The invention includes various pharmaceutical compositions useful for ameliorating disease. The pharmaceutical compositions according to one embodiment of the invention are prepared by bringing a compound of formula I or II, analogues, derivatives or salts thereof, or combinations of compound of formula I or II and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams and Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Compounds of formula I or II may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula I or II may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

Dosage levels of the compound of formula I or II of the present invention are of the order of about 0.5 mg to about 20 mg per kilogram body weight, with a preferred dosage range between about 0.5 mg to about 10 mg per kilogram body weight per day (from about 0.5 gms to about 3 gms per patient per day). The amount of active ingredient that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of active ingredient.

Optionally the compounds of the invention are administered in a divided dose schedule, such that there are at least two administrations in total in the schedule. Administrations are given preferably at least every two hours for up to four hours or longer; for example the compound may be administered every hour or every half hour. In one preferred embodiment, the divided-dose regimen comprises a second administration of the compound of the invention after an interval from the first administration sufficiently long that the level of active compound in the blood has decreased to approximately from 5-30% of the maximum plasma level reached after the first administration, so as to maintain an effective content of active agent in the blood. Optionally one or more subsequent administrations may be given at a corresponding interval from each preceding administration, preferably when the plasma level has decreased to approximately from 10-50% of the immediately-preceding maximum.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The invention will now be described in detail by way of reference only to the following non-limiting examples.
General 8-Hydroxyquinoline-2-carboxylic acid 1 (Shrader et al, 1988), 8-hydroxyquinoline-2-carbonitrile 2 (Shrader et al, 1988), 2-chloro-8-hydroxyquinoline 3 (Wang et al, 1996; Fleming et al, 1971), 2-aminomethylthiazole 4 (Dondoni et al, 1987, 1996), 2,5,7-trichloro-8-hydroxyquinoline 10 (Ostrovskaya et al, 1986), 5,7-dichloro-8-benzyloxy-quinoline-2-carboxylic acid 18 (Carissimi, M., 1972), 7-chloro-5-iodo-8-hydroxyquinoline 20 (Gershon et al, 1971), 4-chloro-8-methoxy-quinoline-3-carboxylic acid ethyl ester 25 (Richard et al, 1997) and 1-methyl-1H-histamine hydrochloride (Durant et al, 1976) were prepared according to the literature. The following compounds/reagents were sourced commercially: quinolines: 2-methyl-quinolin-8-ol, 8-hydroxy-quinoline (8-HQ) and 5,7-dibromo-8-hydroxy-quinoline were purchased from Fluka; 4,8-dihydroxy-quinoline-2-carboxylic acid, 5-chloro-7-iodo-8-hydroxy-quinoline, 5,7-dichloro-2-methyl-quinolin-8-ol and 5,7-diiodo-8-hydroxyquinoline were purchased from Aldrich; amines: histamine, 2-aminoethylyridine, 2-aminothiazole, 2-(2-aminoethyl)pyridine, 2-(aminomethyl)pyridine, 5-methyl-2-aminothiazole, 2-aminophenol, 1,2-diaminoethane, glycine, 1,2-phenylenediamine, di-(2-picolyl)amine and 2-(2-methylaminoethyl)pyridine were all purchased from Aldrich; aldehydes: 4-imidazolecarboxaldehyde, 2-thiazolecarboxaldehyde and 2-pyridinecarboxaldehyde were all purchased from Aldrich; azoles: pyrazole, imidazole, methylimidazole and 1H-1,2,3-triazole were purchased from Aldrich; boronic acids: 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 4-(dimethylamino)phenylboronic acid, 2-formylphenylboronic acid, thianaphthene-2-boronic acid, 3,5-difluorophenylboronic acid, 2,4-difluorophenylboronic acid, 3-thiopheneboronic acid, 3-fluorophenylboronic acid, 4-fluorophenylboronic acid and 3-nitrophenylboronic acid were all purchased from Aldrich; and organozinc reagents: 2-pyridylzinc bromide, 2-(methylthio)phenylzinc iodide, 2-(ethoxycarbonyl)phenylzinc iodide and 6-methylpyridylzinc bromide (0.5 M solution in THF) were commercially available (Aldrich). 3-Pyridylboronic acid was purchased from Frontier Scientific. Solvents were analytical grade and used as supplied. THF was distilled from sodium and benzophenone under argon. $^1$H NMR spectra (6, relative to TMS) were recorded on a Varian Unity 300 spectrometer unless otherwise indicated; J-Values are given in hertz. Mass spectral data were recorded on a Micromass Quattro II mass spectrometer.

Example 1

Preparation of 8-hydroxy-quinoline-2-carboxylic acid amides (Scheme 1)

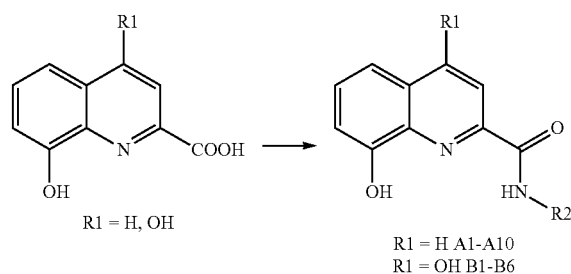

Scheme 1

R1 = H, OH

R1 = H A1-A10
R1 = OH B1-B6

Procedure A:

1,3-Dicyclohexylcarbodiimide (182 mg, 0.87 mmol) was added to a stirred solution of 1-hydroxybenzotriazole hydrate (119 mg, 0.87 mmol) and 8-hydroxy-quinoline-2-carboxylic acid 1 (150 mg, 0.87 mmol) in DMF and dichloromethane (1:1, 10 mL). After 30 min, histamine (182 mg, 0.87 mmol) was added and the mixture stirred at RT for a further 16 h. The volatiles were then removed in vacuo and the remaining residue gave, after purification by column chromatography on silica (ethyl acetate/i-PrOH/2 N NH$_4$OH, 6:2:1), 8-hydroxy-quinoline-2-carboxylic acid [2-(1H-imidazol-4-yl)-ethyl]-amide A1 as a cream-colored solid.

The above reaction was repeated using amines with 1 or 4,8-dihydroxy-quinoline-2-carboxylic acid: histamine gave B1; 2-(2-aminoethyl)pyridine gave A2, 2-(aminomethyl)pyridine gave A5/B2, 2-aminothiazole gave A3,5-methyl-2-aminothiazole gave A4, 2-aminophenol gave A6, 1,2-diaminoethane gave A7, glycine gave A8/B3, 1,2-phenylenediamine gave B4 and di-(2-picolyl)amine gave A10. Using A8 as the starting acid, coupling with amines 2-(aminomethyl)pyridine gave B5 and histamine gave B6. Yields and data are given in Table 1.

Procedure B:

8-Hydroxy-quinoline-2-carboxylic acid 1 (100 mg, 0.59 mmol) or 4,8-dihydroxyquinoline-2-carboxylic acid (121 mg, 0.59 mmol) and phosphorus oxychloride (5 mL) were heated under reflux for 1 h, cooled, and concentrated. THF (20 mL) was added to the residue and the mixture cooled (0° C.) before the addition of Et$_3$N (0.5 mL) and the amine (1.18 mmol). The mixture was allowed to warm to RT. After 16 h, the volatiles were removed in vacuo and the resulting residue afforded, after column chromatography on silica, the 8-hydroxy-quinoline-2-carboxylic acid amide. Yields and data are given in Table 1.

Example 2

Preparation of 2-Acetyl-8-hydroxy-quinoline C1 (Scheme 2)

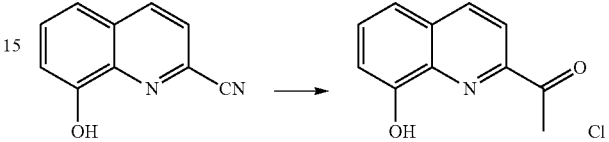

Scheme 2

Methylmagnesium bromide (1.2 mL of a 3 M solution in diethyl ether, 3.5 mmol) was added dropwise into a stirred solution of 8-hydroxyquinoline-2-carbonitrile 2 (100 mg, 0.588 mmol) in diethyl ether (10 mL) at −15° C. The resulting solution was allowed to warm to RT over 2 h and stirred at RT for a further 4 h. The reaction mixture was then quenched with saturated NH$_4$Cl and extracted with ethyl acetate (10 mL×3). The extracts were combined, dried (Na$_2$SO$_4$) and concentrated to afford the title compound as a pale orange solid (108 mg, 98%) C1. Spectral data of this compound are given in Table 1.

Example 3

Preparation of 8-Hydroxy-quinoline-2-carboxaldehyde Oxime D1 (Scheme 3)

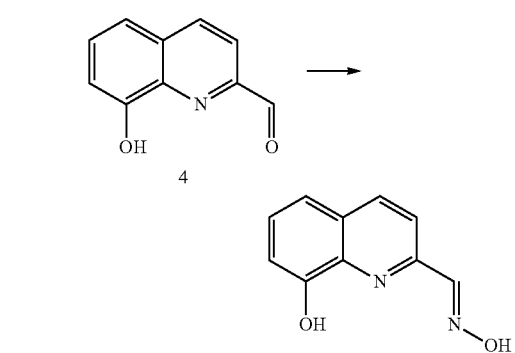

Scheme 3

4

D1

A solution of 2-methyl-quinolin-8-ol (536 mg, 3.37 mmol) in dioxane (8 mL) was added dropwise over 3 h into a stirred mixture of SeO$_2$ (665 mg, 5.99 mmol) in dioxane (25 mL) at 50-55° C. The resulting mixture was then heated at 80° C. for 16 h, cooled, and the solids filtered off. The filtrate was concentrated and the residue purified by column chromatography on silica (dichloromethane/MeOH, 1:0-40:1). This afforded 8-hydroxy-quinoline-2-carboxaldehyde 4 as a straw-coloured solid (358 mg, 61%). 4: $^1$H NMR (CDCl$_3$): δ 10.24 (s, 1H), 8.34 (d, J=8.6, 1H), 8.22 (br, 1H), 8.07 (d, J=8.6, 1H), 7.64 (dd, J=7.5 and 8.0, 1H), 7.44 (d, J=8.0, 1H), 7.30 (d, J=7.5, 1H). The mixture of 4 (100 mg, 0.578 mmol), NaOAc (63 mg, mmol), hydroxylamine hydrochloride (60 mg, 0.863 mmol) and water (5 mL) was heated at 100° C. for 15 min. The precipitate was isolated by filtration. This provided the title oxime (ID 969) D1 as an off-white solid (87 mg, 80%); spectral data of this compound are shown in Table 2.

Example 4

2-Aminomethyl-quinolin-8-ol E1 (Scheme 4)

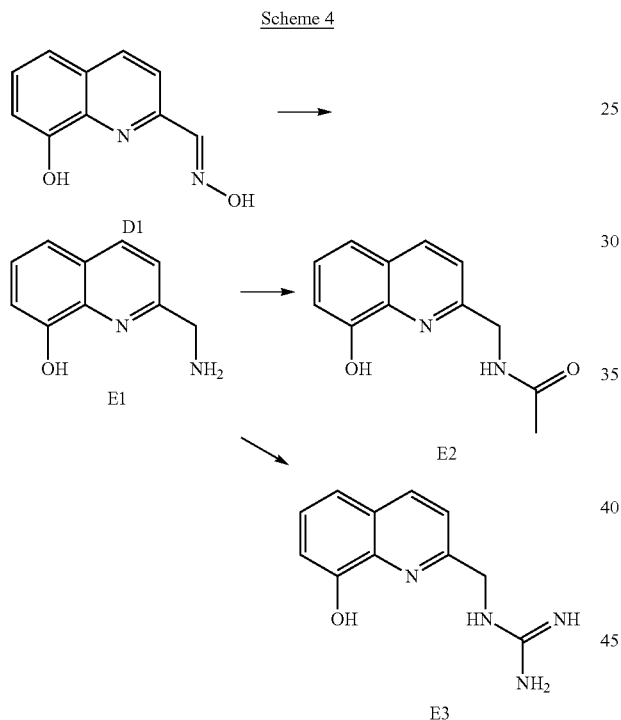

8-Hydroxy-quinoline-2-carboxaldehyde oxime D1 (167 mg, 0.888 mmol) and MeOH (50 mL) was treated under hydrogenolysis conditions (atmospheric H$_2$, catalytic 10% Pd/carbon) at RT. After 4 h, the catalyst was filtered off and the volatiles removed which afforded 2-aminomethyl-quinolin-8-ol E1 as a light brown solid (126 mg, 82%); spectral data of this compound are given in Table 2.

N-(8-Hydroxy-quinolin-2-ylmethyl)-guanidine E3 (Scheme 4)

N,N'-Bis(tert-butoxycarbonyl)-1H-pyrazole-1-carboxamidine (54 mg, 0.174 mmol) was added to a stirred mixture of 2-aminomethyl-quinolin-8-ol E1 (25 mg, 0.144 mmol) in THF (5 mL). After 16 h at RT, the volatiles were removed in vacuo and the residue provided, after column chromatography on silica (ethyl acetate/hexane, 1:2), the (Boc)$_2$-derivative of N-(8-Hydroxy-quinolin-2-ylmethyl)-guanidine as a colorless solid (52 mg, 87%). A solution of this solid (47 mg, 0.113 mmol) and concentrated hydrochloric acid (0.5 mL) in dioxane (1 mL) was then stirred at RT for 16 h, and concentrated. H$_2$O (2 mL) was added, the pH adjusted to 8 (conc. NH$_4$OH) and the mixture concentrated. The solid was dissolved in MeOH and the solution triturated with ethyl acetate. The resulting solid was filtered off and the filtrate was concentrated to a solid. The latter, after column chromatography on silica (ethyl acetate/i-PrOH/H$_2$O, 12:4:1), afforded the title compound E3 as an off-white solid (23 mg, 94%); spectral data are given in Table 2.

2-Acetamidomethyl-quinolin-8-ol E2 (Scheme 4)

A solution of 2-aminomethyl-quinolin-8-ol E1 (30 mg, 0.172 mmol) and Ac$_2$O (1 mL) in pyridine (2 mL) was stirred at RT overnight and concentrated. Subsequent column chromatography on silica (ethyl acetate) gave 2-acetamido-8-acetoxy-quinoline as a colorless solid (35 mg, 79%). A solution of 2-acetamido-8-acetoxy-quinoline (33 mg, 0.128 mmol) and K$_2$CO$_3$ (50 mg, 0.362 mmol) in MeOH (1 mL) and H$_2$O (0.5 mL) was stirred at RT for 16 h. Volatiles were removed in vacuo and H$_2$O (2 mL) added. The pH of the mixture was adjusted to 7 (2 N HCl) and the solid was isolated by filtration, washed with H$_2$O (1 mL×2) and dried. The title compound E2 was isolated as a cream solid (21 mg, 76%); spectral data are given in Table 2.

Example 5

Reductive amination of 8-hydroxyquinoline-2-carboxaldehyde (Scheme 5)

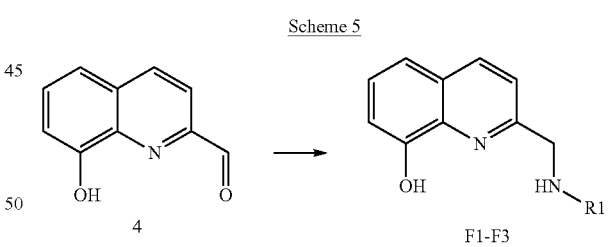

Sodium triacetoxyborohydride (225 mg, 1.061 mmol) was added to a stirred solution of 8-hydroxy-quinoline-2-carboxaldehyde 4 (200 mg, 1.156 mmol) and histamine (128 mg, 1.152 mmol) in dichloroethane (10 mL). The mixture was left to stir at RT for 16 h, neutralized (aqueous NaHCO$_3$), and concentrated. The resulting residue, after column chromatography on silica (ethyl acetate/i-PrOH/2 N NH$_4$OH, 6:2:1), afforded 2-{[2-(1H-imidazol-4-yl)-ethylamino]-methyl}-quinolin-8-ol F1 as a straw-colored solid (190 mg, 61%). The above method was repeated using other amines: 2-(aminomethyl)pyridine gave F2 and 2-(2-methylaminoethyl)pyridine gave F3, data given in Table 2.

Example 6

Reductive Amination with Amines from Example 5 (Scheme 6)

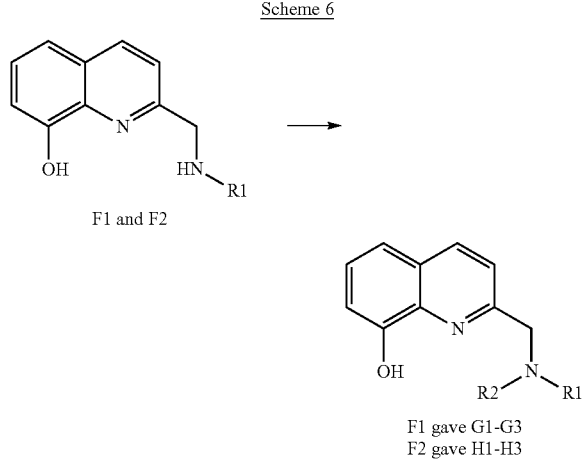

Scheme 6

F1 and F2

F1 gave G1-G3
F2 gave H1-H3

Following the procedure of Example 5, aldehydes: 2-imidazolecarboxaldehyde gave G1/H1, 2-pyridinecarboxaldehyde gave G2/H2 and 2-thiazolecarboxaldehyde gave H3 when treated with F1 (G series) or F2 (H series). Results and spectral data are given in Table 2.

Example 7

2-(Azole)-8-hydroxyquinolines I1-I4 (Scheme 7)

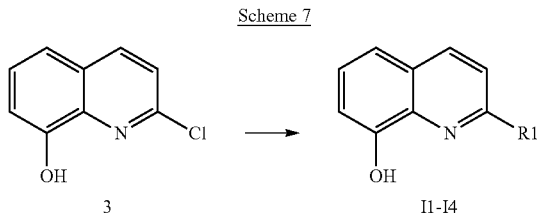

Scheme 7

3 → I1-I4

A mixture of 2-chloro-quinolin-8-ol 3 (80 mg, 0.447 mmol) and pyrazole (152 mg, 2.233 mmol) was heated at 175° C. in a steel autoclave for 48 h. The crude product was then purified by column chromatography on silica (ethyl acetate/hexane, 1:1) to give 2-pyrazol-1-yl-quinolin-8-ol (compound ID 964) I1 as a white solid (68 mg, 72%).

The above procedure was repeated using imidazole, 2-methylimidazole and 1H-1,2,3-triazole to give I2, I3 and I4. The crude product for I4 was washed with MeOH (10 mL×3) to give 2-[1,2,3]triazol-1-yl-quinolin-8-ol (compound ID 994) I4 as an off-white solid (67 mg, 71%). Spectral data of these products are given in Table 3.

Example 8

Preparation of 5-chloro-7-aryl-8-hydroxyquinolines K1-K17 (Scheme 8)

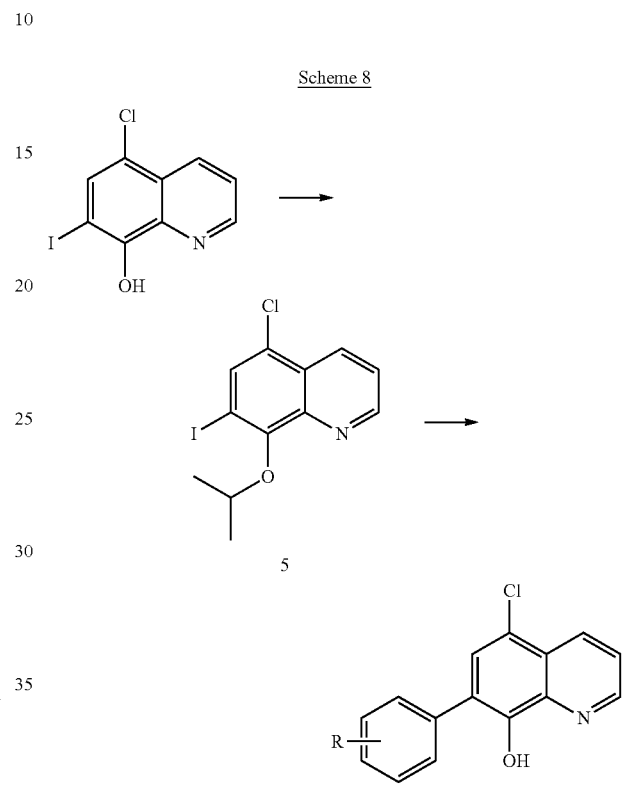

Scheme 8

K1-K17

2-Bromopropane (0.46 mL, 4.90 mmol) was added into a stirred mixture of the 5-chloro-7-iodo-quinolin-8-ol (1.00 g, 3.27 mmol), $K_2CO_3$ (1.86 g, 13.5 mmol) and DMSO (10 mL). After 16 h at RT, saturated $NH_4Cl$ (10 mL) was added and the mixture extracted with dichloromethane (10 mL×3). The extracts were combined and concentrated. Diethyl ether (40 mL) was added to the residue and the resulting mixture washed successively with 2 N NaOH, $H_2O$ and brine, and dried ($Na_2SO_4$). Subsequent column chromatography on silica (ethyl acetate/hexane, 1:1) afforded 5-chloro-7-iodo-8-isopropoxy-quinoline 5 as a solid (1.06 g, 93%). 5: $^1$H NMR ($CDCl_3$): δ 8.93 (dd, J=1.5 and 4.2, 1H), 8.52 (dd, J=1.5 and 8.4, 1H), 7.98 (s, 1H), 7.53 (dd, J=4.2 and 8.4, 1H), 5.38 (m, 1H), 1.43 (d, J=6.0, 6 H). To a stirred mixture of 5-chloro-7-iodo-8-isopropoxy-quinoline 5 (200 mg, 0.58 mmol), phenylboronic acid (77 mg, 0.62 mmol), 2 N $Na_2CO_3$ (7.2 mL), EtOH (1.2 mL) and benzene (6 mL) was added, under a blanket of argon, $Pd(PPh_3)_4$ (20 mg). The mixture was stirred under reflux for 16 h, cooled and concentrated. This provided, after column chromatography on silica (ethyl acetate/hexane, 1:9), 5-chloro-7-phenyl-8-isopropoxy-quinoline as a yellow solid. To a stirred solution of the 8-isopropoxy-quinoline (0.339 mmol) in dichloromethane (2 mL) at −78° C. was added $BCl_3$ (1.36 mL of a 1 M solution in dichloromethane, 1.36 mmol). After 2 h, the reaction mixture was allowed to warm to RT and stirred for a further 2 h. MeOH (5 mL) was added and the mixture was concentrated to dryness. This process was repeated four times. Further washing of the remaining residue with diethyl ether (2 mL×3) provided K1 in 91% yield. Data in Table 4.

In a similar fashion, reaction of 5 with boronic acids: 2-(trifluoromethyl)phenylboronic acid, 2-methoxyphenylboronic acid (Note cleavage to the 2-hydroxyphenyl derivative), o-tolylboronic acid, 2-fluorophenylboronic acid, 3-methoxyphenylboronic acid, 4-methoxyphenylboronic acid, m-tolylboronic acid, 4-(dimethylamino)phenylboronic acid, 2-formylphenylboronic acid, thianaphthene-2-boronic acid, 3,5-difluorophenylboronic acid, 2,4-difluorophenylboronic acid, 3-thiopheneboronic acid, 3-fluorophenylboronic acid, 4-fluorophenylboronic acid and 3-nitrophenylboronic acid; and isopropoxy cleavage with BCl$_3$ gave 5-chloro-7-aryl-8-hydroxyquinolines K2-K17. Data in Table 4.

Example 9

Preparation of 5-aryl-7-bromo-8-hydroxyquinolines L1-L2 (Scheme 9)

Scheme 9

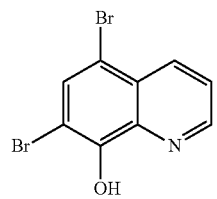

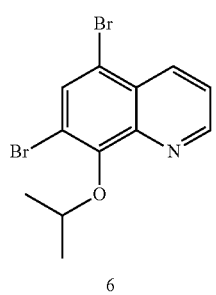 → 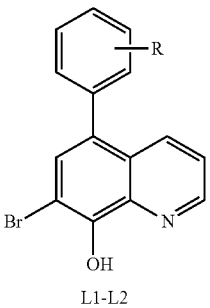

Reaction of 5,7-dibromo-quinolin-8-ol with 2-bromopropane following the method described in Example 8 gave 5,7-dibromo-8-isopropoxy-quinoline 6 (97%): $^1$H NMR (CDCl$_3$): δ 8.94 (dd, J=1.5 and 4.2, 1H), 8.48 (dd, J=1.5 and 8.4, 1 H), 8.00 (s, 1H), 7.52 (dd, J=4.2 and 8.4, 1H), 5.22 (m, 1H), 1.43 (d, J=6.1, 6 H); mass spectrum: m/z 344, 346, 348 (M$^+$+1, 50, 100 and 50%, respectively). Reaction of 6 with aryl boronic acids, and cleavage of the isopropoxy group following the method outlined in Example 8 gave compounds L1 and L2 (data in Table 4).

Example 10

Preparation of 5,7-diaryl-8-hydroxyquinolines M1-M5 and 5-aryl-7-iodo-8-hydroxyquinolines N2-N5 (Scheme 10)

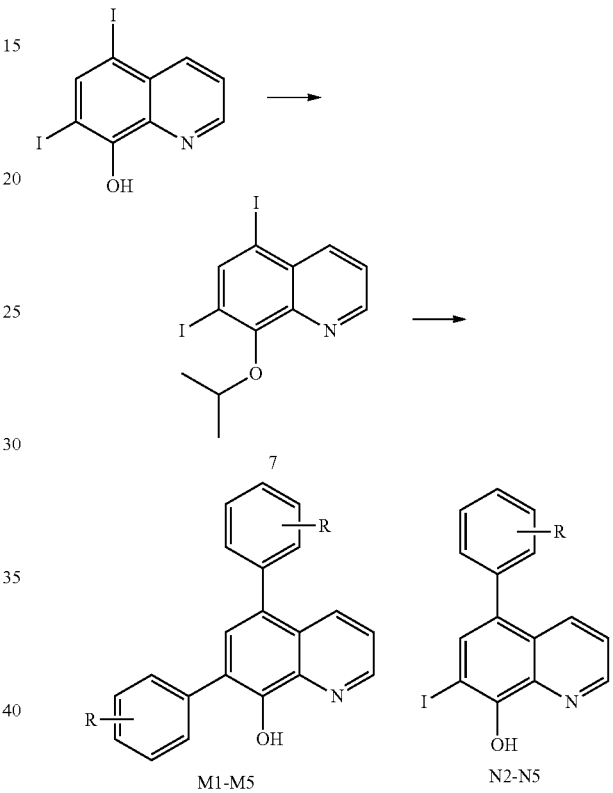

Preparation of 5,7-diaryl-8-hydroxyquinolines M1-M5 and 5-aryl-7-iodo-8-hydroxyquinolines N2-N5 (Scheme 10)

Reaction of 5,7-diiodo-quinolin-8-ol with 2-bromopropane following the method described in Example 8 gave 5,7-dibromo-8-isopropoxy-quinoline 7 (93%): $^1$H NMR (CDCl$_3$): δ 8.86 (dd, J=1.5 and 4.4, 1H), 8.46 (s, 1H), 8.33 (dd, J=1.5 and 8.5, 1H), 7.49 (dd, J=4.4 and 8.5, 1H), 5.40 (m, 1H), 1.43 (d, J=6.1, 6 H). To a stirred mixture of 7 (200 mg, 0.51 mmol), phenylboronic acid (143 mg, 1.17 mmol), 2 N Na$_2$CO$_3$ (7.2 mL), EtOH (1.2 mL) and benzene (6 mL) was added, under a blanket of argon, Pd(PPh$_3$)$_4$ (21 mg). The mixture was stirred under reflux for 16 h, cooled and concentrated. This provided, after column chromatography on silica (ethyl acetate/hexane, 1:9), 5,7-diphenyl-8-isopropoxy-quinoline as a yellow solid (157 mg, 91%). Cleavage of the isopropoxy group following the method outlined in Example 8 gave 5,7-diphenyl-8-hydroxy-quinoline M1 in 91% yield. (See table 4 for data).

Reaction of 7 with aryl boronic acids, and cleavage of the isopropoxy group following the method outlined in Example 8 gave compounds M2-M5 (data in Table 4). In those cases where the boronic acid contained an ortho substituent, the Suzuki reaction yielded a mixture of 5-aryl-7-iodo-8-isopropoxyquinolines and 5,7-diaryl-8-isopropoxyquinoline, which could be separated prior to isopropoxy cleavage to provide both 5-aryl-7-iodo-8-hydroxyquinolines N2-N5 and 5,7-diaryl-8-hydroxyquinolines M2-M5.

Example 11

Preparation of 5,5'-Dichloro-8,8'-dihydroxy-7,7'-biquinoline O1 (Scheme 11)

Scheme 11

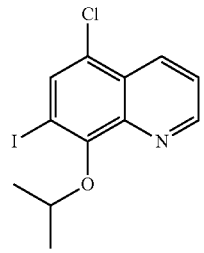

5

A solution of 5 (0.576 mmol), bis(pinacolato)diboron (1.1 equiv.), 2 N Na$_2$CO$_3$ (2 mL) and KOAc (3 equiv) was stirred in the presence of a catalytic amount of PdCl$_2$(dppf) in DMF (10 mL) at 80° C. for 3 h. The reaction mixture was then quenched with saturated NH$_4$Cl and extracted with diethyl ether (10 mL×3), dried (Na$_2$SO$_4$), and concentrated. Column chromatography of the resulting residue (silica; ethyl acetate/hexane, 1:1) afforded 5,5'-dichloro-8,8'-diisopropoxy-7,7'-biquinoline (compound ID 971) as a solid (56 mg, 22%).

Cleavage of the isopropoxy groups with BCl$_3$ following the procedure outlined in Example 8 gave O1 in 22% yield.

Example 12

Preparation of 2-aryl-8-hydroxyquinolines P1-P4 (Scheme 12)

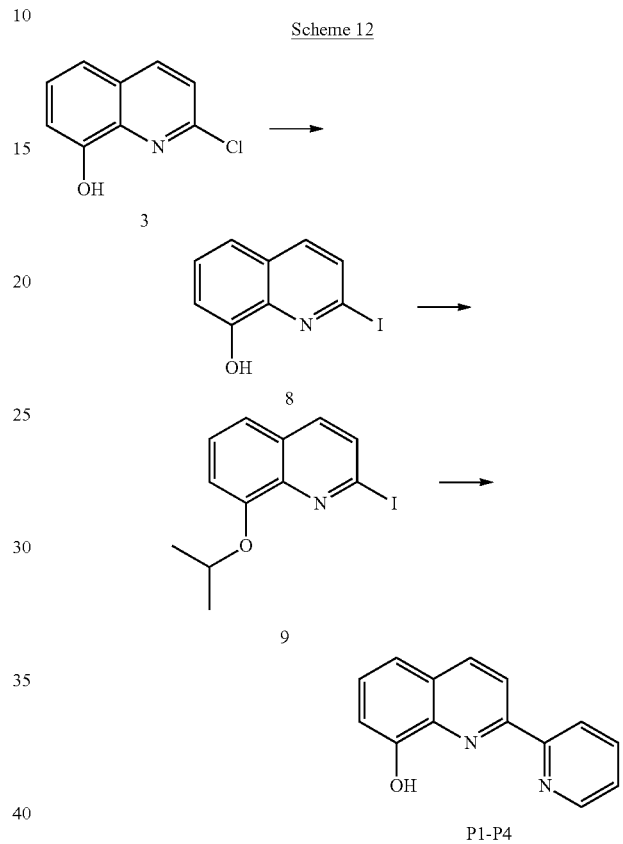

Scheme 12

2-Iodo-quinolin-8-ol 8

Acetyl chloride (0.422 mL, 5.95 mmol) was added dropwise over 20 min into a stirred slurry of 2-chloro-quinolin-8-ol 3 (500 mg, 2.79 mmol), NaI (649 mg, 4.33 mmol) and AcCN (3 mL) at RT$^5$. The mixture was then stirred at 35-40° C. for 3 h, then overnight at 70° C., and concentrated. H$_2$O (10 mL) was added, and mixture was extracted with dichloromethane (10 mL×3). The extracts were combined and washed successively with a 1:1 solution of saturated NaHCO$_3$ and sodium thiosulfate (5 mL×2), and H$_2$O (10 mL×2), and dried (Na$_2$SO$_4$). The residue obtained after solvent removal gave, after column chromatography on silica (ethyl acetate/hexane, 1:8-1:3), 2-Iodo-quinolin-8-ol 8 as a white solid (268 mg, 35%) and a 1:2 inseparable mixture of 8-acetoxy-2-iodo-quinoline and 8-acetoxy-2-chloro-quinoline (360 mg) 8: $^1$H NMR (CDCl$_3$): δ 7.80-7.77 (m, 2H), 7.49 (dd, J=8.1 and 8.1, 1H), 7.73 (d, J=8.1, 1H), 7.21 (d, J=8.1, 1H), 1.77 (br, 1H); mass spectrum: m/z 272 (M$^+$+1, 100%).

2-(Pyrid-2-yl)-8-hydroxyquinoline M1

Reaction of 2-iodo-quinolin-8-ol 8 with 2-bromopropane following the method described in Example 8 gave 2-iodo-8-

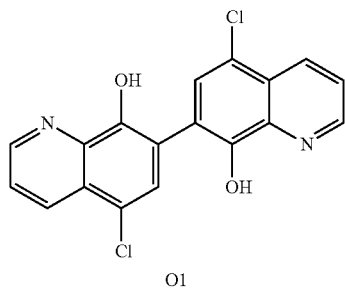

O1 isopropoxyquinoline 9 in 84% yield. 9: $^1$H NMR (CDCl$_3$): δ 7.75-7.67 (m, 2H), 7.45 (dd, J=7.0 and 8.0, 1H), 7.33 (dd, J=1.2 and 8.0, 1H), 7.12 (dd, J=1.2 and 7.0, 1H), 4.80 (m, 1H), 1.49 (d, J=5.9, 6 H). To a stirred solution of 9 (29 mg, 0.093 mmol) and PdCl$_2$(PPh$_3$)$_2$ (5 mg) in THF (2.5 mL) under an argon atmosphere at RT was added dropwise over 5 min 2-pyridylzinc bromide (0.370 mL of a 0.5 M solution in THF, 0.185 mmol). After 2 h, saturated NH$_4$Cl (5 mL) was added and the mixture extracted with dichloromethane (10 mL×3). The combined extracts were washed with H$_2$O (10 mL) and brine (10 mL), dried (Na$_2$SO$_4$), and concentrated. Subsequent column chromatography on silica (dichloromethane/MeOH, 19:1) gave 2-(pyrid-2-yl)-8-isopropyloxyquinoline as a yellow solid. The isopropyl ether was cleaved according to the procedure of Example 8, to give 2-(Pyrid-2-yl)-8-hydroxyquinoline P1 (22 mg, 89%) (data in Table 5).

This reaction was repeated using: 2-(methylthio)phenylzinc iodide, 2-(ethoxycarbonyl)phenylzinc iodide and 6-methylpyridylzinc bromide to give P2, P3 and P4. Spectral data tabulated (Table 5).

Example 13

Preparation of 5,7-dichloro-2-methylamino-8-hydroxyquinoline (PBT 1047) and 5,7-dichloro-2-(methyl-pyridin-2-yl-amino)-quinolin-8-ol (PBT 1056) (Scheme 13)

Scheme 13

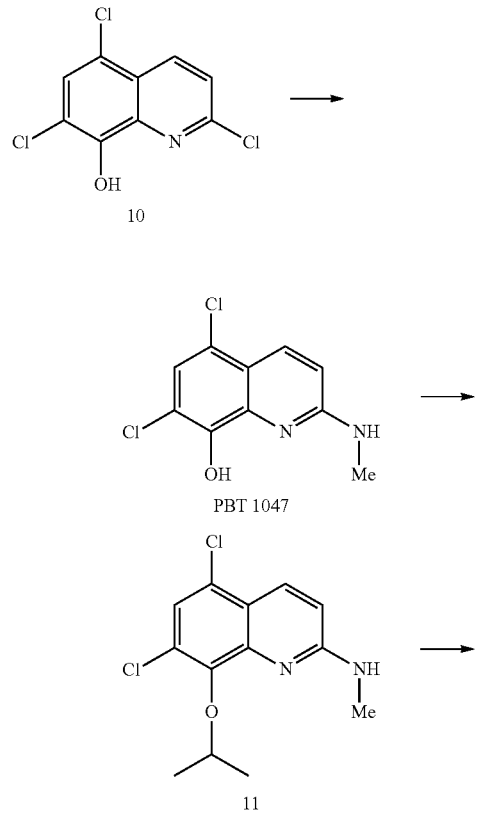

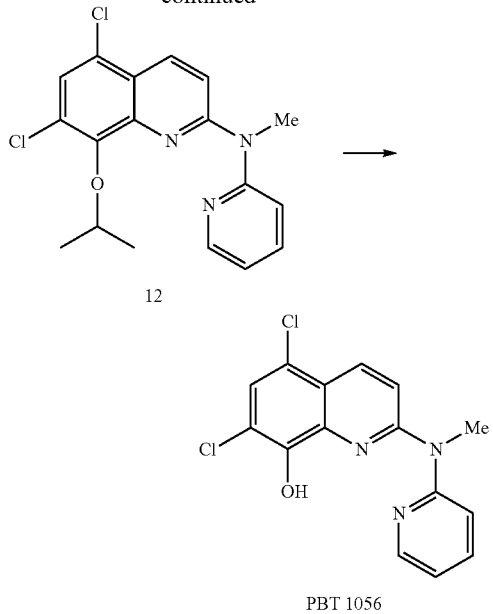

5,7-Dichloro-2-methylamino-8-hydroxyquinoline (PBT 1047)

2,5,7-Trichloro-8-hydroxyquinoline 10 (200 mg, 0.805 mmol) and a solution of methylamine in ethanol (12 mL of a 33% solution) were heated in a sealed vessel at 90° C. for 26 h, and cooled. The precipitate was then isolated via filtration and washed with diethyl ether. This provided pure 5,7-dichloro-2-methylamino-8-hydroxyquinoline (PBT 1047) as a pale yellow solid (186 mg, 95%). $^1$H NMR (DMSO-d$_6$, 400 MHz): δ 8.80 (br, 1H), 7.98 (d, J=9.1, 1H), 7.48 (br, 1H), 7.25 (s, 1H), 6.90 (d, J=9.1, 1H), 2.98 (d, J=4.8, 3 H); mass spectrum: m/z 243, 245 (M$^+$+1, 100 and 66%, respectively).

5,7-Dichloro-8-hydroxy-2-(methyl-pyridin-2-yl-amino)-quinoline (PBT 1056)

A solution of 5,7-dichloro-2-methylamino-8-hydroxyquinoline (1.02 g, 4.21 mmol), anhydrous potassium carbonate (2.4 g) and 2-bromopropane (0.6 mL) in dimethyl sulphoxide (10 mL) was stirred at RT for 2 days. Saturated ammonium chloride solution was added and the mixture was extracted with dichloromethane (30 mL×3). The extracts were combined, dried, and concentrated. The residue, after column chromatography (silica gel, dichloromethane), gave 5,7-dichloro-2-methylamino-8-isopropoxy-quinoline 11 as an off-white solid (938 mg, 78%). $^1$H NMR (CDCl$_3$): δ 8.13 (d, J=9.0, 1H), 7.28 (s, 1H), 6.69 (d, J=9.0, 1H), 5.10 (m, 1H), 4.90 (br, 1H), 3.11 (d, J=5.0, 3 H), 1.43 (s, 3H), 1.41 (s, 3H).

To a solution of 5,7-dichloro-2-methylamino-8-isopropoxy-quinoline 11 (200 mg, 0.701 mmol), racemic-BINAP (17.5 mg, 4 mol %), Pd$_2$(dba)$_3$ (12.8 mg, 2 mol %) and sodium tert-butoxide (78.6 mg, 0.818 mmol) in dry toluene (10 mL) under an argon atmosphere was added 2-bromopyridine (0.056 mL, 0.584 mmol). The orange-brown solution was then heated at 80° C. for 3 h. More 2-bromopyridine (0.010 mL, 0.104 mmol) was added and heating resumed for a further 2 h. The reaction mixture was quenched with saturated ammonium chloride, extracted with dichloromethane (20 mL×3), the extracts combined, dried, and concentrated.

The residue gave, after column chromatography (silica gel, dichloromethane/methanol (1:0-100:1), 5,7-dichloro-8-isopropoxy-2-(methyl-pyridin-2-yl-amino)-quinoline 12 as an off-white solid (175 mg, 69%). ¹H NMR (CDCl₃, 400 MHz): δ 8.47 (dd, J=1.7 and 5.0, 1H), 8.21 (d, J=9.3, 1H), 7.72 (m, 1H), 7.40 (s, 1H), 7.32 (m, 2H), 7.09 (dd, J=5.0 and 7.0, 1H), 5.14 (m, 1H), 3.80 (s, 3H), 1.41 (s, 3H), 1.40 (s, 3H).

The isopropyl ether 12 (171 mg, 0.472 mmol) was cleaved with boron trichloride according to the procedure of Example 8 to give, after methanol treatment, 5,7-dichloro-8-hydroxy-2-(methyl-pyridin-2-yl-amino)-quinoline as the hydrochloride (170 mg). Water (10 mL) was added and the pH of the mixture was adjusted to 8 with saturated NaHCO₃. The solid was then isolated via filtration. Subsequent column chromatography (silica gel, dichloromethane/methanol (9:1)) yielded the title compound (PBT 1056) as an off-white solid (140 mg, 93%). ¹H NMR (CD₃OD, 400 MHz): δ 8.43 (dd, J=2.0 and 5.0, 1H), 8.18 (d, J=9.4, 1H), 7.89 (ddd, J=2.0, 8.0 and 8.0, 1H), 7.41 (d, J=8.0, 1H), 7.35 (s, 1H), 7.27 (d, J=9.4, 1H), 7.25 (dd, J=5.0 and 8.0, 1H), 3.75 (s, 3H).

Example 14

Preparation of
5,7-dichloro-8-hydroxy-2-(2-pyridyl)quinoline
(Scheme 14)

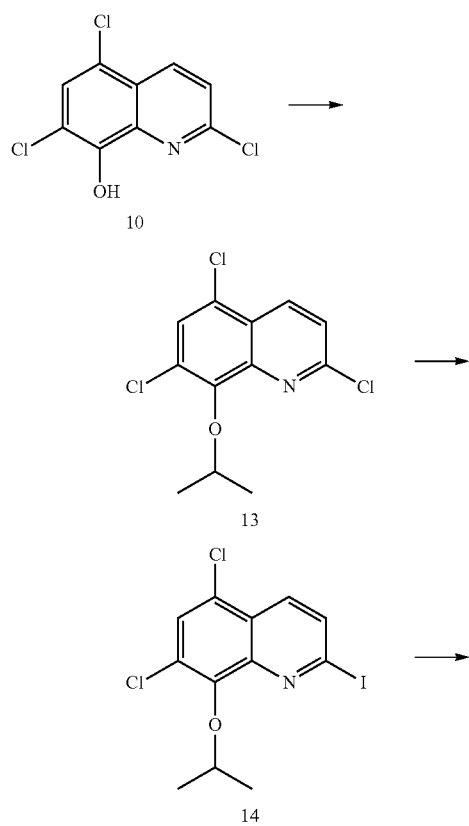

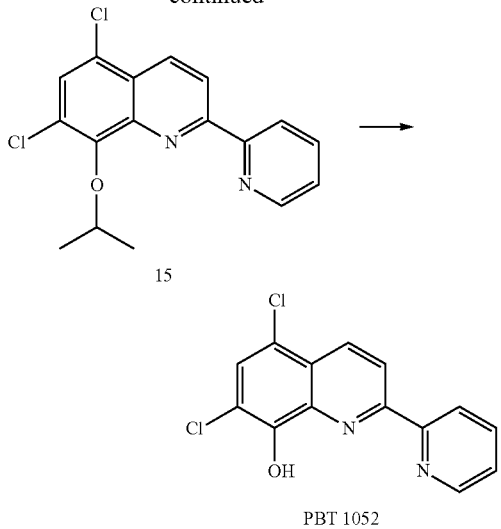

A mixture of 2,5,7-trichloro-8-hydroxyquinoline 10 (1.14 g, 4.61 mmol), 2-bromopropane (1.10 mL, 11.5 mmol) and anhydrous potassium carbonate (1.56 g, 11.5 mmol) in DMF (15 mL) was heated at 60° C. overnight. The mixture was then poured into water, extracted with ethyl acetate (20 mL×3), the extracts combined, and dried. Solvent removal gave a brown oil (3.15 g). Subsequent column chromatography (silica gel, ethyl acetate/hexane (1:9)) afforded 2,5,7-trichloro-8-isopropoxy-quinoline 13 as a white solid (1.15 g, 87%), m.p. 83-85° C. ¹H NMR (CDCl₃, 200 MHz): δ 8.43 (d, J=10, 1H), 7.64 (s, 1H), 7.45 (d, J=10, 1H), 5.15 (m, 1H), 1.46 (s, 3H), 1.42 (s, 3H).

A mixture of 2,5,7-trichloro-8-isopropoxy-quinoline 13 (5.93 g, 20.5 mmol), sodium iodide (12.3 g, 82 mmol) and acetyl chloride (1.4 mL, 20 mmol) in acetonitrile (30 mL) was heated under reflux overnight. The mixture was then poured into water and extracted with ethyl acetate (30 mL×3). The combined extracts was washed with 10% sodium thiosulphate solution, water, brine, dried with magnesium sulphate and concentrated to give an orange solid (6.9 g). Purification via column chromatography (silica gel, ethyl acetate/hexanes (1:19)) gave the iodide, 5,7-dichloro-2-iodo-8-isopropoxy-quinoline 14, as a white solid (4.57 g, 58%), m.p. 97-99° C. ¹H NMR (CDCl₃, 200 MHz): δ 8.05 (d, J=8.6, 1H), 7.80 (d, J=8.6, 1H), 7.62 (s, 1H), 5.02 (m, 1H), 1.45 (s, 3H), 1.42 (s, 3H).

Palladium chloride bis(triphenylphosphine) (362 mg, 0.51 mmol) was added to a stirred solution of 5,7-dichloro-2-iodo-8-isopropoxy-quinoline 14 (2.80 g, 7.35 mmol) in anhydrous THF (150 mL) at room temperature under an atmosphere of nitrogen. 2-Pyridylzinc bromide (29.4 mL of a 0.5 M solution in THF, 14.7 mmol) was then added dropwise over 15 minutes and the mixture was stirred at RT for 2 h. Saturated ammonium chloride was added and the mixture extracted with ethyl acetate (30 mL×3), the combined extracts dried, and concentrated. The residue afforded, after column chromatography (silica gel, ethyl acetate/hexanes (1:9)), 5,7-dichloro-8-isopropoxy-2-(2-pyridyl)quinoline 15 as a white solid (1.83 g, 75%), m.p. 112-114° C. ¹H NMR (DMSO-d₆, 200 MHz): δ 8.78-8.58 (m, 4H), 7.85 (m, 1H), 7.64 (s, 1H), 7.39 (m, 1H), 5.25 (m, 1H), 1.52 (s, 3H), 1.50 (s, 3H).

Boron trichloride (27 mL of a 1 M solution in dichloromethane, 27.6 mmol) was added dropwise to a solution of 5,7-dichloro-8-isopropoxy-2-(2-pyridyl)quinoline 15 (1.83 g, 5.51 mmol) in dichloromethane (30 mL) at 0° C. under an atmosphere of nitrogen. The mixture was stirred at 0° C. for 1 h and then allowed to warm to RT. After 24 h, some starting material was still present (by TLC analysis). More boron trichloride (14 mL) was added and stirring resumed for a further 4 h. The reaction was quenched with methanol (10 mL) and the volatiles removed in vacuo. The process was repeated until the residue reached constant weight. This gave 5,7-dichloro-8-hydroxy-2-(2-pyridyl)quinoline as the hydrochloride salt. The hydrochloride salt (1.68 g) and water (20 mL) was then treated with saturated sodium bicarbonate until the pH of the solution was 8. The mixture was the extracted with ethyl acetate (30 mL×3) and dried. The residue obtained after solvent removal was washed with methanol. This provided 5,7-dichloro-8-hydroxy-2-(2-pyridyl)quinoline (PBT 1052) as an off-white solid (1.25 g, 78%), m.p.>230° C. $^1$H NMR (DMSO-$d_6$, 200 MHz): δ 10.8 (br, 1H), 9.21 (d, J=9, 1H), 8.30-8.62 (m, 3H), 8.12 (m, 1H), 7.88 (s, 1H), 7.62 (m, 1H).

Example 15

Preparation of 5,7-dichloro-2-dimethylaminomethyl-quinolin-8-ol hydrochloride (PBT 1033) (Scheme 15)

$^1$H NMR (CDCl$_3$, 400 MHz): δ 10.26 (s, 1H), 8.69 (d, J=8.8, 1H), 8.37 (br, 1H), 8.17 (d, J=8.8, 1H), 7.76 (s, 1H).

5,7-Dichloro-2-dimethylaminomethyl-quinolin-8-ol hydrochloride (PBT 1033)

Triethylamine (0.55 mL) was added dropwise to a stirred solution of 5,7-dichloro-8-hydroxyquinoline-2-carboxaldehyde 17 (1.0 g, 4.13 mmol) and dimethylamine hydrochloride (365 mg, 4.48 mmol) in 1,2-dichloroethane (50 mL). After 5 minutes, sodium triacetoxyborohydride (1.2 g, 5.66 mmol) was added portionwise over 5 minutes. The mixture was then allowed to stir at RT overnight. Dichloromethane (100 mL) was added, the mixture washed with saturated sodium bicarbonate (50 mL×3), dried (Na$_2$SO$_4$), and concentrated. The resulting residue was extracted with diethyl ether (50 mL×4), the ethereal extracts combined and concentrated. Concentrated hydrochloric acid (5 mL) was then added and the mixture concentrated in vacuo. The process was repeated twice. The residue, after washing with dichloromethane, gave 5,7-dichloro-2-dimethylaminomethyl-quinolin-8-ol hydrochloride (PBT 1033) as a pale straw-coloured solid (0.96 g, 73%). $^1$H NMR (DMSO-$d_6$, 400 MHz): δ 10.80 (s, 1H), 10.40 (br, 1H), 8.60 (d, J=8.6, 1H), 7.92 (s, 1H), 7.78 (d, J=8.6, 1H), 4.83 (d, J=5.3, 2H), 2.94 (s, 3H), 2.92 (s, 3H).

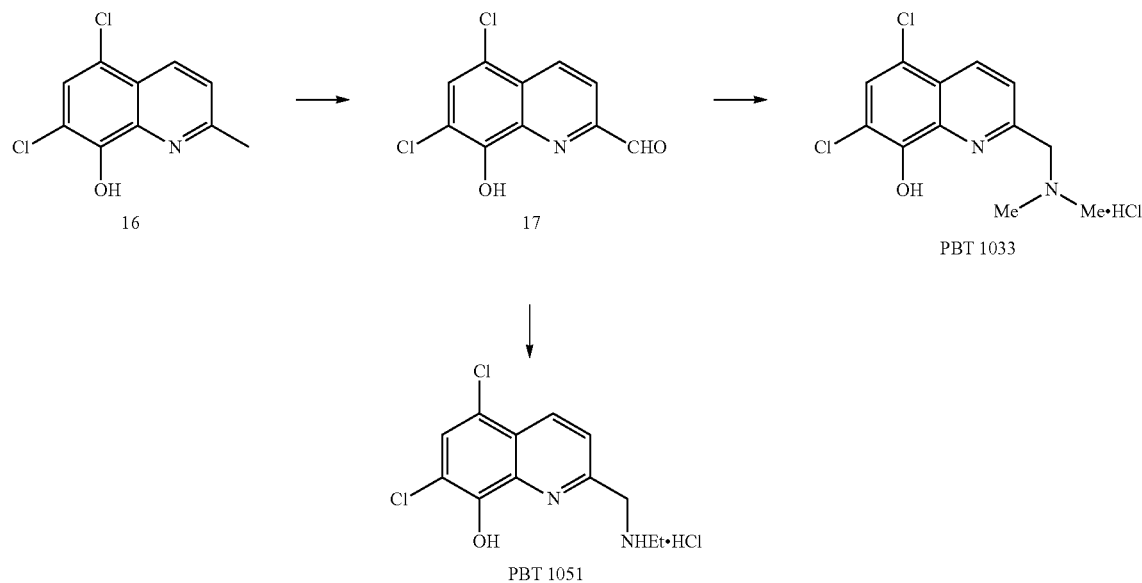

Scheme 15

5,7-Dichloro-8-hydroxyquinoline-2-carboxaldehyde 17

A solution of 5,7-dichloro-2-methyl-quinolin-8-ol 16 (1.5 g, 6.58 mmol) in 1,4-dioxane (20 mL) was added dropwise over 3 h to a stirred suspension of selenium dioxide (1.3 g, 11.72 mmol) in 1,4-dioxane (60 mL) at 50-55° C. The resulting mixture was then heated at 80° C. overnight, cooled, and the solids filtered off (celite). The filtrate was concentrated and the residue, after washing with diethyl ether (10 mL×3), gave 17 as a yellow solid (quantitative yield). This material was used in the subsequent step without further purification.

Preparation of 5,7-dichloro-2-ethylaminomethyl-quinolin-8-ol hydrochloride (PBT 1051) (Scheme 15)

The procedure described in Example 15 was repeated on 5,7-dichloro-8-hydroxyquinoline-2-carboxaldehyde 17 (1.00 g, 4.13 mmol) substituting dimethylamine hydrochloride with ethylamine hydrochloride. This provided 5,7-dichloro-2-ethylaminomethyl-quinolin-8-ol hydrochloride (PBT 1051) as a pale straw-coloured solid (0.60 g, 47%). $^1$H NMR (DMSO-$d_6$): δ 9.40 (br, 2H), 8.59 (d, J=8.8, 1 H), 7.90 (s, 1H), 7.76 (d, J=8.8, 1H), 4.64 (s, 2H), 3.14 (q, J=7.2, 2 H), 1.32 (t, J=7.2, 3H).

Example 16

Preparation of 5,7-dichloro-8-hydroxy-quinoline-2-carboxylic acid [2-(1H-imidazol-4-yl)-ethyl]-amide (PBT 1038) (Scheme 16)

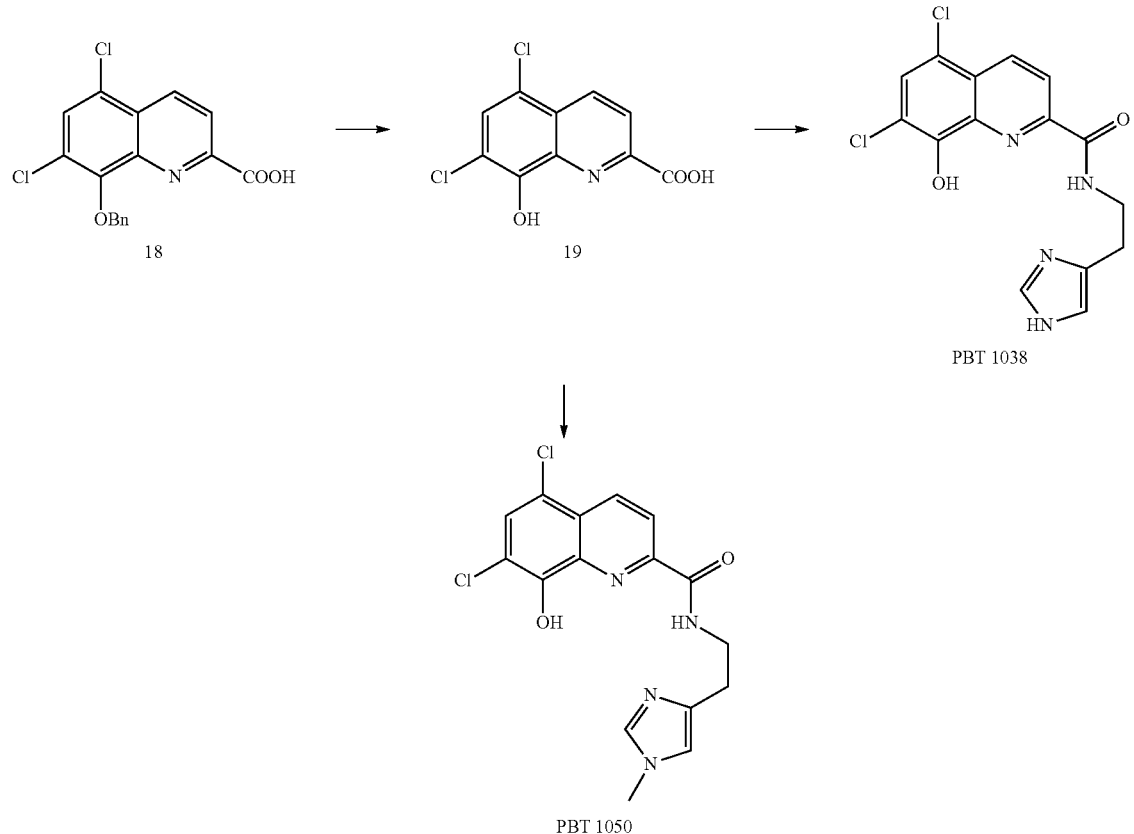

Scheme 16

PBT 1038

PBT 1050

5,7-Dichloro-8-hydroxyquinoline-2-carboxylic acid 19

A mixture of 5,7-dichloro-8-benzyloxy-quinoline-2-carboxylic acid 18 (2.56 g, 7.35 mmol) and concentrated hydrochloric acid (25 mL) was stirred at RT for 48 h, and then concentrated to dryness. The resulting residue was washed with diethyl ether (20 mL×2). This provided 5,7-dichloro-8-hydroxyquinoline-2-carboxylic acid 19 as a yellow solid (1.78 g, 94%). $^1$H NMR (CDCl$_3$/DMSO-d$_6$ (19:1), 400 MHz): δ 10.60 (br, 1H), 8.53 (d, J=8.8, 1H), 8.22 (d, J=8.8, 1H), 7.60 (s, 1H).

5,7-Dichloro-8-hydroxyquinoline-2-carboxylic acid [2-(1H-imidazol-4-yl)-ethyl]-amide (PBT 1038)

According to the procedure described in Example 1, 5,7-dichloro-8-hydroxyquinoline-2-carboxylic acid 19 (597 mg, 2.31 mmol), dicyclohexylcarbodiimide (483 mg, 2.31 mmol), 1-hydroxybenzotriazole hydrate (316 mg, 2.31 mmol), histamine dihydrochloride (425 mg, 2.31 mmol) and triethylamine (0.5 mL) gave, after column purification (silica gel, ethyl acetate/isopropanol/water (12:4:1)), 5,7-dichloro-8-hydroxyquinoline-2-carboxylic acid [2-(1H-imidazol-4-yl)-ethyl]-amide (PBT 1038) as a pale straw-coloured solid (276 mg, 34%). $^1$H NMR (DMSO-d$_6$, 400 MHz): δ 11.40 (br, 2H), 9.74 (m, 1H), 8.64 (d, J=8.6, 1H), 8.28 (d, J=8.6, 1H), 7.92 (s, 1H), 7.53 (s, 1H), 6.83 (s, 1H), 3.59 (m, 2H), 2.81 (m, 2H).

Preparation of 5,7-dichloro-8-hydroxyquinoline-2-carboxylic acid [2-(1-methyl-1H-imidazol-4-yl)-ethyl]-amide (PBT 1050) (Scheme 16)

Following the procedure of Example 1, 5,7-dichloro-8-hydroxyquinoline-2-carboxylic acid 19 (1.00 g, 3.88 mmol) was treated with dicyclohexylcarbodiimide (0.96 g, 4.60 mmol), 1-hydroxybenzotriazole hydrate (0.53 g, 5.20 mmol), 1-methyl-1H-histamine hydrochloride (1.24 g, 7.67 mmol) and triethylamine (0.65 mL) for 24 h. The solid was isolated via filtration and dissolved in hot methanol. Upon cooling, this provided 5,7-dichloro-8-hydroxy-quinoline-2-carboxylic acid [2-(1-methyl-1H-imidazol-4-yl)-ethyl]-amide (PBT 1050) as colourless needles (0.99 g, 70%). $^1$H NMR (DMSO-d$_6$, 400 MHz): δ 10.25 (s, 1H), 9.10 (m, 1H), 8.14 (s, 1H), 7.83 (d, J=8.6, 1H), 7.44 (d, J=8.6, 1H), 7.12 (s, 1H), 6.68 (s, 1H), 2.95 (s, 3H), 2.85 (m, 2H), 2.15 (m, 2H).

Example 17

Preparation of 7-chloro-5-(pyridin-3-yl)-quinolin-8-ol (PBT 1057) (Scheme 17)

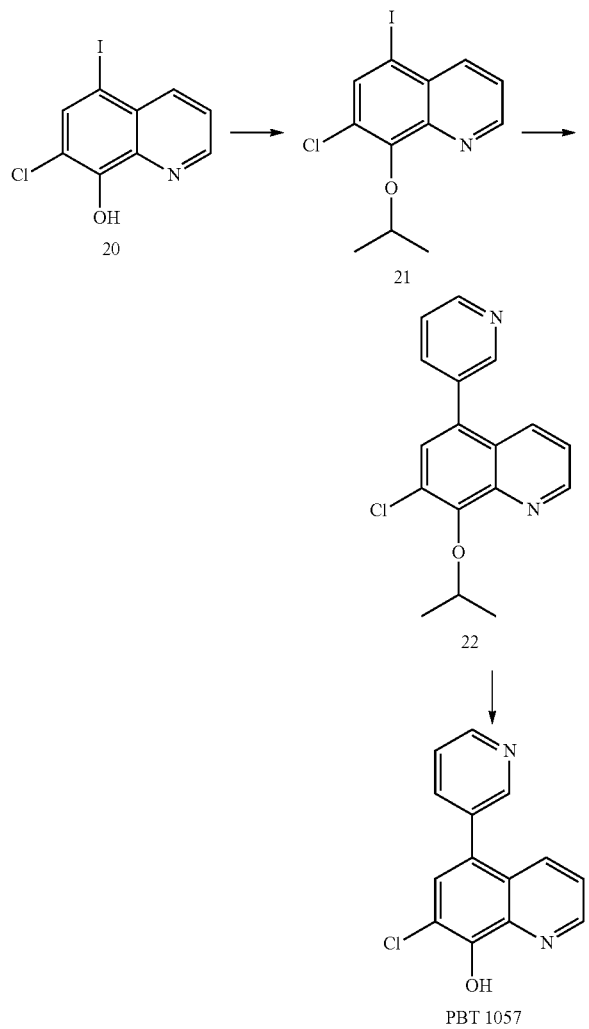

Following the procedure described in Example 8, 7-chloro-5-iodo-8-hydroxy-quinoline 20 and 2-bromopropane gave 7-chloro-5-iodo-8-isopropoxy-quinoline 21 (80%). $^1$H NMR (CDCl$_3$/DMSO-d$_6$ (19:1), 400 MHz): δ 9.09 (m, 1H), 8.55 (m, 1H), 8.10 (s, 1H), 7.63 (m, 1H), 5.15 (m, 1H), 1.49 (s, 3H), 1.47 (s, 3H).

A mixture of 21 (180 mg, 0.518 mmol), 3-pyridylboronic acid (76 mg, 0.622 mmol), KF (60 mg, 1.04 mmol), Pd(Ph$_3$P)$_4$ (10 mg) and toluene-water (1:1, 10 mL) was heated under reflux under an argon atmosphere for 16 h. The mixture was cooled, quenched with saturated ammonium chloride, extracted with dichloromethane (10 mL×3), the extracts combined, dried, and concentrated. The residue gave, after column chromatography (silica gel, dichloromethane/methanol (40:1)), 7-chloro-5-(pyridin-3-yl)-8-isopropoxyquinoline 22 as a pale cream solid (20 mg, 14%); 132 mg of starting material was also recovered. 22: $^1$H NMR (CDCl$_3$, 400 MHz): δ 9.00 (m, 1H), 8.08 (m, 1H), 7.93 (d, J=7.7, 1H), 7.70-7.56 (m, 2H), 7.55 (s, 1H), 7.50-7.42 (m, 2H), 5.23 (m, 1H), 1.49 (s, 3H), 1.48 (s, 3H).

Cleavage of the isopropyl ether 22 (20 mg, 0.07 mmol) with boron trichloride following the method outlined in Example 8, gave 7-chloro-5-(pyridin-3-yl)-quinolin-8-ol (PBT 1057) as a pale straw-coloured solid (17 mg, 94%). $^1$H NMR (CD$_3$OD, 400 MHz): δ 9.16 (m, 2H), 9.04 (d, J=5.8, 1H), 8.93 (dd, J=1.2 and 8.6, 1 H), 8.84 (m, 1H), 8.30 (dd, J=5.8 and 8.1, 1H), 8.09 (s, 1H), 8.08 (dd, J=5.1 and 8.6, 1H).

Example 18

Preparation of 3,5,7-trichloro-8-hydroxyquinoline (PBT 1058) (Scheme 18)

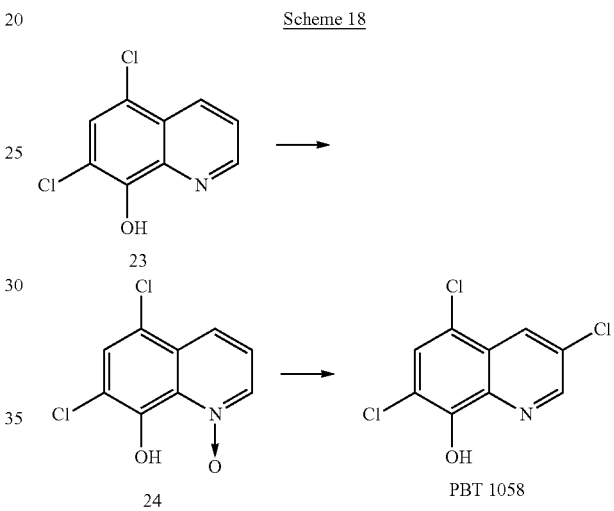

m-Chloroperbenzoic acid (3.10 g of a 70% reagent, 26 mmol) was added portionwise to a stirred solution of 5,7-dichloro-8-hydroxyquinoline 23 (5.00 g, 23 mmol) in chloroform (150 mL) at 0° C. After 1 h, the mixture was warm to RT and allowed to stir for a further 48 h. The mixture was concentrated and the residue partitioned between ethyl acetate and 1 N NaHCO$_3$ (200 mL, 1:1); some of the 1-N-oxide 24 remained as a precipitate and was isolated via filtration. The filtrate was then extracted with ethyl acetate (40 mL×3), the extracts combined, dried, and concentrated to give more 1-N-oxide 24. A total of 4.76 g (90%) of 1-N-oxide 24 was obtained. $^1$H NMR (DMSO-d$_6$, 400 MHz): δ 8.74 (d, J=5.9, 1H), 8.24 (d, J=8.8, 1H), 8.02 (s, 1H), 7.70 (dd, J=5.9 and 8.8, 1H).

A solution of 24 (2.01 g, 8.8 mmol) and phosphorus oxychoride (40 mL) was heated under reflux for 18 h. Excess phosphorus oxychoride was removed in vacuo, concentrated hydrochloric acid (80 mL) was added, the solution heated under reflux for 2 h, and cooled. The mixture was then poured into ice and aqueous ammonia, adjusting the pH to 8. The precipitate was isolated via filtration and washed with water. This material was then dissolved in dichloromethane and successively filtered through short pads of silica gel and celite. The solvent was removed providing 3,5,7-trichloro-8-hydroxy-quinoline (PBT 1058) as an off-white solid (0.92 g, 42%), m.p. 144-147° C. (lit. (Gershon et al, 1999) 159-160°

C.). $^1$H NMR (CD$_3$OD): δ 8.85 (d, J=2.2, 1H), 8.53 (d, J=2.2, 1H), 7.71 (s, 1H); mass spectrum: m/z 248, 250, 252 (M$^+$+1, 100, 100 and 33%, respectively).

Example 19

Preparation of 3-amino-5,7-dichloro-8-hydroxyquinoline (PBT 1060) (Scheme 19)

Scheme 19

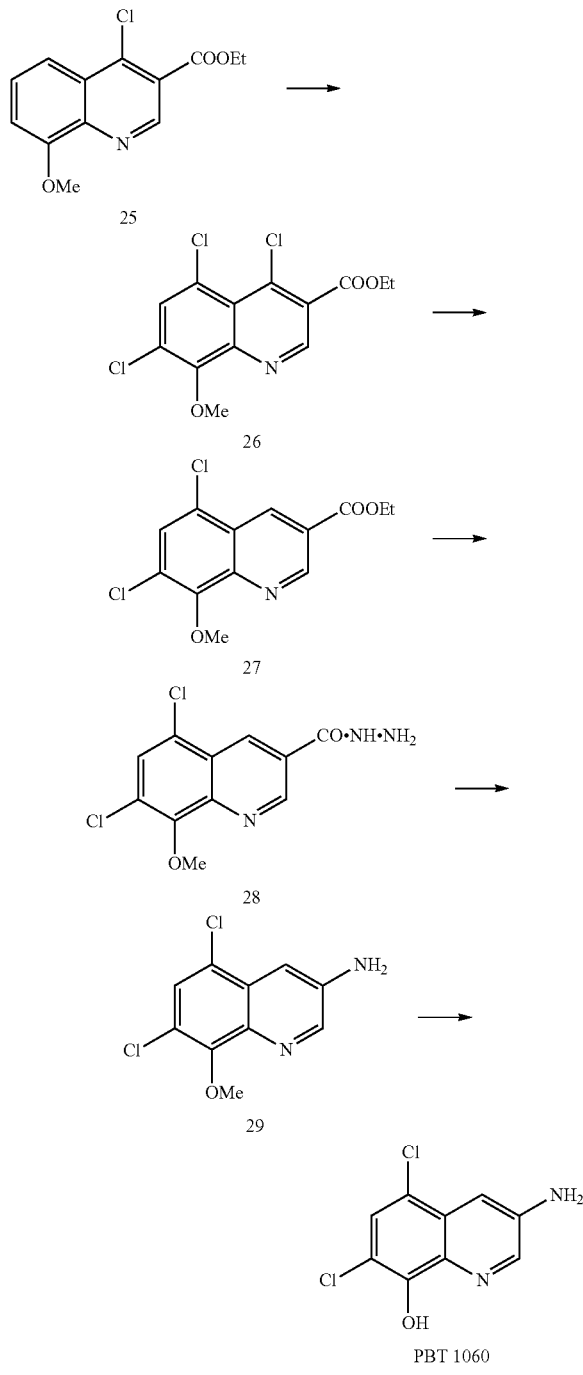

4,5,7-Trichloro-8-methoxy-quinoline-3-carboxylic acid ethyl ester 26

To a stirred solution of 4-chloro-8-methoxy-quinoline-3-carboxylic acid ethyl ester (1.00 g, 3.76 mmol) in chloroform (50 mL) was added, dropwise over 1 h, a solution of sulfuryl chloride (15 mL) in chloroform (15 mL) whilst maintaining the temperature at 25-30° C. The solution was then heated at 60-70° C. for 48 h. During this time, further sulfuryl chloride (2 mL) was added at regular intervals (2, 24 and 30 h). The solution was allowed to cool to RT and added to ice-aqueous ammonia, adjusting the pH to 8. The mixture was then extracted with dichloromethane (20 mL×3), the extracts combined and concentrated. Column chromatography (silica gel, dichloromethane/methanol (100:1)) gave the title compound 26 as a cream solid (0.36 g, 29%). $^1$H-NMR (CDCl$_3$, 400 MHz): δ 9.04 (s, 1H), 7.78 (s, 1H), 4.51 (q, J=7.1, 2 H), 4.14 (s, 3H), 1.46 (t, J=7.1, 3 H).

5,7-Dichloro-8-methoxy-quinoline-3-carboxylic acid ethyl ester 27

A suspension of zinc powder (0.70 g) was stirred at 20° C. in a solution of 4,5,7-trichloro-8-methoxy-quinoline-3-carboxylic acid ethyl ester 26 (364 mg, 1.09 mmol) and acetic acid (2.2 ml) in 1,4-dioxane (15 ml). After 20 minutes, ethyl acetate (20 ml) was added and the resultant mixture filtered through a pad of celite. The filtrate was washed with saturated aqueous sodium chloride solution (10 ml), dried (MgSO$_4$), filtered, and the solvent removed under vacuum. The residue was chromatographed on flash silica (ethyl acetate/hexane, 1:9), yielding 130 mg (39%) of the title compound 27 as a white solid. $^1$H NMR (CDCl$_3$, 400 MHz): δ 9.51 (d, J=2.0, 1H), 9.15 (d, J=2.0, 1H), 7.72 (s, 1H), 4.51 (q, J=7.2, 2 H), 4.18 (s, 3H), 1.47 (t, J=7.2, 3 H).

5,7-Dichloro-8-methoxy-quinoline-3-carboxylic acid hydrazide 28

A solution of 5,7-dichloro-8-methoxy-quinoline-3-carboxylic acid ethyl ester 27 (404 mg, 1.35 mmol) and hydrazine monohydrate (1.0 g) in ethanol (10 ml) was heated under reflux for 5 hours. Upon cooling, a white crystalline solid was deposited. This was isolated via filtration, washed with ethanol, and dried, yielding the hydrazide 28 (307 mg, 80%) as a white solid. $^1$H-NMR (DMSO-d$_6$, 400 MHz): δ 10.32 (br, 1H), 9.33 (d, J=2.4, 1H), 8.89 (d, J=2.4, 1H), 8.02 (s, 1H), 4.66 (br, 2H), 4.06 (s, 3H).

3-Amino-5,7-dichloro-8-methoxy-quinoline 29

Sodium nitrite (180 mg, 2.61 mmol) was added at 0° C. to a stirred suspension of 5,7-dichloro-8-methoxy-quinoline-3-carboxylic acid hydrazide 28 (248 mg, 0.87 mmol) in 1 M hydrochloric acid (2 ml), acetic acid (5 ml) and water (20 ml). Stirring was continued at 00 for 1 h, the ice bath removed and upon warming to RT, the heterogeneous mixture was heated under reflux. The mixture became homogeneous after about 30 minutes and heating was continued for a total of 6 h. Upon cooling, the volatiles were removed under vacuum and the residue partitioned between ethyl acetate (20 ml) and 10% aqueous ammonia solution (10 ml). The layers were separated and the aqueous layer washed with more ethyl acetate (5 ml×2). The combined ethyl acetate layers were dried (Na$_2$SO$_4$), filtered and the ethyl acetate removed under vacuum. The residue gave, after flash chromatography (ethyl acetate/hexane, 1:1), the title compound 29 (106 mg, 50%) as a white solid. ¹H-NMR (DMSO-d₆, 400 MHz): δ 8.48 (d, J=2.4, 1H), 7.63 (s, 1H), 7.28 (d, J=2.4, 1H), 6.16 (br, 2H), 3.97 (s, 3H).

3-Amino-5,7-dichloro-quinolin-8-ol

Boron tribromide (2.0 ml of a 1 M solution in dichloromethane, 2.0 mmol) was added to a stirred suspension of 3-amino-5,7-dichloro-8-methoxy-quinoline (104 mg, 0.43 mmol) in dichloromethane (10 ml) at −30° C. Stirring was continued for 14 h with the cold bath being allowed to reach RT. The mixture was then cooled to 0° C. and water (1 ml) added. The dichloromethane was then removed and ethyl acetate (10 ml) and more water (5 ml) were added. The yellow precipitate that formed was collected by filtration and dried to give 74 mg of a mixture of starting material and product (NMR analysis). The ethyl acetate layer from the filtrate was dried (Na₂SO₄), filtered, and the solvent removed under vacuum to yield 42 mg of solid which was also a mixture of starting material and product (NMR analysis). The two solid samples were combined and the components separated by flash chromatography (ethyl acetate/2-propanol, 1:0-3:1). This provided title compound as the hydrobromide (30 mg), and recovered starting material (57 mg). To a mixture of 3-amino-5,7-dichloro-quinolin-8-ol hydrobromide and water (10 mL) was added saturated NaHCO₃ until the pH was 8. The solid was isolated yielding the title compound (PBT 1060) as a cream solid (25 mg, 26%). ¹H-NMR (DMSO-d₆, 400 MHz): δ 8.15 (br, 1H), 7.24 (br, 1H), 7.14 (br, 1H), 5.70 (br, 2H); mass spectrum: m/z 229, 231 (M⁺+1, 100 and 66%, respectively). 3-Amino-5,7-dichloro-quinolin-8-ol hydrobromide: ¹H-NMR (CD₃OD, 400 MHz): δ 8.43 (d, J=2.6, 1H), 7.46 (d, J=2.6, 1H), 7.42 (s, 1H).

TABLE 1

Data for Examples 1 and 2.

| Product ID | Method of preparation[a] | Product | Yield (%) | ¹H NMR data | Mass spectral data |
|---|---|---|---|---|---|
| A1 | A | 8-hydroxyquinoline-2-carboxamide with 2-(1H-imidazol-4-yl)ethyl group | 52 | (CDCL3/DMSO-d₆, 19:1): δ 9.81 (m, 1 H), 8.30-8.23 (m, 2 H), 7.91 (d, J = 9.0, 1 H), 7.86 (s, 1 H), 7.68 (d, J = 9.0, 1 H), 7.51 (m, 1 H), 7.36 (m, 1 H), 7.19 (d, J = 4.0, 1 H), 6.94 (s, 1 H), 3.80 (m, 2 H), 3.03 (m, 2 H) | |
| A2 | A | 8-hydroxyquinoline-2-carboxamide with 2-(pyridin-2-yl)ethyl group | 85 | (CDCl₃): δ 9.61 (m, 1 H), 8.60 (d, J = 5.4, 1 H), 8.27-8.18 (m, 2 H), 8.03 (m, 1 H), 7.93 (d, J = 8.0, 1 H), 7.77 (d, J = 8.3, 1 H), 7.63 (d, J = 8.0, 1 H), 7.51 (d, J = 8.0, 1 H), 7.35 (d, J = 8.0, 1 H), 7.24 (m, 1 H), 3.90 (m, 2 H), 3.42 (m, 2 H) | 294 (M⁺ + 1) |
| A3 | A | 8-hydroxyquinoline-2-carboxamide with thiazol-2-yl group | 65 | (CDCl₃): δ 9.53 (m, 1 H), 8.42-8.25 (m, 2 H), 7.65-7.25 (m, 6 H) | 272 (M⁺ + 1) |
| A4 | A | 8-hydroxyquinoline-2-carboxamide with 5-methylthiazol-2-yl group | 81 | (CDCl₃/DMSO-d₆, 19:1): δ 10.35 (br, 1 H), 8.38-8.29 (m, 2 H), 7.58 (m, 1 H), 7.48 (s, 1 H), 7.40 (d, J = 8.3, 1 H), 7.27-7.20 (m, 2 H), 2.48 (s, 3 H) | 286 (M⁺ + 1) |

TABLE 1-continued

Data for Examples 1 and 2.

| Product ID | Method of preparation[a] | Product | Yield (%) | $^1$H NMR data | Mass spectral data |
|---|---|---|---|---|---|
| A5 | A | 8-hydroxyquinoline-2-carboxamide with N-(pyridin-2-ylmethyl) group | 81 | (CDCl$_3$: δ 10.54 (t, J = 4.0, 1 H), 8.72 (br, 1 H), 8.63 (d, J = 5.6, 1 H), 8.30-8.18 (m, 2 H), 7.9 (d, J = 7.8, 1 H), 7.64-7.30 (m, 5 H), 5.10 (m, 2 H) | 280 (M$^+$ + 1) |
| A6 | A | 8-hydroxyquinoline-2-carboxamide with 2-hydroxyphenyl group | 65 | (CDCl$_3$/DMSO-d$_6$, 19:1): δ 11.34 (br, 1 H), 8.36 (s, 1 H), 7.59 (m, 1 H), 7.56 (d, J = 9.0, 1 H), 7.41 (d, J = 9.0, 1 H), 7.23 (d, J = 4.0, 1 H), 7.19 (d, J = 4.0, 1 H), 7.09 (m, 1 H), 6.96 (m, 1 H), 5.00 (br, 2 H) | |
| A7 | A | 8-hydroxyquinoline-2-carboxamide with 2-aminoethyl group | 71 | (CDCl$_3$/DMSO-d$_6$, 19:1): δ 10.16 (m, 1 H), 8.60 (br, 1 H), 8.25 (m, 1 H), 7.92 (d, J = 7.8, 1 H), 7.67 (d, J = 7.8, 1 H), 7.57-7.35 (m, 2 H), 5.20 (br, 2 H), 3.89 (m, 2 H), 2.60 (m, 2 H) | |
| A8 | A | 8-hydroxyquinoline-2-carboxamide with carboxymethyl group | 62 | (CDCl$_3$/DMSO-d$_6$, 19:1): δ 10.35 (m, 1 H), 8.37 (s, 1 H), 7.81 (m, 1 H), 7.59-7.39 (m, 2 H), 4.23 (m, 2 H), 3.60 (br, 2 H) | |
| A9 | B | 8-hydroxyquinoline-2-carboxamide with (thiazol-2-ylmethyl) group | 60 | (CDCl$_3$): δ 9.01 (m, 1 H), 8.31 (m, 1 H), 8.25 (br, 1 H), 7.77 (d, J = 3.4, 1 H), 7.55 (dd, J = 8.0 and 8.0, 1 H), 7.40 (d, J = 8.0, 1 H), 7.33 (d, J = 3.4, 1 H), 7.27 (m, 1 H), 7.24 (d, J = 7.3, 1 H), 5.05 (m, 2 H) | 286 (M$^+$ + 1) |

TABLE 1-continued

Data for Examples 1 and 2.

| Product ID | Method of preparation[a] | Product | Yield (%) | 1H NMR data | Mass spectral data |
|---|---|---|---|---|---|
| A10 | B | (structure: 8-hydroxyquinoline-2-carboxamide N,N-bis(pyridin-2-ylmethyl)) | 63 | (CDCl$_3$): δ 9.60 (br, 1 H), 8.75 (d, J = 4.2, 1 H), 8.58 (d, J = 4.5, 1 H), 8.28 (d, J = 8.6, 1 H), 8.08 (d, J = 8.6, 1 H), 7.77 (m, 1 H), 7.68 (m, 1 H), 7.58-7.15 (m, 7 H) | 371 (M$^+$ + 1) |
| B1 | A | (structure: 4,8-dihydroxyquinoline-2-carboxamide with histamine) | 77 | (CDCl$_3$/DMSO-d$_6$, 19:1): δ 9.60 (m, 1 H), 8.29 (s, 1 H), 7.91 (d, J = 8.3, 1 H), 7.68-7.65 (d, J = 9.0, 1 H), 7.50-7.29 (m, 2 H), 7.15-7.07 (m, 2 H), 3.40 (m, 2 H), 3.30 (br, 2 H), 3.10 (m, 2 H). | |
| B2 | A | (structure: 4,8-dihydroxyquinoline-2-carboxamide N-(pyridin-2-ylmethyl)) | 31 | (CDCl$_3$/DMSO-d$_6$, 19:1): δ 10.11 (m, 1 H), 9.55 (br, 1 H), 8.63 (d, J = 4.4, 1 H), 7.95 (m, 1 H), 7.70-7.65 (m, 2 H), 7.58 (s, 1 H), 7.45 (m, 1 H), 7.38-7.34 (m, 2 H), 7.14 (m, 1 H), 4.96 (m, 2 H) | |
| B3 | A | (structure: 4,8-dihydroxyquinoline-2-carbonyl glycine) | 78 | (CDCl$_3$/DMSO-d$_6$, 19:1): δ 10.35 (m, 1 H), 8.37 (s, 1 H), 7.81 (m, 1 H), 7.59-7.39 (m, 2 H), 4.23 (m, 2 H), 3.60 (br, 2 H) | |
| B4 | A | (structure: 4,8-dihydroxyquinoline-2-carboxamide N-(2-aminophenyl)) | 97 | (CDCl$_3$/DMSO-d$_6$, 19:1): δ 10.99 (br, 1 H), 9.63 (br, 1 H), 7.77 (s, 1 H), 7.69 (d, J = 8.5, 1 H), 7.50-7.32 (m, 3 H), 7.18-7.05 (m, 2 H), 6.85-6.78 (m, 2 H), 4.20 (br, 2H) | 296 (M$^+$ + 1) |

TABLE 1-continued

Data for Examples 1 and 2.

| Product ID | Method of preparation[a] | Product | Yield (%) | $^1$H NMR data | Mass spectral data |
|---|---|---|---|---|---|
| B5 | A | 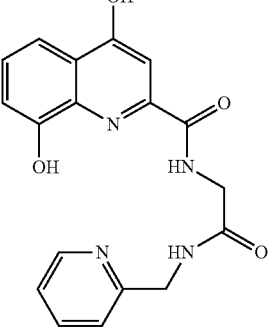 | 51 | (CDCl$_3$/DMSO-d$_6$, 9:1): δ 10.02 (m, 1 H), 8.49 (s, 1 H), 7.95 (m, 1 H), 7.72-7.60 (m, 3 H), 7.22-7.10 (m, 4 H), 4.57 (m, 2 H), 4.22 (m, 2 H), 3.20 (br, 2 H) | 352 (M$^+$ + 1) |
| B6 | A | 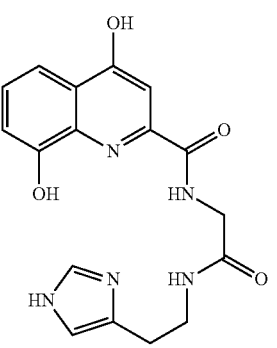 [SMILES: O=C(CNC(=O)c1cc(O)c2cccc(O)c2n1)NCCc1c[nH]cn1] | 47 | (CDCl$_3$/DMSO-d$_6$, 19:1): δ 9.92 (m, 1 H), 7.67 (d, J = 8.8, 1 H), 7.53 (m, 1 H), 7.50-7.30 (m, 4 H), 7.12 (d, J = 8.0, 1 H), 6.76 (s, 1 H), 4.09 (m, 2 H), 3.48 (m, 2 H), 2.60 (m, 2 H) | 390 (M$^+$ + 1) |
| C1 | | 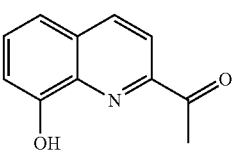 | 98 | (CDCl$_3$): δ 8.31 (d, J = 9.0, 1 H), 8.18 (d, J = 9.0, 1 H), 8.15 (br, 1 H), 7.60 (dd, J = 9.0 and 9.0, 1 H), 7.42 (d, J = 9.0, 1 H), 7.28 (d, J = 9.0, 1 H), 2.88 (s, 3 H) | |

[a]See Experimental Section: A = General Procedure A; B = General Procedure B.

TABLE 2

Data for Examples 3, 4, 5 and 6

| Product ID | Product | Yield (%) | $^1$H NMR data | Mass spectral data |
|---|---|---|---|---|
| D1 | 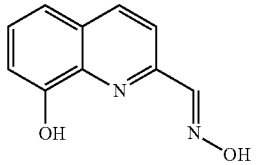 [SMILES: O/N=C/c1ccc2cccc(O)c2n1] | 80 | (CDCl$_3$/DMSO-d$_6$, 19:1): δ 11.00 (br, 1 H), 8.41 (s, 1 H), 8.16 (d, J = 8.6, 1 H), 8.03 (d, J = 8.6, 1 H), 7.47 (m, 1 H), 7.34 (d, J = 8.3, 1 H), 7.23 (d, J = 7.5, 1 H), 2.40 (br, 1 H) | |
| E1 | 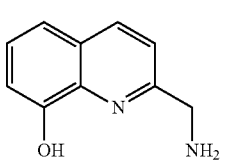 | 82 | (CDCl$_3$/DMSO-d$_6$, 19:1): δ 8.12 (d, J = 8.0, 1 H), 7.46-7.30 (m, 4 H), 7.17 (d, J = 7.3, 1 H), 4.20 (br s, 2 H), 3.20 (br, 2 H) | |

TABLE 2-continued

Data for Examples 3, 4, 5 and 6

| Product ID | Product | Yield (%) | ¹H NMR data | Mass spectral data |
|---|---|---|---|---|
| E2 | | 60 | (CDCl$_3$): δ 8.25 (d, J = 8.3, 1 H), 7.53-7.48 (m, 2 H), 7.38 (d, J = 8.3, 1 H), 7.30 (d, J = 7.6, 1 H), 6.70 (br, 1 H), 4.82 (m, 2 H), 3.53 (s, 1 H), 2.14 (s, 3 H) | |
| E3 | | 82 | (CDCl$_3$/DMSO-d$_6$, 19:1): δ 8.89 (br, 1 H), 8.20 (d, J = 8.5, 1 H), 7.56 (m, 1 H), 7.50-7.40 (m, 2 H), 7.33 (d, J = 8.0, 1 H), 7.21 (d, J = 7.5, 1 H), 5.30 (br, 1 H), 4.83 (m, 2 H), 2.88 (br s, 3 H) | |
| F1 | | 61 | (CDCl$_3$/DMSO-d$_6$, 19:1): δ 8.02 (d, J = 8.6, 1 H), 7.50 (s, 1 H), 7.35-7.20 (m, 4 H), 7.06 (d, J = 7.3, 1 H), 6.74 (s, 1 H), 6.30 (br, 2 H), 4.10 (s, 2 H), 3.03 (m, 2 H), 2.84 (m, 2 H) | |
| F2 | | 86 | (CDCl$_3$): δ 8.63 (d, J = 4.7, 1 H), 8.11 (d, J = 8.3, 1 H), 7.66 (m, 1 H), 7.46 (d, J = 8.3, 1 H), 7.41 (d, J = 7.8, 1 H), 7.34 (d, J = 8.3, 1 H), 7.28 (d, J = 8.3, 1 H), 7.22-7.16 (m, 2 H), 4.18 (m, 2 H), 4.02 (m, 2 H), 2.60 (br, 2 H) | |
| F3 | | 68 | (CDCl$_3$): δ 8.53 (d, J = 4.9, 1 H), 8.06 (d, J = 8.3, 1 H), 7.59 (m, 1 H), 7.45 (d, J = 8.3, 1 H), 7.40 (d, J = 7.8, 1 H), 7.29 (d, J = 8.3, 1 H), 7.16 (d, J = 8.3, 1 H), 7.14 (m, 1 H), 3.91 (s, 2 H), 3.08 (m, 2 H), 2.91 (m, 2 H), 2.39 (s, 3 H) | |
| G1 | | 77 | (CDCl$_3$/DMSO-d$_6$, 19:1): δ 8.02 (d, J = 8.6, 1 H), 7.50 (s, 1 H), 7.35-7.20 (m, 4 H), 7.06 (d, J = 7.3, 1 H), 6.74 (s, 1 H), 6.30 (br, 2 H), 4.10 (s, 2 H), 3.03 (m, 2 H), 2.84 (m, 2 H) | |

TABLE 2-continued

Data for Examples 3, 4, 5 and 6

| Product ID | Product | Yield (%) | ¹H NMR data | Mass spectral data |
|---|---|---|---|---|
| G2 | | 79 | (CDCl$_3$/DMSO-d$_6$, 19:1): δ 8.61 (d, J = 4.9, 1 H), 8.00 (d, J = 8.3, 1 H), 7.68 (s, 1 H), 7.59 (dd, J = 7.5 and 7.5, 1 H), 7.42-7.13 (m, 7 H), 6.71 (s, 1 H), 4.04 (s, 2 H), 3.93 (s, 4 H), 3.90 (br, 1 H), 2.89 (br s, 4 H) | |
| H1 | | 66 | (CDCl$_3$/DMSO-d$_6$, 19:1): δ 8.59 (d, J = 4.8, 1 H), 8.10 (d, J = 8.5, 1 H), 7.71-7.64 (m, 2 H), 7.57 (d, J = 8.5, 1 H), 7.48-7.37 (m, 2 H), 7.32-7.14 (m, 3 H), 6.96 (s, 1 H), 3.98 (s, 2 H), 3.84 (s, 2 H), 3.80 (br, 1 H), 3.72 (s, 2 H) | 346 (M⁺ + 1) |
| H3 | | 51 | (CDCl$_3$/DMSO-d$_6$, 19:1): δ 8.11 (d, J = 8.3, 1 H), 7.80-7.65 (m, 2 H), 7.53 (d, J = 8.0, 1 H), 7.45-7.10 (m, 5 H), 6.76 (s, 1 H), 5.30 (br, 1 H), 4.08 (m, 4 H), 2.94 (m, 4 H) | 363 (M⁺ + 1) |
| H2 | | 73 | (CDCl$_3$): δ 8.57 (m, 2 H), 8.10 (d, J = 8.5, 1 H), 7.70-7.63 (m, 2 H), 7.62-7.54 (m, 3 H), 7.41 (dd, J = 8.0 and 8.0, 1 H), 7.31-7.14 (m, 4 H), 4.03 (s, 2 H), 3.94 (s, 4 H), 3.40 (br, 1 H) | 357 (M⁺ + 1) |

TABLE 3

Data for Examples 7

| Product ID | Product | Yield (%) | ¹H NMR data | Mass spectral data |
|---|---|---|---|---|
| I1 | | 72 | (CDCl$_3$): δ 8.73 (d, J = 8.7, 1 H), 8.28 (d, J = 9.0, 1 H), 8.25 (d, J = 9.0, 1 H), 7.81 (s, 1 H), 7.66 (s, 1 H), 7.46-7.36 (m, 2 H), 7.23 (m, 1 H), 6.56 (m, 1 H) | |

TABLE 3-continued

Data for Examples 7

| Product ID | Product | Yield (%) | $^1$H NMR data | Mass spectral data |
|---|---|---|---|---|
| I2 | 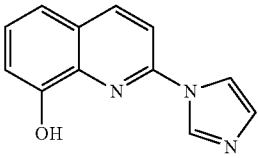 [SMILES: Oc1cccc2ccc(-n3ccnc3)nc12] | 75 | (CDCl$_3$): δ 8.47 (s, 1 H), 8.34 (d, J = 8.9, 1 H), 7.82 (s, 1 H), 7.70 (br, 1 H), 7.57 (d, J = 8.9, 1 H), 7.48 (dd, J = 7.5 and 7.5, 1 H), 7.39 (m, 1 H), 7.28-7.25 (m, 2 H) | |
| I3 | 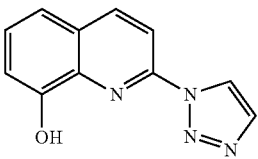 [SMILES: Oc1cccc2ccc(-n3ccnn3)nc12] | 71 | (DMSO-d$_6$) (400 MHz): δ 8.96 (br, 1 H), 7.58 (d, J = 9.4, 1 H), 7.54-7.49 (m, 2 H), 7.37 (d, J = 7.8, 1 H), 7.31 (dd, J = 7.8 and 7.8, 1 H), 7.18 (dd, J = 1.4 and 7.8, 1 H) | |
| I4 | 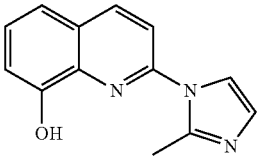 [SMILES: Cc1nccn1-c1ccc2cccc(O)c2n1] | 68 | (CDCl$_3$): δ 8.34 (dd, J = 1.5 and 8.8, 1 H), 7.86 (br, 1 H), 7.58-7.48 (m, 2 H), 7.42-7.40 (m, 2 H), 7.28 (d, J = 7.8, 1 H), 7.10 (br, 1 H), 2.71 (s, 3 H) | |

TABLE 4

Data for Examples 8, 9, 10 and 11

| Product ID | Product | Yield (%) | $^1$H NMR data | Mass spectral data |
|---|---|---|---|---|
| K1 | 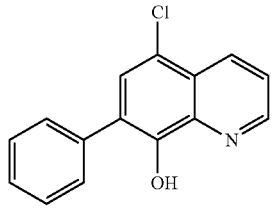 [SMILES: Oc1c(-c2ccccc2)cc(Cl)c2cccnc12] | 89 | (CDCl$_3$/DMSO-d$_6$, 19:1): δ 9.16 (m, 1 H), 9.03 (d, J = 8.6, 1 H), 7.95 (dd, J = 5.3 and 8.6, 1 H), 7.82 (m, 1 H), 7.58 - 7.42 (m, 3 H), 5.65 (br, 1 H) | 256 (M$^+$ + 1, 100%), 258 (M$^+$ + 1, 33%) |
| K2 | 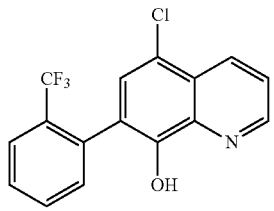 [SMILES: Oc1c(-c2ccccc2C(F)(F)F)cc(Cl)c2cccnc12] | 55 | (CDCl$_3$/DMSO-d$_6$, 19:1): δ 9.23 (d, J = 5.1, 1 H), 9.13 (m, 1 H), 8.02 (m, 1 H), 7.83 (d, J = 8.0, 1 H), 7.69 (s, 1 H), 7.64 (m, 1 H), 7.41 (d, J = 7.3, 1 H), 5.60 (br, 1 H) | 324 (M$^+$ + 1, 100%), 326 (M$^+$ + 1, 33%) |
| K3 | 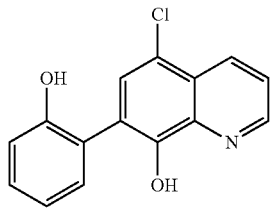 [SMILES: Oc1ccccc1-c1cc(Cl)c2cccnc2c1O] | 96 | (DMSO-d$_6$)(400 MHz): δ 8.99 (d, J = 4.0, 1 H), 8.57 (d, J = 8.4, 1 H), 7.78 (dd, J = 4.0 and 8.4, 1 H), 7.62 (s, 1 H), 7.35 (m, 1 H), 7.18 (m, 1 H), 7.16-6.86 (m, 2 H) | 270 [(M − H)$^-$, 100%], 272 [(M − H)$^-$, 33%] |

TABLE 4-continued

Data for Examples 8, 9, 10 and 11

| Product ID | Product | Yield (%) | $^1$H NMR data | Mass spectral data |
|---|---|---|---|---|
| K4 | 7-(2-methylphenyl)-5-chloro-8-hydroxyquinoline | 90 | (CDCl$_3$/DMSO-d$_6$, 19:1): δ 9.19 (d, J = 5.0, 1 H), 9.13 (d, J = 8.3, 1 H), 7.96 (dd, J = 5.0 and 8.3, 1 H), 7.73 (s, 1 H), 7.40-7.22 (m, 4 H), 4.10 (br, 1 H), 2.23 (s, 3 H) | 270 (M$^+$ + 1, 100%), 272 (M$^+$ + 1, 33%) |
| K5 | 7-(2-fluorophenyl)-5-chloro-8-hydroxyquinoline | 95 | (CDCl$_3$/DMSO-d$_6$, 19:1): δ 9.19 (m, 1 H), 9.12 (d, J = 8.5, 1 H), 8.00 (dd, J = 5.1 and 8.5, 1 H), 7.83 (s, 1 H), 7.54 (m, 1 H), 7.47 (m, 1 H), 7.30 (dd, J = 8.3 and 8.5, 1 H), 7.22 (dd, J = 8.5 and 8.5, 1 H), 7.00 (br, 1 H) | 274 (M$^+$ + 1, 100%), 276 (M$^+$ + 1, 33%) |
| K6 | 7-(3-methoxyphenyl)-5-chloro-8-hydroxyquinoline | 98 | (CDCl$_3$/DMSO-d$_6$, 19:1): δ 9.17 (d, J = 4.7, 1 H), 9.10 (d, J = 8.3, 1 H), 7.96 (dd, J = 4.9 and 8.3, 1 H), 7.91 (s, 1 H), 7.43 (dd, J = 8.1 and 8.1, 1 H), 7.28-7.24 (m, 2 H), 6.95 (m, 1 H), 5.00 (br, 1 H), 3.88 (s, 3 H) | 286 (M$^+$ + 1, 100%), 288 (M$^+$ + 1, 33%) |
| K7 | 7-(4-methoxyphenyl)-5-chloro-8-hydroxyquinoline | 95 | (CDCl$_3$/DMSO-d$_6$, 19:1): δ 9.16-9.00 (m, 2 H), 7.92 (dd, J = 4.9 and 8.6, 1 H), 7.88 (d, J = 6.3, 1 H), 7.22-7.66 (m, 2 H), 7.07-7.05 (m, 2 H), 5.70 (br, 1 H), 3.85 (s, 3 H) | 286 (M$^+$ + 1, 100%), 288 (M$^+$ + 1, 33%) |
| K8 | 7-(3-iodophenyl)-5-chloro-8-hydroxyquinoline | 95 | (CDCl$_3$/DMSO-d$_6$, 19:1): δ 9.19-9.13 (m, 2 H), 8.05-7.93 (m, 2 H), 7.54-7.48 (m, 2 H), 7.40 (dd, J = 7.3 and 7.3, 1 H), 7.27 (d, J = 7.3, 1 H), 6.65 (br, 1 H), 2.45 (s, 3 H) | |
| K9 | 7-(4-dimethylaminophenyl)-5-chloro-8-hydroxyquinoline | 97 | (CDCl$_3$/DMSO-d$_6$, 19:1): δ 9.04 (m, 1 H), 8.81 (d, J = 8.5, 1 H), 7.97-7.88 (m, 4 H), 7.82 (m, 1 H), 7.75 (s, 1 H), 4.20 (br, 1 H), 3.26 (s, 6 H) | |

TABLE 4-continued

Data for Examples 8, 9, 10 and 11

| Product ID | Product | Yield (%) | $^1$H NMR data | Mass spectral data |
|---|---|---|---|---|
| K10 | 5-chloro-7-(2-formylphenyl)-8-hydroxyquinoline | 68 | (CDCl$_3$/DMSO-d$_6$, 19:1): δ 9.24 (s, 1 H), 8.74 (d, J = 8.3, 1 H), 8.52 (d, J = 8.0, 1 H), 8.36 (s, 1 H), 8.24 (d, J = 8.0, 1 H), 7.97 (dd, J = 7.3 and 7.3, 1 H), 7.82-7.70 (m, 3 H), 4.20 (br, 1H) | |
| K11 | 7-(benzothiophen-2-yl)-5-chloro-8-hydroxyquinoline | 23 | (DMSO-d$_6$)(400 MHz): δ 9.47 (d, J = 6.0, 1 H), 9.09 (d, J = 8.0, 1 H), 8.51 (s, 1 H), 8.40 (s, 1 H), 8.25 (m, 1 H), 8.10 (m, 1 H), 8.00 (m, 1 H), 7.48-7.44 (m, 2 H) | |
| K12 | 5-chloro-7-(3,5-difluorophenyl)-8-hydroxyquinoline | 93 | (CDCl$_3$/DMSO-d$_6$, 19:1): δ 9.04 (m, 1 H), 7.82 (m, 1 H), 7.81 (m, 1 H), 7.74 (s, 1 H), 7.38-7.30 (m, 2 H), 6.88 (m, 1 H), 4.60 (br, 1 H) | |
| K13 | 5-chloro-7-(2,4-difluorophenyl)-8-hydroxyquinoline | 43 | (CDCl$_3$/DMSO-d$_6$, 19:1): δ 9.05 (m, 1 H), 8.81 (d, J = 8.6, 1 H), 7.81 (m, 1 H), 7.67 (s, 1 H), 7.57 (m, 1 H), 7.07-6.95 (m, 2 H), 3.25 (br, 1 H) | |
| K14 | 5-chloro-8-hydroxy-7-(thiophen-3-yl)quinoline | 91 | (CDCl$_3$/DMSO-d$_6$, 19:1): δ 9.00 (m, 1 H), 8.53 (m, 1 H), 8.16 (m, 1 H), 8.06 (s, 1 H), 7.82 (m, 1 H), 7.75 (dd, J = 4.2 and 8.5, 1 H), 7.66 (dd, J = 2.9 and 5.9, 1 H) | |
| K15 | 5-chloro-7-(3-fluorophenyl)-8-hydroxyquinoline | 97 | (CDCl$_3$/DMSO-d$_6$, 19:1): δ 9.13 (m, 1 H), 9.03 (m, 1 H), 7.93 (m, 1H), 7.87 (m, 1 H), 7.52-7.43 (m, 3H), 7.14 (m, 1H), 5.35 br, 1 H) | |

TABLE 4-continued

Data for Examples 8, 9, 10 and 11

| Product ID | Product | Yield (%) | $^1$H NMR data | Mass spectral data |
|---|---|---|---|---|
| K16 | 5-chloro-7-(4-fluorophenyl)-8-hydroxyquinoline | 69 | (CDCl$_3$/DMSO-d$_6$, 19:1): δ 9.14 (d, J = 4.9, 1 H), 9.05 (d, J = 8.6, 1 H), 7.94 (dd, J = 5.2 and 8.6, 1 H), 7.86 (s, 1 H), 7.75-7.69 (m, 2 H), 7.24-6.75 (m, 2 H), 5.20 (br, 1 H) | 509 (M$^+$ + 1, 100%), 511 (M$^+$ + 1, 33%) |
| K17 | 5-chloro-7-(3-nitrophenyl)-8-hydroxyquinoline | 41 | (CDCl$_3$/DMSO-d$_6$, 19:1): δ 9.06 (m, 1 H), 8.78 (m, 1 H), 8.64 (m, 1 H), 8.26 (m, 1 H), 8.14 (d, J = 8.0, 1 H), 7.83 (dd, J = 4.6 and 8.8, 1 H), 7.80 (s, 1 H), 7.72 (dd, J = 8.0 and 8.0, 1 H), 4.60 (br, 1 H) | |
| L1 | 7-bromo-5-phenyl-8-hydroxyquinoline | 88 | (CDCl$_3$): δ 9.00-8.88 (m, 2 H), 8.02 (s, 1 H), 7.83 (m, 1 H), 7.60-7.38 (m, 5 H), 3.80 (br, 1 H) | 300 (M$^+$ + 1, 100%), 302 (M$^+$ + 1, 100%) |
| L2 | 7-bromo-5-(3,5-difluorophenyl)-8-hydroxyquinoline | 68 | (CDCl$_3$/DMSO-d$_6$, 19:1): δ 9.18 (m, 1 H), 8.74 (m, 1 H), 7.92-7.84 (m, 2 H), 7.04-6.95 (m, 3 H), 5.00 (br, 1 H) | 336 (M$^+$ + 1, 100%), 338 (M$^+$ + 1, 33%) |
| M1 | 5,7-diphenyl-8-hydroxyquinoline | 91 | (CDCl$_3$/DMSO-d$_6$, 19:1): δ 9.15 (m, 1 H), 8.92 (d, J = 8.3, 1 H), 7.89 (m, 1 H), 7.81 (m, 1 H), 7.78-7.72 (m, 2 H), 7.60-7.41 (m, 8 H), 4.60 (br, 1 H) | 298 (M$^+$ + 1) |

TABLE 4-continued

Data for Examples 8, 9, 10 and 11

| Product ID | Product | Yield (%) | $^1$H NMR data | Mass spectral data |
|---|---|---|---|---|
| M2 | 5,7-bis(2-methylphenyl)-8-hydroxyquinoline structure | 70 | (CDCl$_3$/DMSO-d$_6$, 19:1): δ 9.10 (m, 1 H), 9.52 (d, J = 8.3, 1 H), 7.81 (m, 1 H), 7.59 (s, 1 H), 7.45-7.23 (m, 8 H), 3.50 (br, 1 H), 2.25 (s, 3 H), 2.03 (s, 3 H) | |
| M3 | 5,7-bis(2-methoxyphenyl)-8-hydroxyquinoline structure | 29 | (CDCl$_3$/DMSO-d$_6$, 19:1): δδ 9.25 (m, 1 H), 8.59 (d, J = 8.3, 1 H), 7.88-7.81 (m, 2 H), 7.56-7.32 (m, 5 H), 7.18-7.03 (m, 3 H), 3.90 (br, 1 H), 3.73 (s, 6 H) | |
| M4 | 5,7-bis(2-trifluoromethylphenyl)-8-hydroxyquinoline structure | 4 | | 432 (M − H)$^-$ |
| M5 | 5,7-bis(2-fluorophenyl)-8-hydroxyquinoline structure | 39 | (CDCl$_3$/DMSO-d$_6$, 19:1): δ 9.13 (m, 1 H), 8.60 (m, 1 H), 7.82 (m, 1 H), 7.76 (s, 1 H), 7.64-7.18 (m, 8 H), 3.30 (br, 1 H) | |
| N2 | 5-(2-methylphenyl)-7-iodo-8-hydroxyquinoline structure | 16 | (CDCl$_3$/DMSO-d$_6$, 19:1): δ 9.07 (d, J = 4.4, 1 H), 8.42 (d, J = 8.3, 1 H), 8.08 (s, 1 H), 7.81 (dd, J = 3.2 and 8.3, 1 H), 7.47-7.30 (m, 3 H), 7.20 (d, J = 7.4, 1 H), 5.80 (br, 1 H), 2.01 (s, 3 H) | |

TABLE 4-continued

Data for Examples 8, 9, 10 and 11

| Product ID | Product | Yield (%) | $^1$H NMR data | Mass spectral data |
|---|---|---|---|---|
| N3 | 5-(2-methoxyphenyl)-7-iodo-8-hydroxyquinoline | 46 | (CDCl$_3$/DMSO-d$_6$, 19:1): δ 9.06 (d, J = 3.9, 1 H), 8.53 (d, J = 8.5, 1 H), 8.08 (s, 1 H), 7.83 (dd, J = 5.2 and 8.6, 1 H), 7.51 (m, 1 H), 7.27 (m, 1 H), 7.15 (d, J = 8.3, 1 H), 7.07 (d, J = 8.3, 1 H), 4.50 (br, 1 H), 3.70 (s, 3H) | 378 (M$^+$ + 1) |
| N4 | 5-(2-trifluoromethylphenyl)-7-iodo-8-hydroxyquinoline | 79 | (CDCl$_3$/DMSO-d$_6$, 19:1): δ 9.08 (m, 1 H), 8.26 (m, 1 H), 8.07 (s, 1 H), 7.89 (m, 1 H), 7.80 (dd, J = 5.1 and 8.5, 1 H), 7.75-7.65 (m, 2 H), 7.36 (m, 1 H), 5.75 (br, 1 H) | 416 (M$^+$ + 1) |
| N5 | 5-(2-fluorophenyl)-7-iodo-8-hydroxyquinoline | 59 | (CDCl$_3$/DMSO-d$_6$, 19:1): δ 9.11 (m, 1 H), 8.54 (m, 1 H), 8.10 (s, 1 H), 7.88 (dd, J = 5.1 and 8.7, 1 H), 7.54 (m, 1 H), 7.42-7.22 (m, 3 H), 5.30 (br, 1 H) | 366 (M$^+$ + 1) |
| O1 | 5,5'-dichloro-7,7'-bi(8-hydroxyquinoline) | 22 | | 355 [(M − H)$^−$, 100%], 357 [(M − H)$^−$, 66%], |

TABLE 5

Data for the 2-aromatic group-substituted 8-HQ Derivatives (prepared via the Negishi Coupling Reaction)$^a$

| Product ID | Product | Yield (%) | $^1$H NMR data | Mass spectral data |
|---|---|---|---|---|
| P1 | 2-(2-pyridyl)-8-hydroxyquinoline | 89 | (CDCl$_3$): δ 8.98 (d, J = 3.9, 1 H), 8.60 (d, J = 8.8, 1 H), 8.40-8.15 (m, 3 H), 7.75 (m, 1 H), 7.60 (m, 1H), 7.50-7.35 (m, 3 H) | 223 (M$^+$ + 1) |

TABLE 5-continued

Data for the 2-aromatic group-substituted 8-HQ Derivatives (prepared via the Negishi Coupling Reaction)[a]

| Product ID | Product | Yield (%) | $^1$H NMR data | Mass spectral data |
|---|---|---|---|---|
| P2 | (structure: 8-hydroxyquinoline with 2-(2-methylthiophenyl) substituent) | 80 | (CDCl$_3$/DMSO-d$_6$, 19:1): δ 8.68 (d, J = 8.3, 1 H), 7.93 (d, J = 8.3, 1 H), 7.76-7.54 (m, 5 H), 7.50 (d, J = 7.5, 1 H), 7.41 (dd, J = 7.3 and 7.3, 1 H), 2.50 (br, 1 H), 2.49 (s, 3 H) | 268 (M$^+$ + 1) |
| P3 | (structure: 8-hydroxyquinoline with 2-(2-ethoxycarbonylphenyl) substituent) | 33 | (CDCl$_3$): δ 8.66 (d, J = 8.8, 1 H), 8.22 (d, J = 7.1, 1 H), 7.80-7.38 (m, 7 H), 4.20 (q, J = 7.0, 2 H), 1.70 (br, 1 H), 1.18 (t, J = 7.0, 3 H) | 294 (M$^+$ + 1) |
| P4 | (structure: 8-hydroxyquinoline with 2-(6-methylpyridin-2-yl) substituent) | 95 | (CDCl$_3$/DMSO-d$_6$, 19:1): δ 8.64 (d, J = 8.5, 1 H), 8.42 (d, J = 7.6, 1 H), 8.28 (d, J = 8.5, 1 H), 8.10 (m, 1 H), 7.78 (m, 1 H), 7.48-7.16 (m, 3 H), 2.68 (s, 3 H), 2.59 (br, 1 H) | 279 (M$^+$ + 1) |

Example 20

Assessment of Compounds of Formula I or II

The following Assays were used in the assessment of the compounds of formula I or II for suitability for use in the methods of the invention.

Assay 1. Fluorometric H$_2$O$_2$ Assay

A fluorometric assay was used to test the ability of a test compound to inhibit hydrogen peroxide generation by Aβ in the presence of copper based on dichlorofluoroscein diacetate (DCF; Molecular Probes, Eugene Oreg.). The DCF solution (5 mM) in 100% dimethyl sulphoxide (previously purged with argon for 2 hr at 20° C.) was deacetylated in the presence of 0.25M NaOH for 30 min and neutralised at pH 7.4 to a final concentration of 1 mM. Horseradish peroxidase (HRP) stock solution was prepared to 1 μM at pH 7.4. The reactions were carried out in PBS, pH 7.4 in a 96 well plate (total volume=250 μl/well). The reaction solutions contained Aβ 1-42 at concentrations in the range of 50 nM to 1 μM, copper-glycine chelate (Cu-Gly), was prepared by adding CuCl$_2$ to glycine in the ratio of 1:6 and added to the Aβ in the proportion 2Cu-Gly: 1Aβ), reducing agents including dopamine (5 μM) or ascorbic acid, deacetylated DCF 100 μM, and HRP, 0.1 μM. 1-10 μM EDTA or another chelator may also be present as a control for free copper, but was not required for the assay to function. The reaction mixture was incubated at 37 C for 60 min. Catalase (4000 units/ml) and H$_2$O$_2$ (1-2.5 μM) standards in PBS pH 7.4 may be included as positive controls. Fluorescence was recorded using a plate reader with excitation and emission filters at 485 nM and 530 nM respectively. H$_2$O$_2$ concentration may be established by comparing fluorescence with the H$_2$O$_2$ standards. Inhibition of AB H$_2$O$_2$ production was assayed by including a given concentration of test compound(s) in the test wells.

Assay 2. Neurotoxicity Assays

Primary Cortical Neuronal Cultures

Cortical cultures were prepared as previously described (White et al., 1998). Embryonic day 14 BL6Jx129sv mouse cortices were removed, dissected free of meninges and dissociated in 0.025% (wt/vol) trypsin. Dissociated cells were plated in 48 well culture plates at a density of 2×10$^6$ cells/mL in MEM with 25% (vol/vol) FCS and 5% (vol/vol) HS and incubated at 37° C., 2 hrs. Media was then replaced with Neurobasal media (Invitrogen Life Technologies) and B27 supplements (Invitrogen Life Technologies). Cultures were maintained at 37° C. in 5% CO$_2$. Prior to experimentation, the culture medium was replaced with Neurobasal media and B27 minus antioxidants (Invitrogen Life Technologies).

Primary Cerebellar Granule Neuronal Cultures

Cerebella from post-natal day 5-6 (P5-6) mice were removed and dissected free of meninges and dissociated in 0.025% trypsin. Cerebellar granule neurons (CGN) were plated in 24 well culture plates at 350 000 cells/cm$^2$ in BME (Invitrogen Life Technologies) supplemented with 10% Fetal Calf Serum (FCS), 2 mM glutamine and 25 mM KCl. Gentamycin sulphate (100 μg/mL) was added to all plating media and cultures were maintained at 37° C. in 5% CO$_2$.

Assay 3. Assays for Cell Viability (a) MTS Assay for Cell Viability

Cell viability is determined using the MTS assay. Culture medium is 2.5 replaced with fresh neurobasal medium plus B27 supplements minus antioxidants. ⅒th volume MTS solution (Cell Titre 96 Aqueous One, Promega Corporation) and incubated at 37° C., 2 hrs. 200 microliter aliquots are measured with a spectrophotometer at 560 nm.

(b) LDH Assay for Cell Viability

Cell death is determined from culture supernatants free of serum and cell debris using the lactate dehydrogenase (LDH)

Cytotoxicity Detection Kit (Boehringer Ingelheim) according to the manufacturer's instructions.

(c) Assay for Aβ Neurotoxicity and Aβ Neuroprotection

Neuronal cortical cells were cultured for five days as per Assay 2. On day six the neurobasal (NB) media (Invitrogen Life Technologies) and B27 supplement (Invitrogen Life Technologies) were replaced with NB media and B27 supplement (no antioxidants). On day six, test compounds were individually added to the neuronal cell cultures:

The test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 uM, 2.5 uM, 2.5 uM.

Aβ Preparation:

Aβ was initially dissolved in 20 mM NaOH to a concentration of 1 mM and sonicated for 5 minutes. The peptide was then diluted in $H_2O$ and 10×PBS to a final concentration of 200 uM Aβ in 1×PBS. The peptide was again sonicated for 5 minutes and then spun at 14000 rpm for 5 min and transferred to a fresh tube.

The test compounds were dissolved in 100% DMSO to a concentration of 2.5 mM (10 mM if excess compound was weighed out per vial—then diluted to 2.5 mM). 2.5 mM stock solution was serially diluted 1 in 10 [in NB media and B27 (no antioxidants)] to give working solutions of 250 uM, 25 uM, 2.5 uM. Test compounds were not added directly to cells, instead they were added to a 48 well 'Drug Plate' as comprised below:

Preparation of "Drug Plate":
To a 48 well plate add:
Well 1: 515 ul NB+B27 (no antioxidant)*+24 ul 25 uM test compound+60 ul Aβ diluent**
* NB media+B27 (no antioxidants),
** Aβ diluent 2 mM NaOH, 1×PBS
Well 2: 515 ul NB+B27 (no antioxidant)+24 ul 250 uM test compound+60 ul Aβ diluent
Well 3: 515 ul NB+B27 (no antioxidant)+24 ul test compound diluent***+60 ul Aβ1-42
*** PBT diluent 10% DMSO in NB+B27 (no antioxidant)
Well 4: 515 ul NB+B27 (no antioxidant)+24 ul 2.5 uM test compound+60 ul Aβ1-42
Well 5: 515 ul NB+B27 (no antioxidant)+24 ul 25 uM test compound+60 ul Aβ1-42
Well 6: 515 ul NB+B27 (no antioxidant)+24 ul 250 uM test compound+60 ul Aβ1-42 diluent
Well 7: 515 ul NB+B27 (no antioxidant)+24 ul test compound diluent+60 ul Aβ1-42 diluent
Well 8: 600 ul NB+B27 (no antioxidant)
N.B. 60 ul Aβ1-42 equals 20 ul Aβ1-42 per well equals 20 uM Aβ1-42

The Drug Plate was incubated at 37° C. for 15 mins. 200 ul of each well was added in triplicate to the corresponding cell plate. The cell plate was incubated at 37 C, for 4 days.

Completion of the Assay:

On the $4^{th}$ day after treating the cells the assay is completed by adding MTS to the cells.

(d) Assay for Test Compound Cytoxicity

Neuronal cortical cells were cultured for five days as per Assay 2 in NB media and B27 supplement.

On day six the test compounds were added to the neuronal cell cultures in NB media and B27 supplement minus antioxidants.

Test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 uM, 25 uM, 2.5 uM. Test compounds were not added directly to cells, instead they were added to a 48 well 'Drug Plate' as comprised below:

Preparation of "Drug Plate":
To a 48 well plate add:
Well 1: 576 ul NB+B27 (no antioxidant)*+24 ul 2.5 uM test compound
* NB media and B27 (no antioxidants),
Well 2: 576 ul NB+B27 (no antioxidant)+24 ul 25 uM test compound
Well 3: 576 ul NB+B27 (no antioxidant)+24 ul 250 uM test compound
Well 4: 576 ul NB+B27 (no antioxidant)+24 ul 2.5 uM test compound
Well 5: 576 ul NB+B27 (no antioxidant)+24 ul 25 uM test compound
Well 6: 576 ul NB+B27 (no antioxidant)+24 ul 250 uM test compound
Well 7: 576 ul NB+B27 (no antioxidant)+24 ul test compound diluent**
** PBT diluent 10% DMSO in NB+B27 (no antioxidants)
Well 8: 600 ul NB+B27 (no antioxidant)

The Drug Plate was incubated at 37° C. for 15 mins. 200 ul of each well was added in triplicate to the corresponding cell plate. The cell plate was incubated at 37 C, for 4 days.

On completion of the assay, ⅒ volume MTS was added per well of plate (ie 25 ul/250 ul). The plates were incubated at 37 C for 2 hrs, and then absorbance was read at 560 nm.

Assay 4. Caspase Assay

To measure caspase activity in neuronal cultures, growth medium is removed, cells are washed twice with control salt solution (pH 7.4) and ice-cold cell extraction buffer is added directly to the cultures. The extraction buffer consists of 20 mM Tris (pH 7.4), 1 mM sucrose, 0.25 mM EDTA, 1 mM dithiothreitol (DTT), 0.5 mM PMSF, 1% Triton X-100 (Tx-100) and 1 μg/mL of pepstatin and aprotinin. After incubation for 15 min on ice, the extraction buffer is removed, centrifuged for 5 min at 4° C. in a microcentrifuge and 100 μL of supernatant is added to each well of a 96 well plate. 100 μL of 200 μM substrate (either DEVD-pNA, VEID-pNA or IETD-pNA for caspases 3, 6 and 8 respectively) is added to each well to give a final concentration of 100 μM substrate. Plates are incubated at 37° C. for 2, 4, 6 or 24 hr and the absorbance is determined at a wavelength of 415 nm (Abs415). The absorbance reading is compared to a known standard of pNA alone.

Assay 5. Annexin V Assay

To determine the level of annexin V binding to cells, cultures are washed twice with control salt solution (pH 7.4) followed by the addition of annexin V-FITC at a concentration of approximately 0.5 μg/mL in control salt solution (pH 7.4). Propidium iodide (10 μg/mL) is also added to the cultures at the same time. Cells are incubated in the dark for 30 min at ambient temperature and subsequently washed three times with fresh control salt solution. Analysis of FITC fluorescence (ex. 488 nm, em. 510 nm) is determined using a Leica DMIRB microscope. Photographs are taken with a Leica MPS 60 camera attachment using ASA400 colour film, and negatives are scanned into Adobe Photoshop v2.0.1.

Assay 6. Lipoprotein Oxidation Assay

Two different assays of metal-mediated lipid peroxidation can be utilized. The first assay involves measuring the oxidative activity of metallated proteins. This is determined by mixing dialyzed metallated or native protein (at designated concentrations) with 0.5 mg/mL LDL for 24 hr (37° C.). Lipid peroxidation (LPO) is measured using a lipid peroxidation assay kit (LPO 486, Oxis International Inc. Portland, Oreg.)

as per kit instructions. The level of LPO is determined by comparing absorbance (486 nm) with LDL alone (100% LPO). The second assay is used to measure the LPO activity of native proteins in the presence of free, non-protein-bound Cu. This involves adding non-metallated peptides (140 μM) to 0.5 mg/mL LDL together with 20 μM Cu-gly and assaying for LPO as for the metallated proteins. The level of LPO is determined by comparing the absorbance (486 nm) with LDL+Cu-gly (100% LPO). As a negative control, LDL is also exposed to dialysed Cu-gly solutions comparable to those used to Cu-metallate the proteins.

Assay 7. Cytotoxicity Induced by Cu-Metallated Proteins

Proteins or synthetic peptides are mixed with metal-glycine solutions at equimolar or two-fold metal to protein concentration. Metal-protein mixtures are incubated overnight at 37° C. and then extensively dialysed (24 hr against two changes of $dH_2O$ (3 L/change) at room temperature) using mini-dialysis cups with a 3,500 kilodalton cut-off (Pierce, Rockford, Ill.). Dialysis of proteins against PBS pH 7.4 resulted in metallated proteins with identical activity to $dH_2O$ dialysis.

To determine their neurotoxic effects, metallated proteins, native proteins or peptides are added to two day-old primary cortical neuronal cultures. The cultures are also exposed to Cu-gly (5 or 10 μM) or LDL. Positive control cultures are treated with Cu-gly+LDL or the LPO product, 4-hydroxynonenol (HNE, Sigma Chemicals). Cultures are assayed for cell death using the lactate dehydrogenase (LDH) assay kit (Roche Molecular Biochemicals, Nunawading, Australia) according to the manufacturer's instructions.

Assay 8. Acridine Orange Assay for Aβ-Mediated Loss of Lysosomal Acidification

Cultured mouse cortical neurons are treated with Aβ1-42 (20 μM) for 16 h and then stained with 5 mg/ml acridine orange (AO) for 5 min at 37° C. 15 min at 37° C. The AO-induced fluorescence is measured with a red filter on a fluorescence microscope. AO is a lysosomotropic weak base which accumulates in the endosomal/lysosomal compartments and displays orange fluorescence during incubation. AO is sequestered inside the lysosomes as long as there is a substantial proton gradient over the lysosomal membranes. Treatment of cells with Aβ1-42 disrupts the lysosomal membrane proton gradient and relocalises AO into the cytosol, as indicated by the loss of orange fluorescence within 16-24 hr.

Assay 9. Human Brain Amyloid Solubilisation Assay

This assay was performed in order to assess the ability of a test compound to mobilise Aβ from the insoluble to the soluble phase of an extract of tissue from post mortem human AD brain.

Up to 0.5 g of plaque-bearing cortex without meninges was homogenized using a DIAX 900 homogenizer (Heudolph and Co, Kelheim, Germany) or other suitable device for three 30-second periods at full speed in 2 ml of ice-cold phosphate-buffered saline, pH 7.4. To obtain the phosphate-buffered saline-extractable fraction, the homogenate was centrifuged at 100,000×g for 30 min and the supernatant removed. Alternatively, the tissue was freeze dried then pulverised to form a powder which was then weighed out into aliquots for extraction as above. Supernatant, either freeze-dried and resuspended or in unconcentrated form, was dissolved in 200 μl of Tris-Tricine sodium dodecyl sulfate (SDS) sample buffer pH 8.3 containing 8% SDS, 10% 2-mercaptoethanol. Aliquots (10 μl) were then boiled for 10 minutes before SDS-polyacrylamide gel electrophoresis. The insoluble fraction of the cortical samples was obtained by resuspending the initial pelleted sample in 1 ml of phosphate-buffered saline. A 50-μl aliquot of this suspension was then boiled in 200 ml of sample buffer as above.

Tris-Tricine polyacrylamide gel electrophoresis was performed by loading appropriately diluted samples on to 10% to 20% gradient gels (Novex, San Diego, Calif.) followed by transfer on to 0.2-μm nitrocellulose membrane (Bio-Rad, Hercules, Calif.). Aβ was detected by using monoclonal antibody W02, which detects residues 5 through 8, 17 (or another suitable antibody) in conjunction with horseradish peroxidase-conjugated rabbit anti-mouse IgG (Dako, Denmark), and visualized by using enhanced chemiluminescence (eg ECL; Amersham Life Science, Buckinghamshire, UK). Each gel included three lanes containing 0.5, 1, and 2 ng of synthetic $Aβ_{40}$ (Keck Laboratory, Yale University, New Haven, Conn.) as reference standards.

Blot films were scanned by using a suitable imaging system such as the UVP gel documentation system, and densitometry performed using suitable software, eg UVP Labworks. The dynamic range of the film/scanner was determined by using a step tablet (No. 911ST600, Kodak, Rochester N.Y.), a calibrated film exposed by the manufacturer to provided steps of known increasing intensity. The quantifiable range of signal intensity for densitometric analysis of the mono- and dimeric Aβ bands was based on the comparison with a curve obtained by scanning and densitometry of the step tablet. Samples wherein the signal intensity is low after preliminary assay may be re-assayed by using synthetic standards of lower or higher concentration.

All samples were analysed at least twice, and gel loadings and dilutions were adjusted to fit within the quantifiable region of the standard curve. The proportion of 'soluble' to 'insoluble' Aβ may be used to determine the efficiency of extraction of a test compound compared with the efficiency of a known compound, such as clioquinol (PBT 1). The insoluble Aβ being comprised of the pelletable fraction derived from the insoluble amyloid plaque from the above cortical samples and the soluble fraction comprising monomeric and/or oligomeric soluble Aβ.

Assay 10. Metal Partitioning

To assay effects upon the partitioning of various metals, including zinc and copper, following extraction of brain tissue in the presence of a test compound, soluble and insoluble fractions from an extract of human brain tissue are prepared as for the amyloid solubilisation assay. Metals in the two fractions are analysed by inductively-coupled plasma mass spectrometry, following appropriate pretreatment with nitric acid and/or hydrogen peroxide where necessary.

Assay 11. Effect of Administration of Test Compounds on Aβ deposits in Transgenic Animals Transgenic mouse models are available for a number of neurological disorders, including Alzheimer's disease (Games et al., 1995; Hsiao et al., 1996); Parkinson's disease (Masliah et al., 2000); familial amyotrophic lateral sclerosis (ALS) (Gurney et al., 1994); Huntington's disease (Reddy et al., 1998); and Creutzfeld-Jakob disease (CJD) (Telling et al., 1994). We have found that one of the transgenic models for Alzheimer's disease, the APP2576 transgenic mouse (Hsiao et al., 1996) also has a high incidence of cataract. These animal models were suitable for testing the methods of the invention.

Transgenic mice of the strain APP2576 (Hsiao et al 1996) were used. Eight to nine month old female mice were selected and divided into groups for treatment.

Mice were sacrificed at intervals, and their brains examined to determine whether the treatment with test compounds decreased brain amyloid formation, and the identification of the most effective administration protocol. The levels of soluble and insoluble Aβ in the brain and serum were determined using calibrated Western blots as per the methodology described for Assay 9. Brain Amyloid Solubilisation Assay.

Other mice in each group were tested over a period of up to eight months for cognitive performance, using a Morris water maze according to standard methods. The general health and well-being of the animals was also measured every day by a blinded operator, using a five point integer scale which subjectively rates a combination of features, including motor activity, alertness and general health signs.

Assay 12. Solubility Assay

Stock solutions of compounds of formula I or II (1 mM) were prepared in dimethyl sulfoxide. Compounds which did not dissolve were classed as not soluble (N). The DMSO stock solutions were diluted 1 in 100 into PBS pH 7.4. Compounds which gave a clear solution were classed as soluble (Y), while those compounds which gave a translucent suspension after dissolution in DMSO were classed as "crashed out" (C).

Assay 13. Physiochemical Properties
Polar Surface Area Calculations (PSA)

Polar surface area values were calculated using the web-based program available through "Molinspiration", a package for calculation of molecular properties.

Turbidimetric Solubility Measurements

The solubility estimate was measured at both pH 2.0 and pH 6.5. This is within the pH range that can be anticipated along the proximal gastrointestinal tract in humans.

The compounds were dissolved in DMSO to appropriate concentrations and then spiked into either 0.01M HCl (approx. pH=2.0) or pH 6.5 isotonic phosphate buffer, the final DMSO concentration being 1%. Samples were then analysed via Nephelometry to determine a solubility range. [as per D. Bevan and R. S. Lloyd, Anal. Chem. 2000, 72, 1781-1787].

c Log P Values

Theoretical Log P values were determined using the ACD Log P software. The values quoted have been calculated from an untrained database and refer to the unionised species.

E Log D

Effective Log D values were measured using a chromatographic method employing a SUPELCOSIL LC-ABZ column using an octanol saturated mobile phase at pH 7.4. See F. Lombardo et al, J. Med. Chem. 2000, 43, 2922-2928.

Assay 14. Blood Brain Barrier Penetration

The test compounds were dissolved in DMSO and phosphate buffered saline (PBS) was added to obtain solutions at a concentration of 50 µM in PBS containing 1.25-2.5% DMSO. A trace amount of $^{14}C$-sucrose was added to each stock infusion solution (approx 0.01 µCi/mL) to act as Blood-Brain Barrier (BBB)-impermeable marker in order to assess the integrity of the BBB during each perfusion and to estimate the volume of the residual vascular space (RVS) in samples of brain tissue (ie: the volume of fluid remaining inside the lumen of blood vessels at the end of each perfusion).

Adult male Spague Dawley rats (180-190 g) were anaesthetized with intraperitoneal injections of Urethane (25% w/v) at a dose of 1.0 mL/100 g body weight. The right common carotid artery was surgically exposed and cannulated for perfusion of the cerebral circulation. The right external carotid artery (which supplies tissues outside the skull) was then ligated distal to its bifurcation from the right common carotid artery so that all of the infusion solution would pass into the brain via the remaining right internal carotid artery. The heart was then exposed and transected immediately prior to the commencement of the infusion. The rate of the infusion was controlled by a pump set to deliver at 3.2 mL/min (approx. 85% of the normal blood supply to the brain for this size of rat). The infusion cannula initially contained a 0.5 mL pre-wash of heparinised PBS (10 IU/ml) that acts to flush blood vessels and to prevent blood from clotting and blocking small vessels.

After 1.5 minutes, the infusion pump automatically stopped, the cannula was withdrawn from the carotid artery and a sample of the infusion solution (1-1.5 mL) was then collected from the tip of the infusion cannula. The brain was then dissected free and divided into 3 parts; the right hemisphere together with the right midbrain, the left hemisphere together with the left midbrain and the hindbrain (cerebellum, pons and brainstem). Only the right part of the brain was used for subsequent measurements because perfusion via the right internal carotid artery preferentially supplies the right hemisphere and right midbrain (the left hemisphere and hindbrain receive a variable collateral perfusion). The brain tissue samples from each animal were frozen at −30° C., homogenized and weighed aliquots analysed by LC-MS to give total brain concentration. The analysis was carried out using the Micromass Triple Quad instrument. The mobile phase consisted of an acetonitrile/water gradient (containing 0.05% Formic acid) and the column was a Phenomenex Luna CN.

Small aliquots from each brain tissue sample and the corresponding infusion solution were analysed by liquid scintillation counting to determine the level of $^{14}C$-sucrose. The residual vascular space (RVS) in each brain tissue sample was calculated by dividing the measured concentration of sucrose in brain tissue (dpm/mg) by its concentration in the corresponding infusion solution (dpm/µL). This is the volume of fluid that remains inside blood vessels at the end of each perfusion. Multiplying this RVS by the concentration of the test compound in the infusion solution gives the total residual amount of the test compound that is present inside blood vessels in each brain tissue sample (ie: that which has not crossed the BBB). Subtracting this from the total brain concentration gives the amount of drug in each brain tissue sample that is outside the blood vessels (ie: which has crossed the BBB). Dividing this RVS-corrected brain concentration gives the brain uptake ratio (Equation. 1).

$$\text{Brain Uptake Ratio} = \frac{[\text{brain } ng \cdot mg^{-1}] - [RVS\ ng \cdot \mu l^{-1}]}{[\text{infusion solution } ng \cdot \mu L^{-1}]}. \quad \text{Equation 1}$$

A total of 5-6 brain perfusion experiments were performed for each of the test compounds and mean brain uptake ratios were calculated.

Ratios of greater than 50% indicate compounds that enter the brain extremely rapidly; ratios between 10 and 50% indicate compounds that enter the brain well; ratios less than 10% (not observed) would indicate compounds that enter the brain very slowly and would not be suitable for therapeutic administration; ratios less than 1% (not observed) would indicate compounds that are effectively excluded from the brain.

Assay 15. Transgenic Mouse Brain Immunohistochemistry

The APP2576 transgenic mouse (Hsiao et al., 1996) as referred to in Assay 11 were utilized in this assay. The contralateral formalin-fixed mouse brain tissue was coronally cut. Sections (10 µm) were taken from the corresponding sites and treated with 80% formic acid for antigen retrieval. The primary antibody used was monoclonal antibody 1E8, which recognizes epitopes between residues 18 and 22 of Aβ (SmithKline Beecham, UK). Immunoreactivity was developed with secondary antibody linked to horseradish peroxidase (using a 3,39-diaminobenzidinechromagen) (Dako) and alkaline phosphatase (using 5-bromo-4-chloro 3-indoxyl phosphate and nitroblue tetrazolium chloride chromagen) (Dako). Plaque abundance per section was assessed by two operators blinded to treatment according to the following scale:

0=no plaques apparent
1=plaques present but very sparse
2=several plaques present
3=numerous plaques visible in restricted areas
4=plaques abundant and not restricted to any particular area.

Intermediate values eg 2.5 were assigned where applicable. Students' t 'test was used for comparisons between groups.

Assay 16. Pharmacokinetic Profile (a) PBT-1033

Intravenous infusion of PBT-1033; 2 mg/Kg (1 mL of a 0.5 mg/mL solution in 7.5% DMSO with 0.1 m Captisol in Citrate Buffer adjusted to pH 3.0) was administered over 5 minutes to 2 rats and arterial blood was sampled up to 24 hours.

Oral administration of PBT-1033; 30 mg/Kg (as a suspension in CMC-SSV*) via administered via oral gavage to 2 rats and arterial blood was sampled up to 26 hours.

* Standard Suspending Vehicle—0.5% w/v Na-Carboxymethyl Cellulose (CMC), 5% v/v benzyl alcohol, 4% v/v Tween 80 in 0.9% NaCl.

Plasma concentrations of PBT-1033 were determined by LCMS (LOQ 3.7 nM). For rat 020710-D, an overlapping peak was present for PBT-1033.

$$CL_{total} = \frac{Dose_{IV}}{AUC_{IV}}$$

$$V_{d\beta} = \frac{CL_{total}}{\beta}$$

$$BA(\%) = \frac{AUC_{oral} * Dose_{IV}}{AUC_{IV} * Dose_{oral}}$$

Figure 4A:
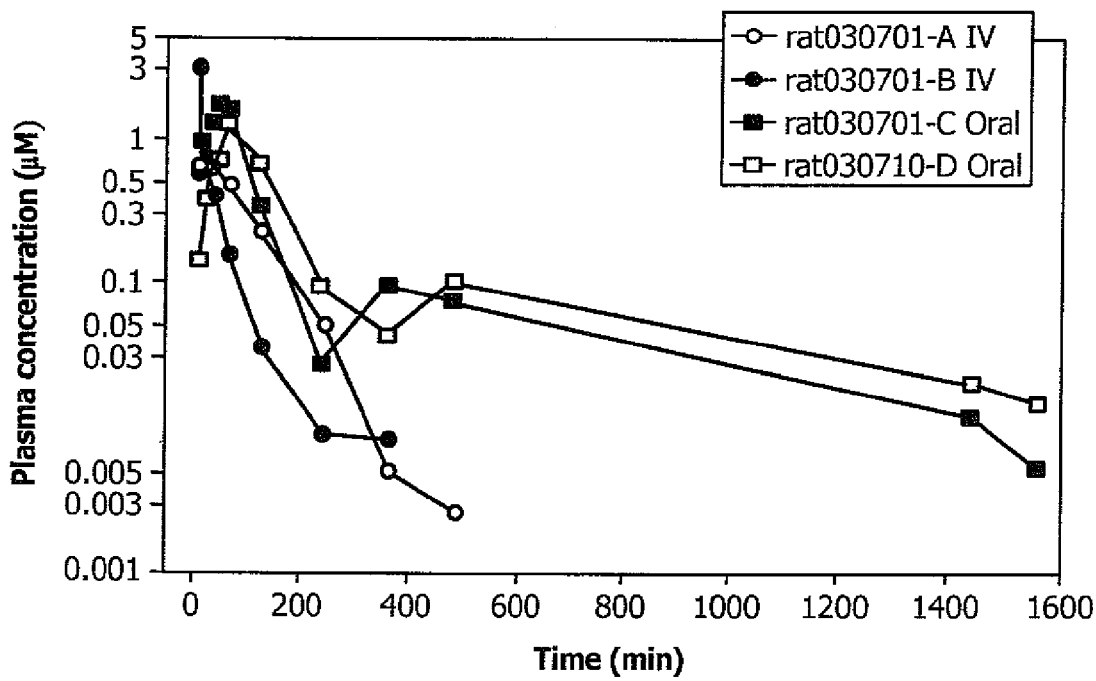
FIG. 4(a) is a graph showing the dose normalised plasma concentrations of PBT 1033 following IV (2 mg/Kg) and oral (30 mg/Kg) administration to rats.

Calculations:
$CL_{total}$=total plasma clearance after IV administration
$V_{d\beta}$=volume of distribution during the elimination phase after IV administration
BA=oral bioavailability
$AUC_{IV}$=area under the plasma concentration versus time profile from zero to infinity after IV administration
$AUC_{oral}$=area under the plasma concentration versus time profile from zero to infinity after oral administration
$\beta$=terminal elimination rate constant after IV administration The results are shown in FIG. 4(a).

(b) PBT-1038

Intravenous infusion of PBT-1038; (0.5 mg/Kg in 7.5% DMSO in Citrate Buffer pH 3.0) was administered over 5 minutes to 2 rats and arterial blood was sampled up to 24 hours.

Oral administration of PBT-1038; (30 mg/Kg as a 0.05% CMC suspension) via administered via oral gavage to 2 rats and arterial blood was sampled up to 24 hours.

Plasma concentrations of PBT-1038 were determined by MS (LOQ 3 nM)

Calculations.

As described above for PBT-1033.

Figure 4B:
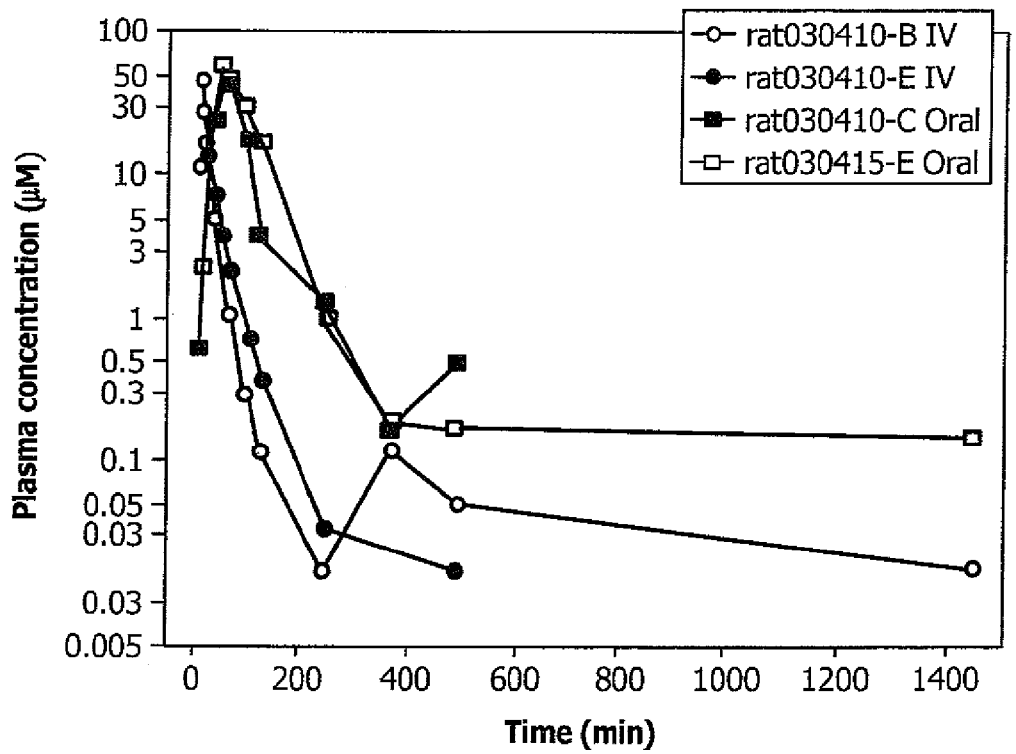
FIG. 4(b) is a graph showing the dose normalised plasma concentrations of PBT 1038 following IV (2 mg/Kg) and oral (30 mg/Kg) administration to rats.

The results are shown in FIG. 4(b).

(c) PBT-1050

Intravenous infusion of PBT-1050; (2 mg/Kg in 7.5% DMSO in Citrate Buffer pH 3.0) was administered over 5 minutes to 2 rats and arterial blood was sampled up to 24 hours.

Oral administration of PBT-1050; (30 mg/Kg as a 0.05% CMC suspension) was administered via oral gavage to 2 rats and arterial blood was sampled up to 24 hours.

Plasma concentrations of PBT-1050 were determined by MS (LOQ 3 nM)

Figure 4C:
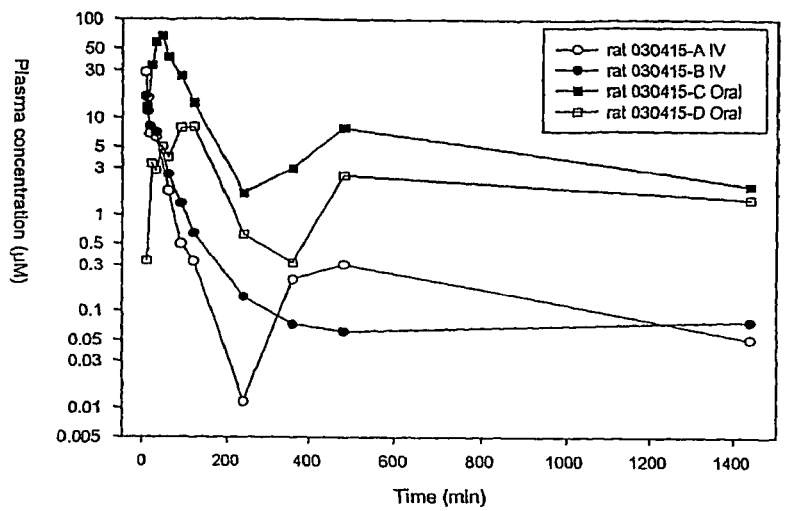
FIG. 4(c) is a graph showing the dose normalised plasma concentrations of PBT 1050 following IV (2 mg/Kg) and oral (30 mg/Kg) administration to rats.

Calculations:
As described above for PBT-1033
The results are shown in FIG. 4(c).

(d) PBT-1051

Intravenous infusion of PBT-1051; 2 mg/Kg (1 mL of a 0.6 mg/mL solution in 7.5% DMSO in Citrate Buffer pH 3.0) was administered over 5 minutes to 2 rats and arterial blood was sampled up to 24 hours.

Oral administration of PBT-1051; 30 mg/Kg (as a suspension in CMC-SSV*) was administered via oral gavage to 2 rats and arterial blood was sampled up to 24 hours.

* Standard Suspending Vehicle—0.5% w/v Na-Carboxymethyl Cellulose (CMC), 5% v/v benzyl alcohol, 4% v/v Tween 80 in 0.9% NaCl.

Plasma concentrations of PBT-1051 were determined by LCMS (LOQ 3.7 nM)

Figure 4D:
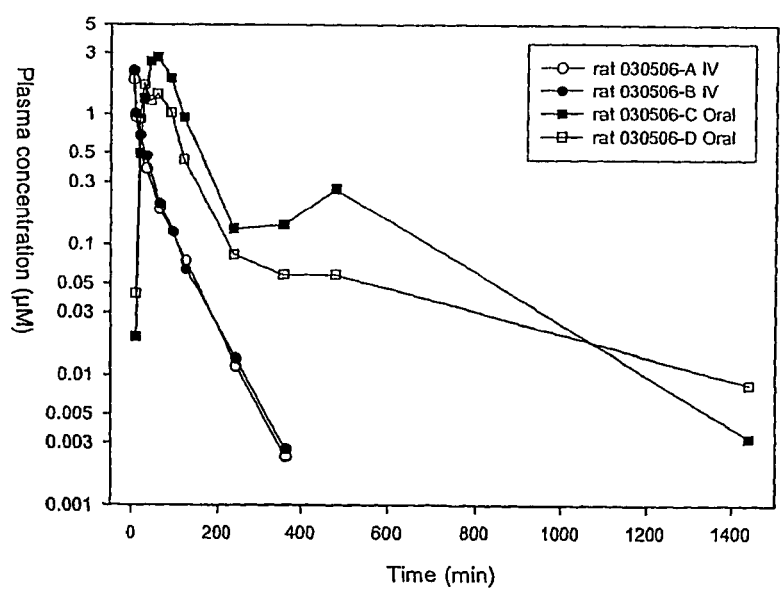
FIG. 4(d) is a graph showing the dose normalised plasma concentrations of PBT 1051 following IV (2 mg/Kg) and oral (30 mg/Kg) administration to rats.
Figure 5:
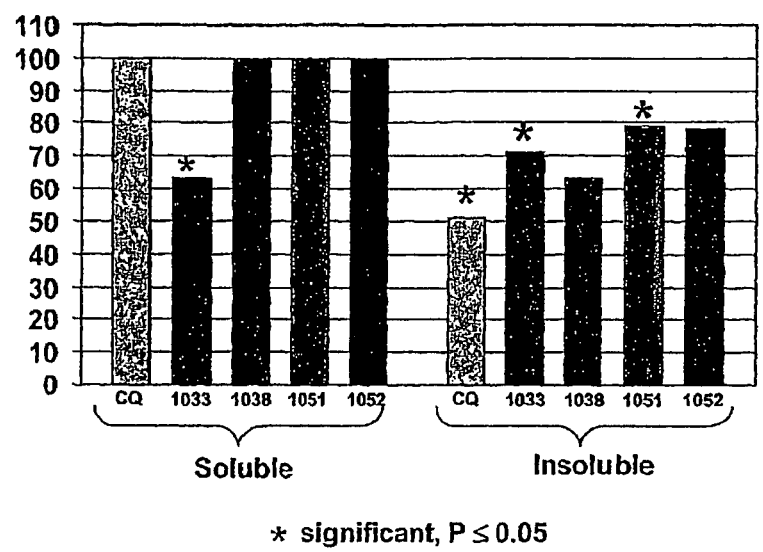
FIG. 5 is a graph summarising the effect of CQ (PBT 1), PBT 1033, PBT 1038, PBT 1051 and PBT 1052 on soluble and insoluble Aβ in transgenic mouse brains [methodology as per assay 11]
Figure 6:
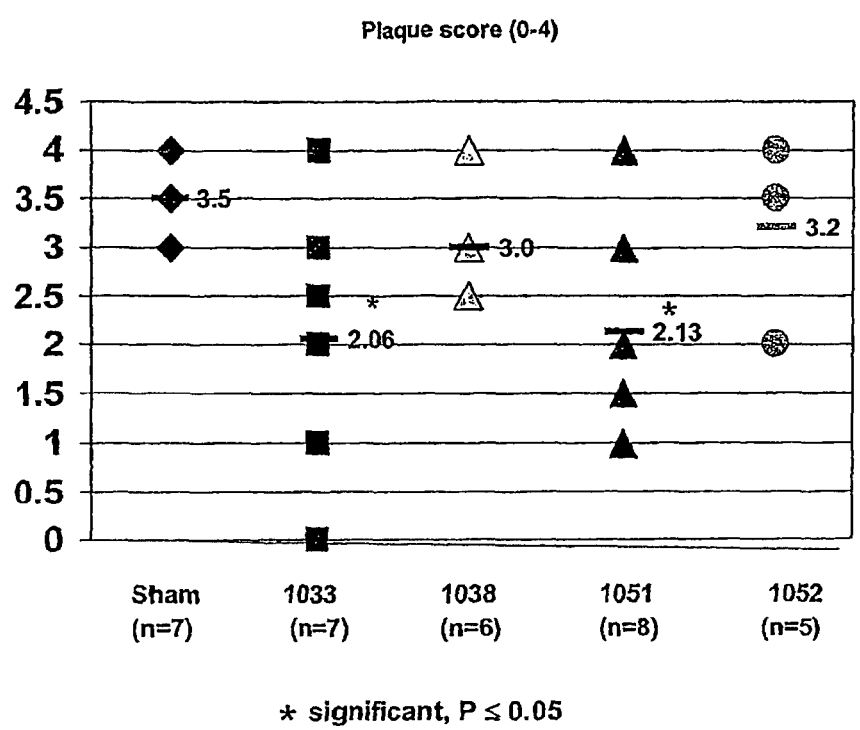
FIG. 6 is a graph showing the immunohistochemistry of PBT 1033, PBT 1038, PBT 1051 and PBT 1052 on amyloid plaque abundance in transgenic mice brains [methodology as per assay 15]

Calculations:
As described above for PBT-1033.
The results are shown in FIG. 4(d).

TABLE 6

Screening Tests of Compound of formula I or II for the treatment of Alzheimer's disease.

| Table 6 Parameter | Assay |
|---|---|
| Sol. (Y,C,N) | Assay 1 |
| clogP | Assay 13 |
| Peroxide IC50 | Assay 1 |
| Viable 10 uM | Assay 8 |
| BAS score | Assay 9 |

N/A = not assayed.
− = not effective at solubilising plaques relative to PBS.
+ = effective at solubilising plaques at more than 1 concentration relative to PBS.
++ = extremely effective at solubilising plaques relative to PBS. This would mean better than twice the amount of PBS at most concentrations tested on each of 2 or more experiments The results of screening tests referred to in Table 6 with respect to compounds of Formula IIA-VIb are tabulated hereinbelow.

| ID | Structure | CAS | Sol (Y, C, N) | clogp | Peroxide IC50 | Viable 10 uM | BAS Score |
|---|---|---|---|---|---|---|---|
| | | Formula IIa | | | | | |
| 49 | 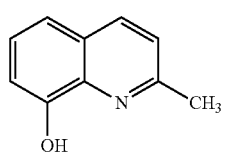 | 826-81-3 | Y | 2.58 | 100 | | N/A |

-continued
| ID | Structure | CAS | Sol (Y, C, N) | clogp | Peroxide IC50 | Viable 10 uM | BAS Score |
|---|---|---|---|---|---|---|---|
| 89 | 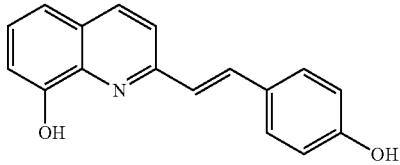 [SMILES: Oc1ccc(/C=C/c2ccc3cccc(O)c3n2)cc1] | 189506-06-7 | Y | 3.7 | 3, 2.5 | | + |
| 89 | | | | | | 74.28 | |
| 91 | 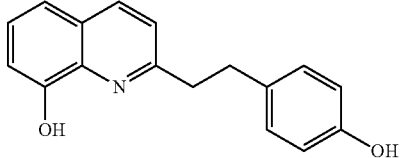 [SMILES: Oc1ccc(CCc2ccc3cccc(O)c3n2)cc1] | | Y | 3.86 | 50, >10 | | N/A |
| 1004 | 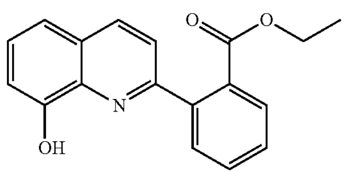 [SMILES: CCOC(=O)c1ccccc1-c1ccc2cccc(O)c2n1] | | | | >10, 6.6 | | N/A |
| 1005 | 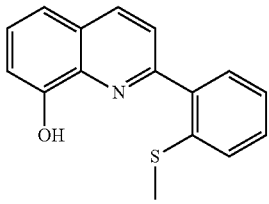 [SMILES: CSc1ccccc1-c1ccc2cccc(O)c2n1] | | | | 2.4 | | N/A |
| 1006 | 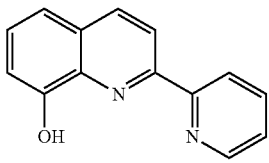 [SMILES: Oc1cccc2ccc(-c3ccccn3)nc12] | | | | 0.53 | | ++ |
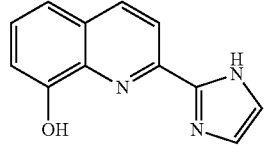 [SMILES: Oc1cccc2ccc(-c3ncc[nH]3)nc12]
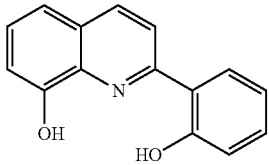 [SMILES: Oc1ccccc1-c1ccc2cccc(O)c2n1]
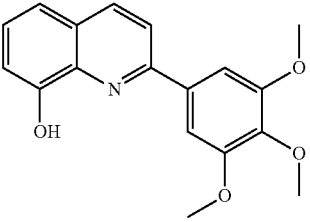 [SMILES: COc1cc(-c2ccc3cccc(O)c3n2)cc(OC)c1OC]

-continued

| ID | Structure | CAS | Sol (Y, C, N) | clogp | Peroxide IC50 | Viable 10 uM | BAS Score |
|---|---|---|---|---|---|---|---|
| | (8-OR-quinolin-2-yl)(3,4,5-trimethoxyphenyl) structure | | | | | | |
| 1007 | 8-hydroxy-2-(6-methylpyridin-2-yl)quinoline | | | | 0.58 | | N/A |
| 1019 | 8-hydroxy-N-(thiazol-2-ylmethyl)quinoline-2-carboxamide | | | | >10, >10 | | N/A |
| 1020 | 8-hydroxy-N,N-bis(pyridin-2-ylmethyl)quinoline-2-carboxamide | | | | 1.3 | | N/A |
| 1021 | N-acetyl-8-hydroxyquinoline-2-carboxamide | | | | 0.27 | | N/A |
| 1029 | 8-hydroxyquinoline-2-carboxamide | | | | N/A | | N/A |

-continued

| ID | Structure | CAS | Sol (Y, C, N) | clogp | Peroxide IC50 | Viable 10 uM | BAS Score |
|---|---|---|---|---|---|---|---|
| 1035 | | | | | >10 | | N/A |

Formula IIIa

| ID | Structure | CAS | Sol (Y, C, N) | clogp | Peroxide IC50 | Viable 10 uM | BAS Score |
|---|---|---|---|---|---|---|---|
| 52 | 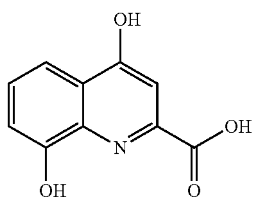 [SMILES: O=C(O)c1cc(O)c2cccc(O)c2n1] | 59-00-7 | Y | 3 | >100 | | N/A |
| 57 | 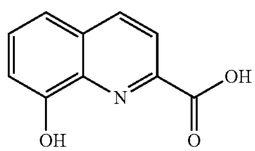 [SMILES: O=C(O)c1ccc2cccc(O)c2n1] | 1571-30-8 | Y | 2.67 | 40 | | N/A |
| 58 | 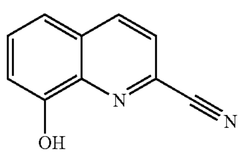 [SMILES: N#Cc1ccc2cccc(O)c2n1] | 6759-78-0 | Y | 1.95 | 100 | | N/A |
| 95 | 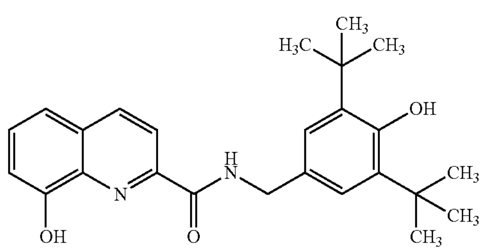 [SMILES: CC(C)(C)c1cc(CNC(=O)c2ccc3cccc(O)c3n2)cc(C(C)(C)C)c1O] | | Y | 6.66 | 10 | | N/A |
| 948 | | | Y | 1.61 | 0.19, 0.15 | | + |
| 948 | | | | | | | 106.66 |

| ID | Structure | CAS | Sol (Y, C, N) | clogp | Peroxide IC50 | Viable 10 uM | BAS Score |
|---|---|---|---|---|---|---|---|
| 949 | | | Y | 2.38 | 0.43, 0.9 | | + |
| 949 | | | | | | 84.82 | |
| 950 | | | Y | 2.51 | 0.25, 0.15 | | + |
| 950 | | | | | | 92.8 | |
| 951 | | | Y | 3.26 | 1.43 | | − |
| 951 | | | | | | 91.86 | |
| 952 | | | C | 2.47 | <0.81, 0.27 | | + |
| 952 | | | | | | 99.52 | |
| 953 | | | C | 2.97 | <4.24, 0.62 | | + |
| 953 | | | | | | 67.8 | |

-continued

| ID | Structure | CAS | Sol (Y, C, N) | clogp | Peroxide IC50 | Viable 10 uM | BAS Score |
|---|---|---|---|---|---|---|---|
| 954 | | | Y | 1.93 | 0.18, 0.12 | | – |
| 954 | | | | | | 104.9 | |
| 955 | | | Y | 2.71 | 0.26, 0.18 | | – |
| 955 | | | | | | 100 | |
| 956 | | 125686-78-4 | Y | 1.7 | >10 | | N/A |
| 956 | | | | | | 89 | |
| 957 | | | Y | 1.42 | >10 | | + |
| 957 | | | | | | 95.86 | |
| 976 | 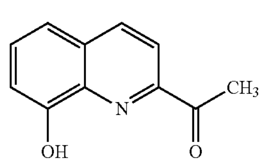 | 149003-37-2 | Y | 2.35 | 3.7 | | – |

-continued

| ID | Structure | CAS | Sol (Y, C, N) | clogp | Peroxide IC50 | Viable 10 uM | BAS Score |
|---|---|---|---|---|---|---|---|
| 986 | | | Y | 2.8 | 3.6 | | + |
| 986 | | | | | | 81.73 | |
| 987 | | | Y | 1.08 | 1.8 | | + |
| 987 | | | | | | 89.03 | |
| 988 | | | Y | 1.76 | >10 | | − |
| 988 | | | | | | 93.27 | |
| 992 | 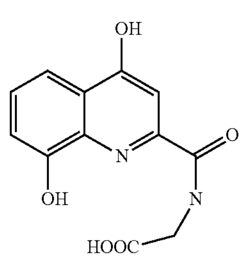 [SMILES: O=C(O)CNC(=O)c1cc(O)c2cccc(O)c2n1] | | Y | 2.03 | >10 | | N/A |

|  |  |  |  |  |  |  |  |
|---|---|---|---|---|---|---|---|
| ID | Structure | CAS | Sol (Y, C, N) | clogp | Peroxide IC50 | Viable 10 uM | BAS Score |
| | 8-hydroxyquinoline-2-thiocarboxamide (N-R) | | | | | | |
| | 5,7-dihalo-8-hydroxyquinoline-2-carboxamide (N-R₁) | | | | | | |
| | 8-hydroxyquinoline-2-carboxamide (N(R₃)R₃) | | | | | | |
| | | Formula IVa | | | | | |
| 966 | 8-hydroxyquinolin-2-ylmethyl guanidine | | Y | 0.2 | 4.3 | | + |
| 966 | | | | | | 88.61 | |
| 967 | N-((8-hydroxyquinolin-2-yl)methyl)acetamide | | Y | 0.89 | 7.8 | | N/A |
| 967 | | | | | | 90.69 | |
| 968 | (8-hydroxyquinolin-2-yl)methanamine | 17018-81-4 | Y | 1.03 | 0.26 | | ++ |
| 968 | | | | | | 97.12 | |
| 969 | 8-hydroxyquinoline-2-carbaldehyde oxime | 5603-22-5 | Y | 2.83 | 0.54 | | + |

-continued
| ID | Structure | CAS | Sol (Y, C, N) | clogp | Peroxide IC50 | Viable 10 uM | BAS Score |
|---|---|---|---|---|---|---|---|
| 969 | | | | | | 94.55 | |
| 989 | 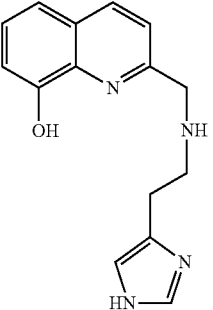 [SMILES: Oc1cccc2ccc(CNCCc3c[nH]cn3)nc12] | | Y | 1.14 | 0.42 | | − |
| 989 | | | | | | 43.24 | |
| 990 | 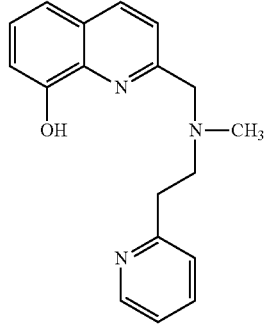 [SMILES: CN(CCc1ccccn1)Cc1ccc2cccc(O)c2n1] | | Y | 2.51 | 0.4 | | + |
| 990 | | | | | | 57.45 | |
| 991 | 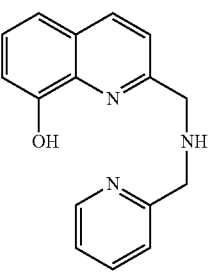 [SMILES: Oc1cccc2ccc(CNCc3ccccn3)nc12] | | Y | 1.11 | 0.47 | | + |
| 1002 | 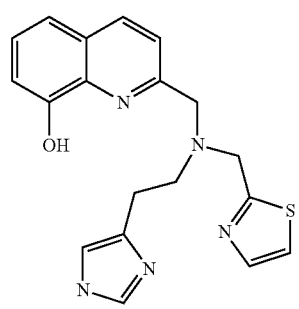 [SMILES: Oc1cccc2ccc(CN(CCc3c[nH]cn3)Cc3nccs3)nc12] | | | 1.95 | 0.39 | | N/A |

-continued

| ID | Structure | CAS | Sol (Y, C, N) | clogp | Peroxide IC50 | Viable 10 uM | BAS Score |
|---|---|---|---|---|---|---|---|
| 1003 | 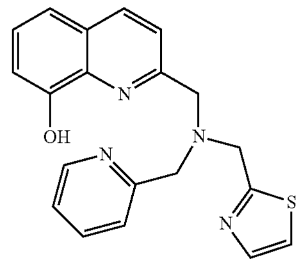 [SMILES: Oc1cccc2ccc(CN(Cc3ccccn3)Cc3nccs3)nc12] | | | 2.19 | 0.55 | | N/A |
| 1008 | 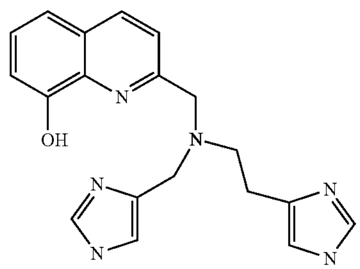 | | | 1.2 | 0.26 | | N/A |
| 1009 | 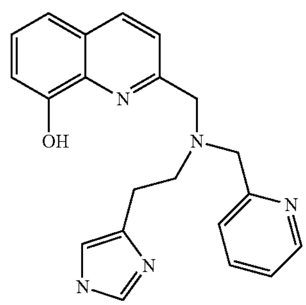 [SMILES: Oc1cccc2ccc(CN(CCc3c[nH]cn3)Cc3ccccn3)nc12] | | | 1.88 | 0.32 | | N/A |
| 1010 | 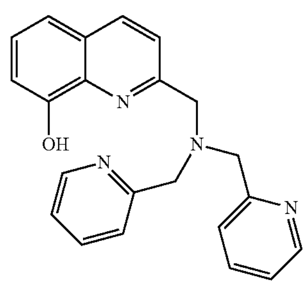 [SMILES: Oc1cccc2ccc(CN(Cc3ccccn3)Cc3ccccn3)nc12] | | | 2.35 | 0.33 | | N/A |
| 1011 | 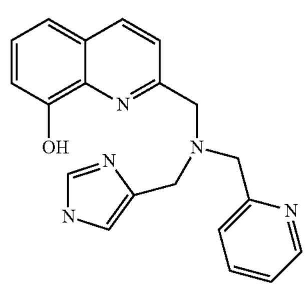 [SMILES: Oc1cccc2ccc(CN(Cc3ccccn3)Cc3c[nH]cn3)nc12] | | | 1.68 | 0.32 | | N/A |

-continued

| ID | Structure | CAS | Sol (Y, C, N) | clogp | Peroxide IC50 | Viable 10 uM | BAS Score |
|---|---|---|---|---|---|---|---|
| | | | | | | | |

Formula Va

| ID | Structure | CAS | Sol (Y, C, N) | clogp | Peroxide IC50 | Viable 10 uM | BAS Score |
|---|---|---|---|---|---|---|---|
| 53 | | 82361-90-8 | Y | 6.27 | 0.3 | | + |
| 53 | | | | | | 95.8 | |
| 54 | | 70125-16-5 | Y | 1.75 | 1 | | + |
| 54 | | | | | | 99.57 | |
| 56 | 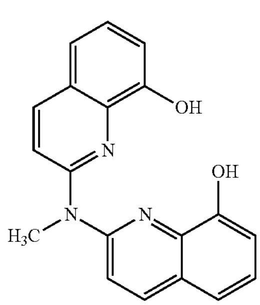 [SMILES: CN(c1ccc2cccc(O)c2n1)c1ccc2cccc(O)c2n1] | 65165-14-2 | Y | 4.69 | 0.7, 0.25 | | + |

-continued

| ID | Structure | CAS | Sol (Y, C, N) | clogp | Peroxide IC50 | Viable 10 uM | BAS Score |
|---|---|---|---|---|---|---|---|
| 56 | | | | | | 24.61 | |
| 56 | | | | | | 100.6 | |
| 964 | 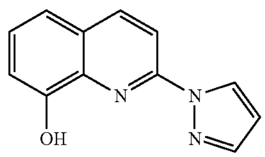 [SMILES: Oc1cccc2ccc(-n3cccn3)nc12] | | Y | 2.97 | 7.1 | | N/A |
| 965 | 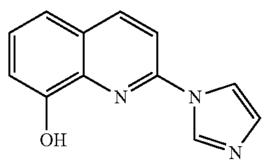 [SMILES: Oc1cccc2ccc(-n3ccnc3)nc12] | | Y | 1.94 | >10 | | N/A |
| 993 | 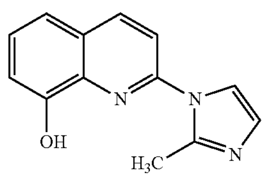 [SMILES: Cc1nccn1-c1ccc2cccc(O)c2n1] | | Y | 2.21 | >10 | | N/A |
| 994 | 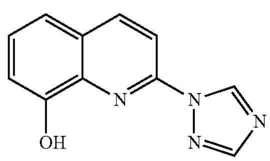 [SMILES: Oc1cccc2ccc(-n3cncn3)nc12] | | Y | 1.75 | >10 | | N/A |

-continued

| ID | Structure | CAS | Sol (Y, C, N) | clogp | Peroxide IC50 | Viable 10 uM | BAS Score |
|---|---|---|---|---|---|---|---|
| | *Formula VIa* | | | | | | |
| 50 | 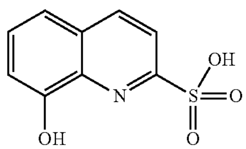 [SMILES: O=S(=O)(O)c1ccc2cccc(O)c2n1] | 20946-17-2 | | 0.71 | 90 | | N/A |
| | *Formula IIb* | | | | | | |

US 9,302,993 B2

115                                                                                       116

-continued

| ID | Structure | CAS | Sol (Y, C, N) | clogp | Peroxide IC50 | Viable 10 uM | BAS Score |
|----|-----------|-----|---------------|-------|---------------|--------------|-----------|

-continued
| ID | Structure | CAS | Sol (Y, C, N) | clogp | Peroxide IC50 | Viable 10 uM | BAS Score |
|---|---|---|---|---|---|---|---|
| 1 | 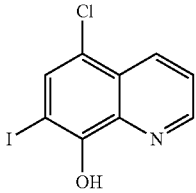 [SMILES: Oc1c(I)cc(Cl)c2cccnc12] | 130-26-7 | Y | 3.73 | 0.4-0.5 | | ++ |
| 41 | 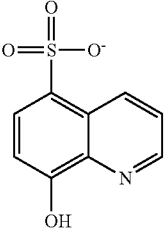 [SMILES: O=S(=O)([O-])c1ccc(O)c2ncccc12] | 84-88-8 | Y | −0.71 | 0.5 | | + |
| 41 | | | | | | 81.33 | |
| 42 | 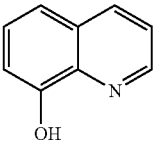 [SMILES: Oc1cccc2cccnc12] | 148-24-3 | Y | 2.08 | 0.7 | | + |
| 42 | | | | | | 97.66 | |
| 43 | 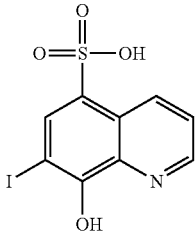 [SMILES: O=S(=O)(O)c1cc(I)c(O)c2ncccc12] | 547-91-1 | Y | 0.19 | 0.6 | | − |
| 43 | | | | | | 91.02 | |
| 44 | 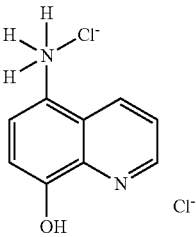 | 21302-43-2 | Y | 1.53 | >10 | 71.05 | + |
| 45 | 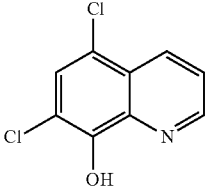 [SMILES: Oc1c(Cl)cc(Cl)c2cccnc12] | 773-76-2 | Y | 3.34 | 0.7, 0.4 | | ++ |
| 45 | | | | | | 75.19 | |
| 45 | | | | | | 66.51 | |

-continued

| ID | Structure | CAS | Sol (Y, C, N) | clogp | Peroxide IC50 | Viable 10 uM | BAS Score |
|---|---|---|---|---|---|---|---|
| 46 | | 83-73-8 | Y | 4.14 | 1 | | − |
| 46 | | | | | | 91.97 | |
| 47 | | 521-74-4 | Y | 3.69 | 0.9, 0.5 | | + |
| 47 | | | | | | 93.59 | |
| 48 | | 130-16-5 | Y | 2.91 | 0.8, 0.8 | | − |
| 48 | | | | | | 85 | |
| 59 | | 37873-29-3 | Y | 3.02 | 0.7 | | + |
| 59 | | | | | | 84.95 | |
| 59 | | | | | | 42.59 | |
| 814 | 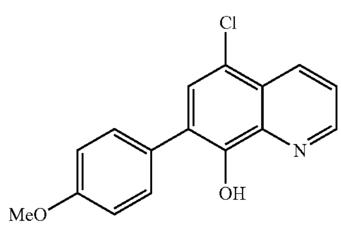 [SMILES: COc1ccc(-c2cc(Cl)c3cccnc3c2O)cc1] | | | | <1.1, >10 | | + |
| 1026 | 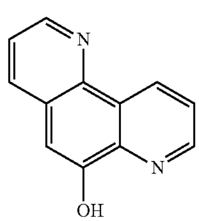 [SMILES: Oc1cc2cccnc2c2cccnc12] | | | | 0.23 | | N/A |

-continued

| ID | Structure | CAS | Sol (Y, C, N) | clogp | Peroxide IC50 | Viable 10 uM | BAS Score |
|---|---|---|---|---|---|---|---|
| 1028 | 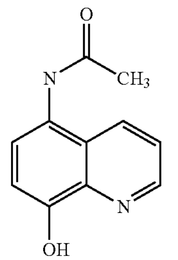 | | | | 0.32 | | N/A |
| 1031 | 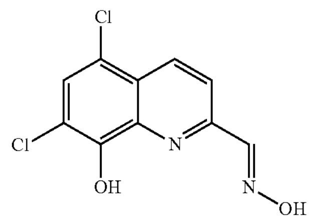 [SMILES: O/N=C/c1ccc2c(Cl)cc(Cl)c(O)c2n1] | | | | 0.76 | | N/A |
| 1032 | 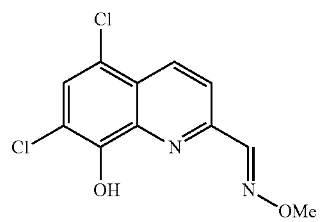 [SMILES: CO/N=C/c1ccc2c(Cl)cc(Cl)c(O)c2n1] | | | | 1 | | N/A |
| 1033 | 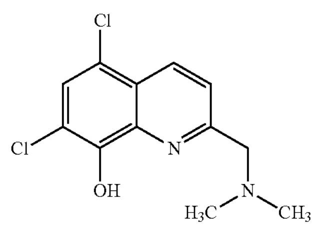 [SMILES: CN(C)Cc1ccc2c(Cl)cc(Cl)c(O)c2n1] | | | | 0.38, 0.35 | | + |
| 1034 | 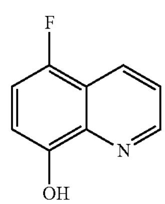 [SMILES: Oc1ccc(F)c2cccnc12] | | | | 0.44 | | N/A |
| 1036 | 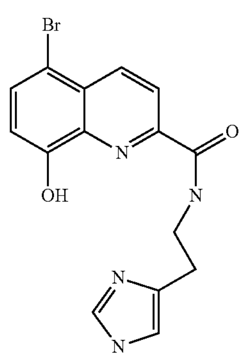 [SMILES: O=C(NCCc1c[nH]cn1)c1ccc2c(Br)ccc(O)c2n1] | | | | >5, 0.24 | | N/A |

-continued
| ID | Structure | CAS | Sol (Y, C, N) | clogp | Peroxide IC50 | Viable 10 uM | BAS Score |
|---|---|---|---|---|---|---|---|
| 1037 | 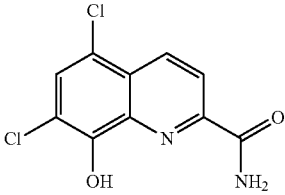 [SMILES: NC(=O)c1ccc2c(Cl)cc(Cl)c(O)c2n1] | | | | >10 | | N/A |
| 1038 | 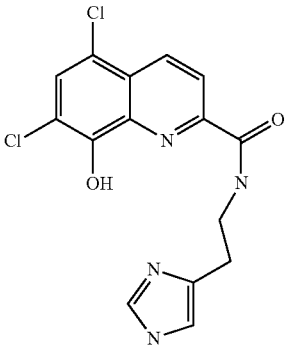 [SMILES: O=C(NCCc1c[nH]cn1)c1ccc2c(Cl)cc(Cl)c(O)c2n1] | | | | 0.26 | | + |
| 1039 | 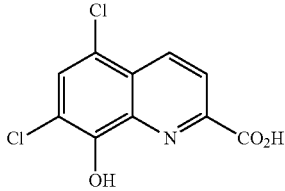 [SMILES: O=C(O)c1ccc2c(Cl)cc(Cl)c(O)c2n1] | | | | >10 | | N/A |
| 1043 | 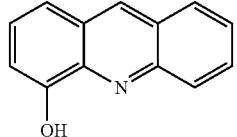 [SMILES: Oc1cccc2cc3ccccc3nc12] | | | | 0.64 | | N/A |
| 1047 | 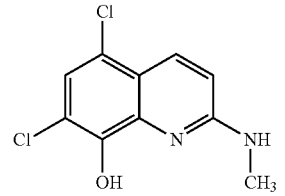 | | | | >10 | | N/A |
| 1050 | 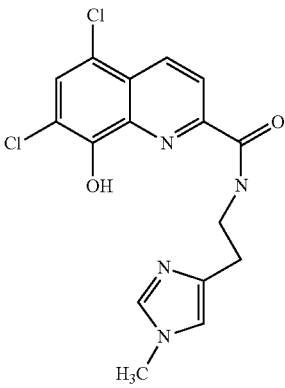 [SMILES: Cn1cnc(CCNC(=O)c2ccc3c(Cl)cc(Cl)c(O)c3n2)c1] | | | | 0.28 | | N/A |

-continued
| ID | Structure | CAS | Sol (Y, C, N) | clogp | Peroxide IC50 | Viable 10 uM | BAS Score |
|---|---|---|---|---|---|---|---|
| 1051 | 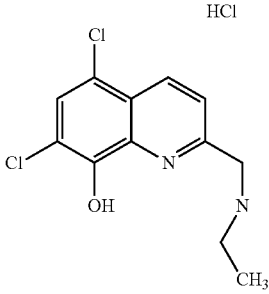 [SMILES: Cl ; CCNCc1ccc2c(Cl)cc(Cl)c(O)c2n1] HCl | | | | 0.38 | | + |
| 1052 | 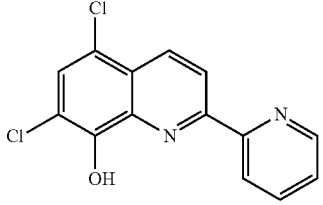 [SMILES: Oc1c(Cl)cc(Cl)c2ccc(-c3ccccn3)nc12] | | | | 0.64 | | + |
| 1056 | 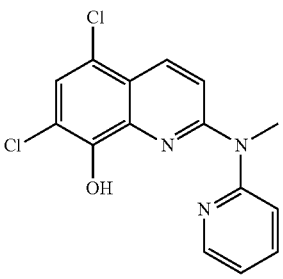 [SMILES: CN(c1ccccn1)c1ccc2c(Cl)cc(Cl)c(O)c2n1] | | | | 0.69 | 68.25 | |
| 1057 | 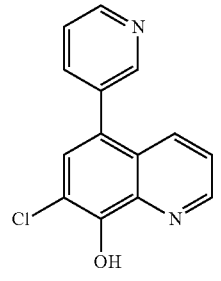 [SMILES: Oc1c(Cl)cc(-c2cccnc2)c2cccnc12] | | | | 0.43 | 95.02 | |
| 1058 | 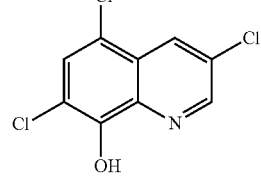 | | | | 0.68 | 54.60 | |
| 1060 | 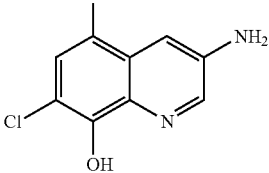 | | | | 0.50 | | |

-continued
| ID | Structure | CAS | Sol (Y, C, N) | clogp | Peroxide IC50 | Viable 10 uM | BAS Score |
|---|---|---|---|---|---|---|---|
| | Formula IIIb | | | | | | |
| 808 | 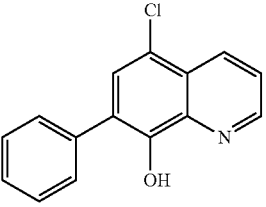 [SMILES: Oc1c(-c2ccccc2)cc(Cl)c2cccnc12] | | C | 4.3 | >10 | | N/A |
| 808 | | | | | | 71.89 | |
| 810 | 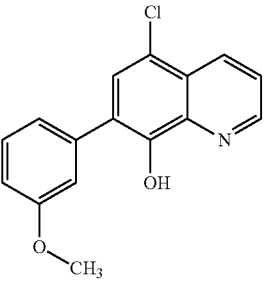 [SMILES: COc1cccc(-c2cc(Cl)c3cccnc3c2O)c1] | | C | 4.23 | >10, <0.7 | | + |
| 810 | | | | | | 70.7 | |
| 810 | | | | | | 90.15 | |
| 811 | 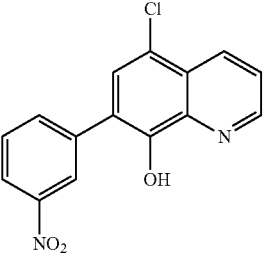 [SMILES: O=[N+]([O-])c1cccc(-c2cc(Cl)c3cccnc3c2O)c1] | | C | 4.06 | >10 | | N/A |
| 811 | | | | | | 78.46 | |
| 812 | 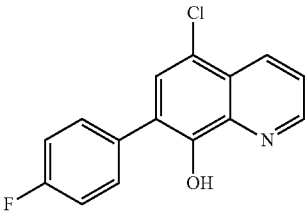 [SMILES: Oc1c(-c2ccc(F)cc2)cc(Cl)c2cccnc12] | | C | 4.45 | >10 | | N/A |
| 812 | | | | | | 75.36 | |
| 813 | 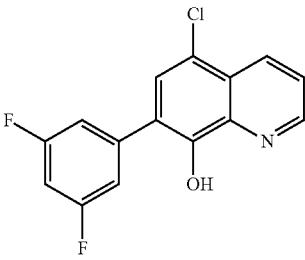 [SMILES: Oc1c(-c2cc(F)cc(F)c2)cc(Cl)c2cccnc12] | | C | 4.6 | >10 | | N/A |
| 813 | | | | | | 8 | |
| 813 | | | | | | | 66 |

-continued
| ID | Structure | CAS | Sol (Y, C, N) | clogp | Peroxide IC50 | Viable 10 uM | BAS Score |
|---|---|---|---|---|---|---|---|
| 814 | 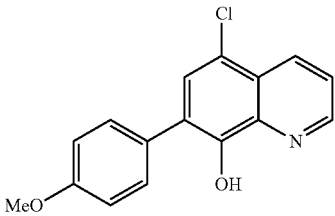 [SMILES: COc1ccc(-c2cc(Cl)c3cccnc3c2O)cc1] | | C | 4.23 | <1.1, >10 | | + |
| 814 | | | | | | 31.13 | |
| 815 | 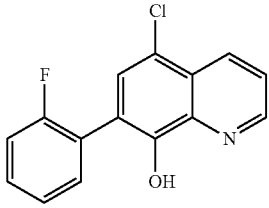 [SMILES: Oc1c(-c2ccccc2F)cc(Cl)c2cccnc12] | | C | 4.45 | >10 | | N/A |
| 815 | | | | | | 53.68 | |
| 849 | 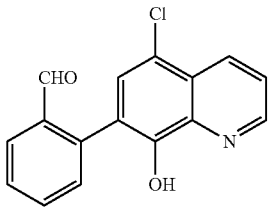 [SMILES: O=Cc1ccccc1-c1cc(Cl)c2cccnc2c1O] | | Y | 3.67 | 4.5 | | N/A |
| 849 | | | | | | 98.83 | |
| 850 | 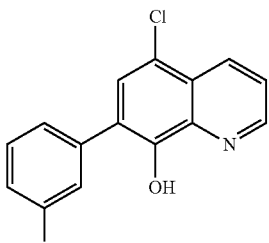 | | C | 4.45 | >10 | | N/A |
| 850 | | | | | | 71.28 | |
| 851 | 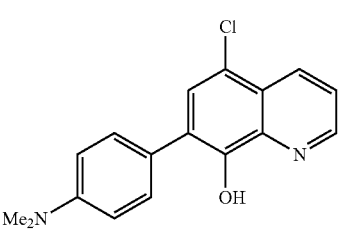 [SMILES: CN(C)c1ccc(-c2cc(Cl)c3cccnc3c2O)cc1] | | C | 4.47 | <0.7 | | − |
| 851 | | | | | | 84.92 | |
| 851 | | | | | | 86.08 | |

-continued

| ID | Structure | CAS | Sol (Y, C, N) | clogp | Peroxide IC50 | Viable 10 uM | BAS Score |
|---|---|---|---|---|---|---|---|
| 854 | | | C | 4.5 | <0.78 | | + |
| 854 | | | | | | 100 | |
| 854 | | | | | | 71.39 | |
| 854 | | | | | | 34.95 | |
| 859 | | | C | 4.8 | <0.67 | | + |
| 859 | | | | | | 73.14 | |
| 859 | | | | | | 36.01 | |
| 859 | | | | | | 34.07 | |
| 864 | | | Y | 5.2 | 0.77 | | + |
| 864 | | | | | | 93.12 | |
| 947 | | | Y | 3.14 | 1.14 | | + |
| 947 | | | | | | 70.4 | |
| 970 | | | C | 5.54 | 6.7 | | N/A |
| 970 | | | | | | 32.33 | |

-continued

| ID | Structure | CAS | Sol (Y, C, N) | clogp | Peroxide IC50 | Viable 10 uM | BAS Score |
|---|---|---|---|---|---|---|---|
| 971 | | | C | 4.57 | >10 | | N/A |
| 971 | | | | | | 84.29 | |
| 972 | | | C | 3.95 | >10 | | N/A |
| 972 | | | | | | 30.59 | |
| 973 | | | C | 4.6 | >10 | | N/A |
| 973 | | | | | | 42.38 | |
| | | Formula IVb | | | | | |
| 806 | | | C | 4.67 | <1.2, <0.9 | | ++ |
| 806 | | | | | | 97 | |
| 806 | | | | | | 100 | |
| 853 | | | Y | 4.97 | 0.77 | | + |
| 853 | | | | | | 94.79 | |

-continued
| ID | Structure | CAS | Sol (Y, C, N) | clogp | Peroxide IC50 | Viable 10 uM | BAS Score |
|---|---|---|---|---|---|---|---|
| 860 | 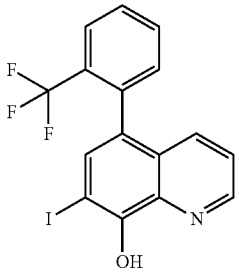 [SMILES: Oc1c(I)cc(-c2ccccc2C(F)(F)F)c2cccnc12] | | Y | 5.76 | 0.79 | | + |
| 860 | | | | | | 89.58 | |
| 860 | | | | | | 64.83 | |
| 861 | 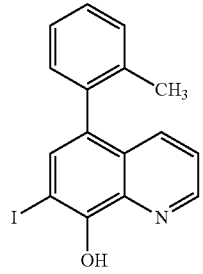 | | C | 5.06 | 0.91 | | + |
| 861 | | | | | | 37.83 | |
| 863 | 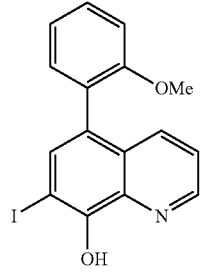 | | C | 4.23 | <0.73 | | + |
| 863 | | | | | | 34.97 | |
| 865 | 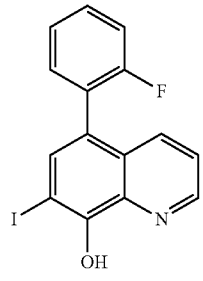 | | C | 5.01 | >10 | | N/A |
| 865 | | | | | | 34.07 | |

-continued

| ID | Structure | CAS | Sol (Y, C, N) | clogp | Peroxide IC50 | Viable 10 uM | BAS Score |
|---|---|---|---|---|---|---|---|
| | | Formula Vb | | | | | |
| 809 | | | C | 5.35 | <4, 1.8 | | + |
| 809 | | | | | | 26.31 | |
| 852 | | | Y | 5.75 | 2.1 | | + |
| 852 | | | | | | 33.52 | |
| 862 | | | C | 4.09 | <0.77 | | + |
| 862 | | | | | | 51.52 | |
| 862 | | | | | | 52.69 | |
| 974 | 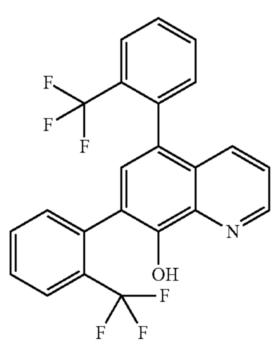 [SMILES: Oc1c(-c2ccccc2C(F)(F)F)cc(-c2ccccc2C(F)(F)F)c2cccnc12] | | Y | 7.17 | 0.6 | | + |

-continued

| ID | Structure | CAS | Sol (Y, C, N) | clogp | Peroxide IC50 | Viable 10 uM | BAS Score |
|---|---|---|---|---|---|---|---|
| 975 | | | Y | 5.67 | 3.2 | | + |

Formula VIb

| ID | Structure | CAS | Sol (Y, C, N) | clogp | Peroxide IC50 | Viable 10 uM | BAS Score |
|---|---|---|---|---|---|---|---|
| 39 | Chiral | 14683-61-5 | Y | | 90 | | N/A |
| 62 | 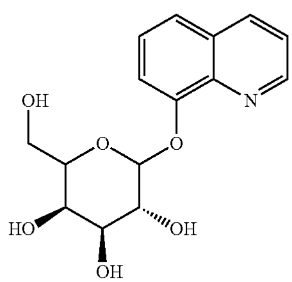 [SMILES: OCC1OC(Oc2cccc3cccnc23)[C@H](O)[C@@H](O)[C@H]1O] | 29266-96-4 | Y | | >10 | | N/A |
| 800 | 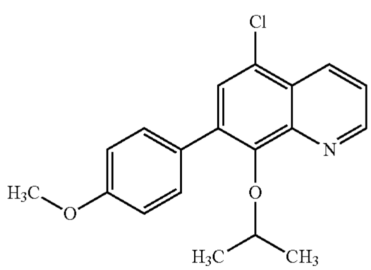 [SMILES: COc1ccc(-c2cc(Cl)c3cccnc3c2OC(C)C)cc1] | | C | | >10 | | N/A |
| 801 | 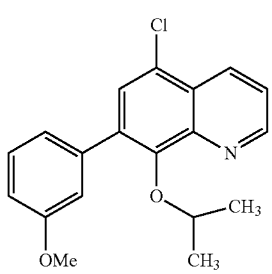 [SMILES: COc1cccc(-c2cc(Cl)c3cccnc3c2OC(C)C)c1] | | C | | >10 | | N/A |

-continued

| ID | Structure | CAS | Sol (Y, C, N) | clogp | Peroxide IC50 | Viable 10 uM | BAS Score |
|---|---|---|---|---|---|---|---|
| 802 | 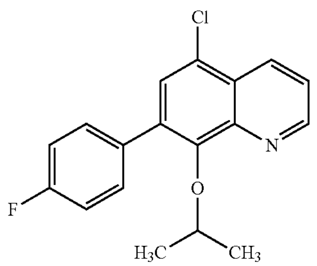 [SMILES: CC(C)Oc1c(-c2ccc(F)cc2)cc(Cl)c2cccnc12] | | C | | >10 | | N/A |
| 803 | 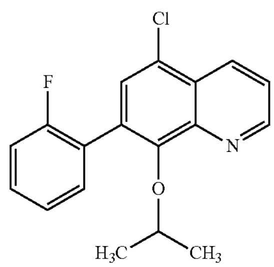 [SMILES: CC(C)Oc1c(-c2ccccc2F)cc(Cl)c2cccnc12] | | C | | >10 | | N/A |
| 804 | 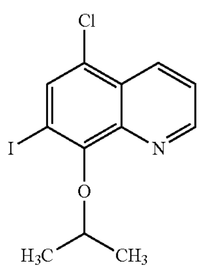 [SMILES: CC(C)Oc1c(I)cc(Cl)c2cccnc12] | | C | | >10 | | N/A |
| 805 | 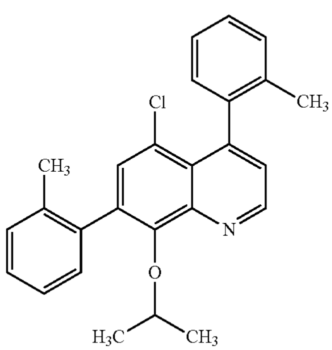 [SMILES: Cc1ccccc1-c1cc(Cl)c2c(-c3ccccc3C)ccnc2c1OC(C)C] | | C | | >10 | | N/A |
| 807 | 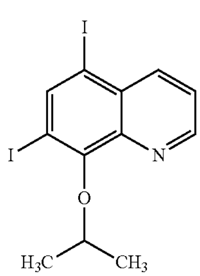 [SMILES: CC(C)Oc1c(I)cc(I)c2cccnc12] | | C | | >10 | | N/A |

-continued
| ID | Structure | CAS | Sol (Y, C, N) | clogp | Peroxide IC50 | Viable 10 uM | BAS Score |
|---|---|---|---|---|---|---|---|
| 816 | 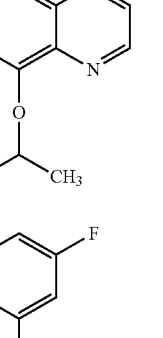 | | C | | >10 | | N/A |
| 817 | 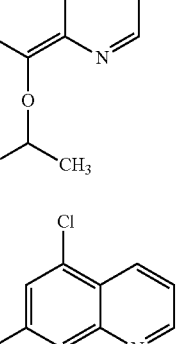 | | C | | >10 | | N/A |
| 818 | 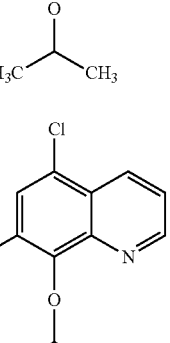 | | C | | >10 | | N/A |
| 819 | 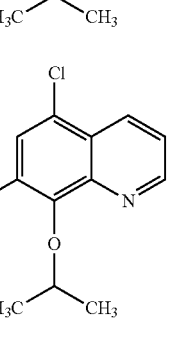 | | C | | >10 | | N/A |
| 820 | 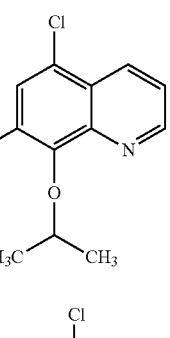 | | C | | >10 | | N/A |

-continued

| ID | Structure | CAS | Sol (Y, C, N) | clogp | Peroxide IC50 | Viable 10 uM | BAS Score |
|---|---|---|---|---|---|---|---|
| 821 | 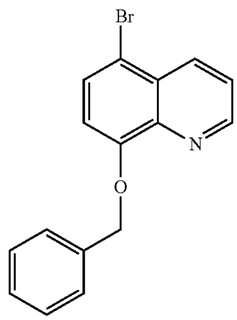 [SMILES: Brc1ccc(OCc2ccccc2)c2ncccc12] | | C | | >10 | | N/A |
| 822 | 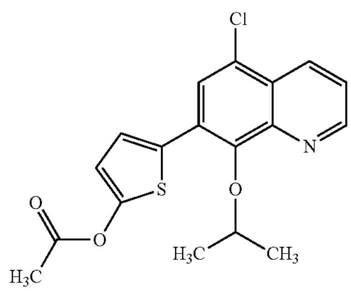 [SMILES: CC(=O)Oc1ccc(-c2cc(Cl)c3cccnc3c2OC(C)C)s1] | | C | | >10 | | N/A |
| 823 | 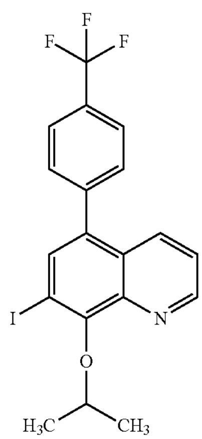 [SMILES: CC(C)Oc1c(I)cc(-c2ccc(C(F)(F)F)cc2)c2cccnc12] | | C | | >10 | | N/A |
| 824 | 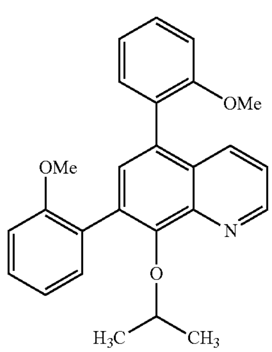 [SMILES: COc1ccccc1-c1cc(-c2ccccc2OC)c2cccnc2c1OC(C)C] | | C | | >10 | | N/A |

-continued
| ID | Structure | CAS | Sol (Y, C, N) | clogp | Peroxide IC50 | Viable 10 uM | BAS Score |
|---|---|---|---|---|---|---|---|
| 825 | 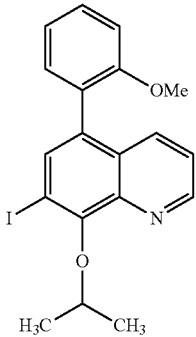 [SMILES: COc1ccccc1-c1cc(I)c(OC(C)C)c2ncccc12] | | C | | >10 | | N/A |
| 826 | 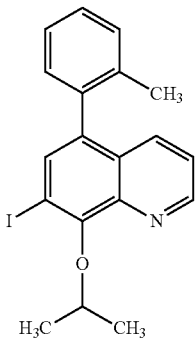 [SMILES: Cc1ccccc1-c1cc(I)c(OC(C)C)c2ncccc12] | | C | | >10 | | N/A |
| 827 | 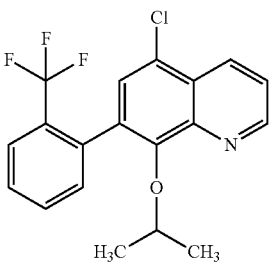 [SMILES: CC(C)Oc1c(-c2ccccc2C(F)(F)F)cc(Cl)c2cccnc12] | | C | | >10 | | N/A |
| 855 | 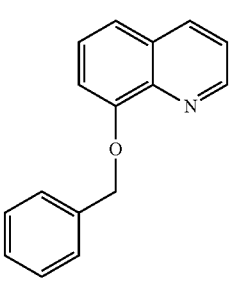 [SMILES: c1ccc(COc2cccc3cccnc23)cc1] | | Y | | >10 | | N/A |
| 856 | 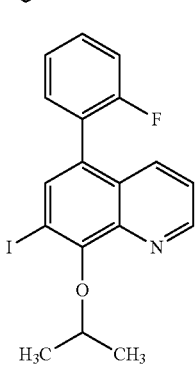 | | C | | >10 | | N/A |

| ID | Structure | CAS | Sol (Y, C, N) | clogp | Peroxide IC50 | Viable 10 uM | BAS Score |
|---|---|---|---|---|---|---|---|
| 857 | 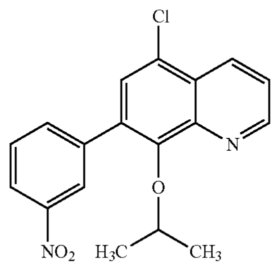 [SMILES: CC(C)Oc1c(-c2cccc([N+](=O)[O-])c2)cc(Cl)c2cccnc12] | | C | | >10 | | N/A |
| 858 | 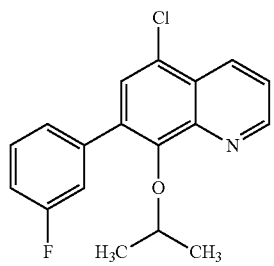 [SMILES: CC(C)Oc1c(-c2cccc(F)c2)cc(Cl)c2cccnc12] | | Y | | >10 | | N/A |
| 866 | 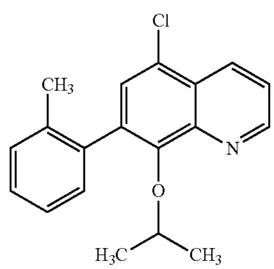 [SMILES: Cc1ccccc1-c1cc(Cl)c2cccnc2c1OC(C)C] | | Y | | >10 | | N/A |
| 867 | 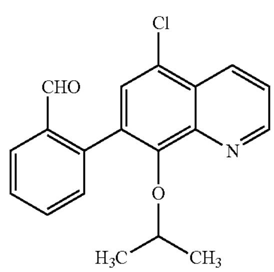 [SMILES: CC(C)Oc1c(-c2ccccc2C=O)cc(Cl)c2cccnc12] | | Y | | >10 | | N/A |
| 868 | 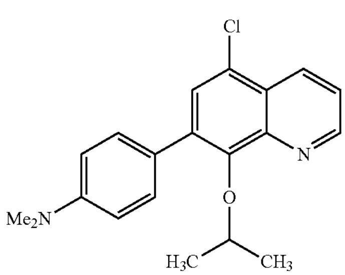 [SMILES: CC(C)Oc1c(-c2ccc(N(C)C)cc2)cc(Cl)c2cccnc12] | | C | | >10 | | N/A |

| ID | Structure | CAS | Sol (Y, C, N) | clogp | Peroxide IC50 | Viable 10 uM | BAS Score |
|---|---|---|---|---|---|---|---|
| 1022 | 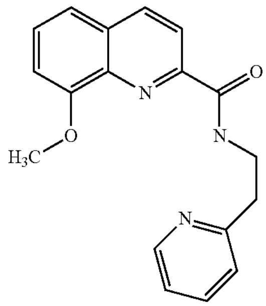 [SMILES: COc1cccc2ccc(C(=O)NCCc3ccccn3)nc12] | | | | >10 | | N/A |

Additional results with respect to various assays utilizing the methodology described are tabulated below on representative compounds identified as their PBT numbers:

TABLE 7

Aβ Neuroprotection
[Methodology as per Assay 2(c)]

| PBT | % inhibition Abeta toxicity |
|---|---|
| 1 | 16 |
| 41 | 12 |
| 42 | 14 |
| 45 | 28 |
| 47 | 13 |
| 53 | −75 |
| 54 | 100 |
| 56 | 17 |
| 59 | 22 |
| 89 | −31 |
| 806 | 36 |
| 810 | 11 |
| 853 | 31 |
| 854 | 22 |
| 864 | 13 |
| 947 | 3 |
| 948 | 9 |
| 950 | 5 |
| 952 | 13 |
| 953 | 25 |
| 968 | 6 |
| 969 | 2 |
| 986 | 7 |
| 987 | 5 |
| 990 | 18 |
| 1002 | 17 |
| 1003 | 17 |
| 1005 | 1 |
| 1006 | 7 |
| 1007 | 9 |
| 1008 | 9 |
| 1009 | 16 |
| 1010 | 12 |
| 1011 | 21 |
| 1020 | 4 |
| 1021 | 1 |
| 1031 | 8 |
| 1032 | −2 |
| 1033 | 38 |
| 1037 | 4 |
| 1038 | 19 |
| 1039 | 9 |
| 1044 | 3 |
| 1045 | 10 |
| 1049 | 6 |

TABLE 7-continued

Aβ Neuroprotection
[Methodology as per Assay 2(c)]

| PBT | % inhibition Abeta toxicity |
|---|---|
| 1050 | 6 |
| 1051 | 23 |
| 1052 | 19 |
| 1053 | −2 |
| 1055 | 37 |
| 1056 | 39 |
| 1057 | 4 |
| 1058 | 30 |

TABLE 8

Test Compound Cytoxicity
[Methodology as per Assay 2(d)]

| PBT | 0.1 um | 1 uM | 10 uM |
|---|---|---|---|
| 1 | 78 | 90 | 77 |
| 41 | 95 | 100 | 100 |
| 42 | 90 | 87 | 79 |
| 45 | 100 | 92 | 67 |
| 47 | nd | 88 | 86 |
| 53 | 96 | 95 | 100 |
| 54 | 89 | 97 | 61 |
| 56 | 108 | 74 | 31 |
| 59 | 89 | 97 | 55 |
| 89 | 87 | 92 | 101 |
| 806 | 99 | 78 | 38 |
| 810 | 100 | 85 | 57 |
| 853 | 93 | 79 | 39 |
| 854 | 94 | 81 | 36 |
| 864 | 100 | 88 | 37 |
| 947 | 100 | 94 | 51 |
| 948 | 100 | 79 | 85 |
| 950 | 95 | 88 | 89 |
| 952 | 98 | 91 | 53 |
| 953 | 101 | 85 | 53 |
| 968 | 103 | 87 | 82 |
| 969 | 91 | 92 | 90 |
| 986 | 96 | 85 | 60 |
| 987 | 92 | 90 | 87 |
| 990 | 95 | 88 | 57 |
| 1002 | nd | 82 | 34 |
| 1003 | nd | 97 | 38 |
| 1005 | nd | 100 | 95 |
| 1006 | nd | 92 | 52 |
| 1007 | nd | 90 | 43 |
| 1008 | nd | 86 | 28 |
| 1009 | nd | 94 | 32 |

TABLE 8-continued

Test Compound Cytoxicity
[Methodology as per Assay 2(d)]

| PBT | 0.1 um | 1 uM | 10 uM |
|---|---|---|---|
| 1010 | nd | 88 | 27 |
| 1011 | nd | 89 | 31 |
| 1020 | nd | 85 | 83 |
| 1021 | nd | 93 | 81 |
| 1031 | nd | 85 | 81 |
| 1032 | nd | 83 | 42 |
| 1033 | nd | 80 | 70 |
| 1037 | nd | 88 | 87 |
| 1038 | nd | 93 | 83 |
| 1039 | nd | 94 | 87 |
| 1044 | nd | 92 | 89 |
| 1045 | nd | 90 | 86 |
| 1049 | nd | 93 | 89 |
| 1050 | nd | 93 | 88 |
| 1051 | nd | 87 | 56 |
| 1052 | nd | 63 | 32 |
| 1053 | nd | 100 | 105 |
| 1055 | nd | 112 | 57 |
| 1056 | | 96.44 | 68.25 |
| 1057 | | 101.84 | 95.02 |
| 1058 | | 82.47 | 54.60 |

TABLE 9

Levels of Soluble Aβ and Insoluble Aβ in Transgenic Mouse Brains.
[Methodology as per Assay 11.]

| Test Compound | Soluble fraction. % change compared with control. | Insoluble fraction. % change compared with control. |
|---|---|---|
| PBT 1 | +50 | −49 |
| PBT 1033 | −37 | −29 |
| PBT 1038 | negligible | −37% |
| PBT 1051 | negligible | −21 |
| PBT 1052 | negligible | −22 |

TABLE 10

Blood Brain Barrier Penetration
[Methodology as per Assay 14.]

| Test Compound | Uptake Ratio |
|---|---|
| PBT-1 | Between 10 and 50% |
| PBT-1033 | >50% |
| PBT-1038 | >50% |
| PBT-1050 | >50% |
| PBT-1051 | >50% |
| PBT-1052 | Between 10 and 50% |

TABLE 11

Physiochemical Properties
[Methodology as per Assay 13]

| Compound | PSA ($Å^2$) | Solubility$_{pH 6.5}$ (µg/mL) | Solubility (µg/mL) 0.01M HCl | cLog P | E Log $D_{7.4}$ |
|---|---|---|---|---|---|
| PBT1 | 33.1 | <3.1 | 3.1-6.2 | 4.32 | 1.85 |
| PBT1033 | 35.8 | 3.1-6.2 | <3.1 | 3.51 | 1.32 |
| PBT1038 | 90.9 | 12.5-25 | 3.1-6.2 | 2.69 | 2.92 |
| PBT1050 | 80.0 | 12.5-25 | 25-50 | 2.56 | 2.98 |
| PBT1051 | 44.6 | <3.1 | <3.1 | 3.58 | 2.64 |
| PBT1052 | 46.0 | <3.1 | 6.3-12.5 | 4.22 | 2.85 |

TABLE 12

Transgenic Mouse Brain Immunohistochemistry
[Methodology as per Assay 15]

| | Mean plaque score | % difference from control (sham treated animal) | P value |
|---|---|---|---|
| Sham | 3.5 | | |
| 1033 | 2.06 | −41 | 0.018 |
| 1038 | 3.0 | −17 | NSD |
| 1051 | 2.13 | −39 | 0.0037 |
| 1052 | 3.2 | −8 | NSD |

TABLE 13(a)

Pharmacokinetic Parameters following Intravenous and Oral Administration of PBT 1033 to rats.

| Parameter | 030701-A IV | 030701-B IV | Mean ± SD | 030701-C PO | 030710-D PO | Mean ± SD |
|---|---|---|---|---|---|---|
| Measured Dose (mg/Kg) | 1.84 | 1.62 | 1.73 ± 0.16 | 34.11 | 31.21 | 32.66 ± 2.05 |
| $C_{max}$ (µM) | 0.70 | 2.48 | 1.59 ± 1.26 | 2.02 | 1.36 | 1.69 ± 0.47 |
| $T_{max}$ (min) | 20 | 5 | 12.50 ± 10.61 | 45 | 60 | 52.50 ± 10.61 |
| $t_{1/2}$ (min) | 52.25 | 53.29 | 52.77 ± 0.73 | — | — | — |
| $Cl_{total}{}^a$ (mL/min/Kg) | 90.98 | 145.69 | 118.34 ± 38.69 | — | — | — |
| $V_{dB}$ (L/Kg) | 6.86 | 11.20 | 9.03 ± 3.07 | — | — | — |
| BA (%)$^b$ | — | — | — | 25.45 | 25.04 | 25.25 ± 0.29 |

[Methodology as per Assay 16]

$^a$Total plasma clearance $^b$Oral BA calculated using the truncated $AUC_{0-1560}$.

TABLE 13(b)

Pharmacokinetic Parameters following Intravenous and Oral
Administration of PBT 1038 to rats.
[Methodology as per Assay 16]

| Parameter | 030410-B IV | 030410-E IV | Mean ± SD | 030410-C PO | 030415-E PO | Mean ± SD |
|---|---|---|---|---|---|---|
| Measured Dose (mg/Kg) | 0.34 | 0.35 | 0.34 ± 0.00 | 38.74 | 34.47 | 36.60 ± 3.02 |
| $C_{max}$ (µM) | 8.06 | 2.84 | 5.45 ± 3.70 | 57.77 | 68.48 | 63.12 ± 7.57 |
| $T_{max}$ (min) | — | — | — | 45 | 45 | 45.00 ± 0.00 |

TABLE 13(c)

Pharmacokinetic Parameters following Intravenous and Oral
Administration of PBT 1050 to rats.
[Methodology as per Assay 16]

| Parameter | 030415-A IV | 030415-B IV | Mean ± SD | 030415-C PO | 030415-D PO | Mean ± SD |
|---|---|---|---|---|---|---|
| Measured Dose (mg/Kg) | 2.37 | 2.05 | 2.21 ± 0.23 | 35.14 | 26.25 | 30.69 ± 6.29 |
| $C_{max}$ (µM) | 33.93 | 16.88 | 25.41 ± 12.06 | 61.00 | 7.03 | 34.02 ± 38.17 |
| $T_{max}$ (min) | — | — | — | 45 | 120 | 82.5 ± 53.03 |

TABLE 13(d)

Pharmacokinetic Parameters following Intravenous and Oral
Administration of PBT 1051 to rats.
[Methodology as per Assay 16]

| Parameter | 030506-A IV | 030506-B IV | Mean ± SD | 030506-C PO | 030506-D PO | Mean ± SD |
|---|---|---|---|---|---|---|
| Measured Dose (mg/Kg) | 3.16 | 2.77 | 2.96 ± 0.28 | 34.24 | 26.45 | 30.35 ± 5.51 |
| $C_{max}$ (µM) | 2.96 | 3.03 | 2.99 ± 0.05 | 3.18 | 1.50 | 2.34 ± 1.18 |
| $T_{max}$ (min) | — | — | — | 60 | 30 | 45 ± 21.21 |
| $t_{1/2}$ (min) | 46.07 | 46.52 | 46.30 ± 0.32 | 200.09 | 365.72 | 282.9 ± 117.1 |
| $Cl_{total}$[a] (mL/min/Kg) | 153.24 | 135.58 | 144.4 ± 12.5 | — | — | — |
| $V_{dB}$ (L/Kg) | 10.19 | 9.10 | 9.64 ± 0.77 | — | — | — |
| BA (%)[b] | — | — | — | 37.96 | 17.55 | 27.75 ± 14.43 |

[a] Total plasma clearance
[b] Oral BA calculated using the truncated $AUC_{0-1440}$. This value may be an overestimation of the true bioavailability.

Example 21

Clinical Trial of Compound of Formula I or II for the Treatment of Alzheimer's Disease A Phase II clinical trial of the compound of formula I or II for the treatment of AD was undertaken to study the effects of oral PBT-1 treatment in a randomised, double-blind, placebo-controlled pilot phase 2 clinical trial of moderately severe AD patients. Thirty-six subjects were randomized [18 placebo and 18 PBT-1, with 32 completions], and stratified into more- and less-severely affected groups. The effect of treatment was statistically significant in preventing cognitive deterioration over 36 weeks in the more-severely affected patients (baseline ADAS-cog≥25). The performance of the less-severely affected group (ADAS-cog<25) deteriorated negligibly over this interval, so cognitive changes could not be discriminated in this stratum. Plasma $A\beta_{42}$ declined in the PBT-1 group but increased in the placebo group (p<0.001). Plasma Zn levels rose significantly (≈30%) in the PBT-1 group.

Dosage

Several considerations drove the choice of dose. In previous studies on transgenic mice, doses of 20-30 mg/kg of PBT-1 orally daily for five days per week were markedly effective at inhibiting Aβ accumulation after 2-3 months of treatment. The human equivalent dose of 1500-2250 mg/day is close to the prescribed antibiotic dose of PBT-1 (600 mg po qid). However, this magnitude of dose, administered for months, would raise concerns about SMON toxicity.

The starting dose of 3.3 mg/kg/day, assuming 75 kg average weight, is within the same order of magnitude of the effective dose in the transgenic mouse model, but only about one tenth of the antibiotic dose.

Since there is no data from the transgenic mouse study of the effectiveness of doses less than 20 mg/kg/day, we reasoned that a beneficial effect might require a longer period of treatment than the 9-12 week duration of the mouse study (Cherny et al., 2001). Therefore a trial length of 36 weeks at an average dose which is approximately one-third of what is effective in the transgenic mice is chosen. The final dose of 10 mg/kg/day is half of an effective dose in mice.

The starting dose of 3.3 mg/kg/day was within the same order of magnitude of the effective dose in the transgenic mouse model, but only about one tenth of the anti-infective dose. The study was powered to detect biochemical effects on metal and Aβ levels that would be in the same magnitude as those seen in the transgenic study.

Experimental Procedures

Ethical Issues:

In compliance with Australian laws concerning consent from individuals whose cognitive function may be impaired to the extent of being unable to make informed judgements or decisions, "Consent to Special Procedures" administered by the Victorian Civil and Administrative Tribunal was obtained for each participant not able to consent on their own behalf. In addition, third party consent was obtained from all carriers. All subjects were stabilized on donepezil prior to commencement of the study. The study was approved by the Royal Melbourne Hospital Research Foundation's Clinical Research and Ethics Committee.

Study Population:

The study took place at the AD clinical trials unit, Mental Health Research Institute of Victoria and at the Royal Melbourne Hospital. Criteria for inclusion in the study were: informed consent; a diagnosis of probable AD by NINCDS-ADRDA criteria (McKhann et al., 1984); AD Assessment Scale-cognitive (ADAS-cog) (Rosen et al., 1984) score of 18-45; Mini Mental State Examination (MMSE) (Folstein et al., 1975) score of 10-24; on donepezil 5 mg or 10 mg for at least 6 months; relative or carrier willing and able to support the trial; able to complete trial examinations; primary sensorial functions intact.

Patients were excluded if they had a history or clinical evidence of peripheral or optic neuropathy or had co-existing illnesses or past history that may have affected cognitive function, nerve conduction or illnesses that may have confounded the adverse event profile. The following factors were obtained at baseline to determine if they correlated with outcome measures: age, sex, premorbid IQ [estimated from the National Adult Reading Test (NART)], years of education, and apolipoprotein E (ApoE) allotype.

Study Design:

The study was a double blind, placebo-controlled, parallel group randomized design. Thirty-six patients and their carriers were recruited to participate, with patients randomized at a 1:1 ratio to receive either PBT-1 or placebo. The duration of the study was 36 weeks. PBT-1 oral dosage was 125 mg bid from weeks 0-12, increased to 250 mg bid from weeks 13-24, and finally, 375 mg bid from weeks 25-36.

Study Procedures:

Screening procedures consisted of a complete medical history, physical, neurological and ophthalmic examination, blood and urine tests and psychometric tests (ADAS-cog, MMSE). Nerve conduction tests and visual evoked responses were conducted between the screening and baseline visits to provide a baseline measurement. Blood was collected for ApoE allotyping, baseline plasma levels of metals and Aβ prior to randomization. All patients continued their study entry dose of donepezil and all patients received 100 mg vitamin $B_{12}$ intramuscularly every four weeks.

Blood samples were collected by antecubital venepuncture except on weeks 12, 24 and 36 when they were collected by an indwelling catheter. The procedural change did not affect biochemical readouts except for Zn levels which were found to be consistently ~10% depressed (probably as a result of differences in platelet activation). Zn data from these intervals were therefore omitted from analysis.

Outcome Measures:

The primary clinical efficacy variable was a change from baseline score on the ADAS-cog conducted at baseline and at weeks 4, 12, 24 and 36. This measure was chosen to allow comparability of treatment effects with current therapeutics such as donepezil, where efficacy trials also used ADAS-cog as their primary outcome measure (Rogers et al., 1998). Although numerous neuropsychological tests could be considered as secondary measures, it was necessary to avoid fatiguing the subjects at review. Therefore the only other cognitive test was the Mini-Mental State Exam (MMSE). The CIBIC+ (clinician interview based impression of change incorporating caregiver information), a subjective observational index was also conducted. Plasma Aβ, and plasma zinc and copper were all taken every four weeks.

Double Antibody Capture Enzyme-Linked Immunosorbent Assay (ELISA) for Aβ Detection:

Polystyrene plates were coated with mAb G210 (for Aβ40) or mAb G211 (for Aβ42). Plates were washed and biotinylated mAb WO2 was added. Bound antibody was detected with streptavidin-labelled Europium (Perkin Elmer, Vic Australia). The values obtained from triplicated wells were calculated based on standard curves generated on each plate. Plasma samples supplemented with synthetic Aβ1-40 and Aβ1-42 were also assayed to confirm measurement reliability across the concentration range of interest.

Metal Levels:

Metals were measured by inductively coupled plasma mass spectrometry as previously described (Cherny et al., 2001).

Therapeutic Drug Monitoring:

At weeks 12, 24 and 36, PBT-1 blood levels were assayed by HPLC with appropriate validation studies (Centre for Pharmaceutical Research, University of South Australia).

Safety Measures:

Standard adverse event reporting was conducted and biochemical tests, renal and liver function, complete blood examination, serum vitamin $B_{12}$ and folate levels were documented at each visit. To assess for peripheral and optic neuropathy a neurological examination was conducted at each visit, and visual evoked responses, nerve conduction studies and ophthalmic examination were conducted at screening, week 16 and prior to the final trial visit. An ECG was done at screening and weeks 12, 24 and 36.

Data Preparation and Statistical Analysis:

Data monitoring and management were undertaken by independent contractors (Kendle International and Health Research Solutions, Melbourne). Evidence for efficacy was indicated by a significant difference in change from baseline between treatment arms. Analysis of variance was the principal method of evaluating statistical significance with the treatment arm illness severity at baseline being the primary design factor. Potentially significant covariates were introduced as necessary. Differences between groups on categorical measures were analysed using exact statistical methods in order to maximise power. Based on the assumption of a correlation of 0.60 between measurement occasions, power to detect an effect of one standard deviation difference in change between groups from baseline to week 36 would have been approximately 80% if 15 subjects were recruited per group. Since an attrition rate of 15% has been observed in similar populations, 18 patients were recruited into each arm.

Results

Figure 7:
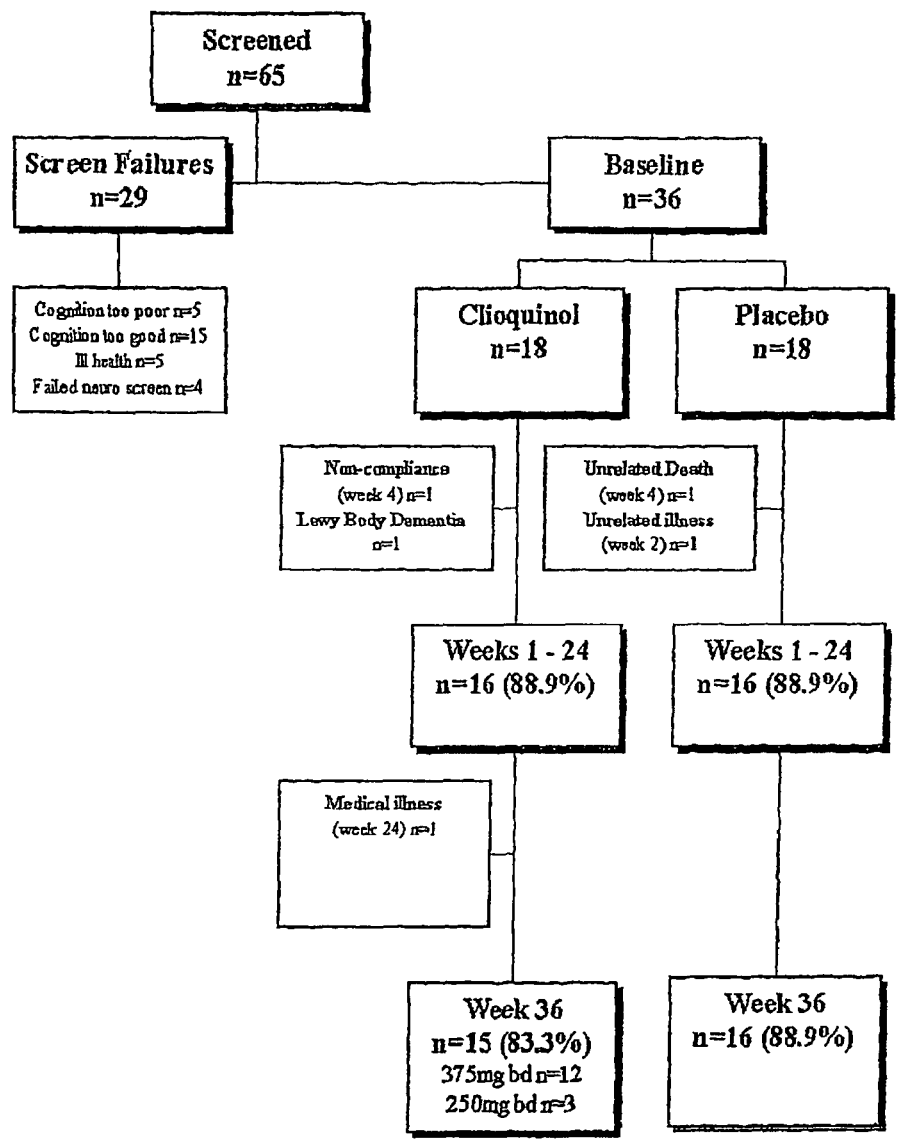
FIG. 7 is a flow chart of subjects studied.

Subject Recruitment and Demographics:

Thirty-six subjects were recruited over a 12 month period commencing April 2000 (FIG. 7). Of these, 32 had sufficient data for per protocol analysis. Two subjects were lost from each arm.

The baseline illness severity factor was created, as planned, by division of the sample into two groups at the median ADAS-cog score at baseline (values<25, ≥25), yielding less-severely and more-severely affected groups (n=8 and 8 in the treatment arm and n=7 and 9 in the placebo arm, respectively).

The groups did not differ across demographic, biological and clinical parameters at baseline (Table 14), other than the treatment arm having a higher mean premorbid IQ than the placebo group as estimated using the NART (111.4 compared to 104.9; t(30)=2.27, p=0.031) and a lower level of thyroid stimulating hormone (TSH) (1.14 compared to 2.00 mU/L; t(30)=4.400, p<0.001). The NART and TSH were subsequently provisionally entered into analyses as co-variates but were found to be not significant in any analysis.

Figure 8:
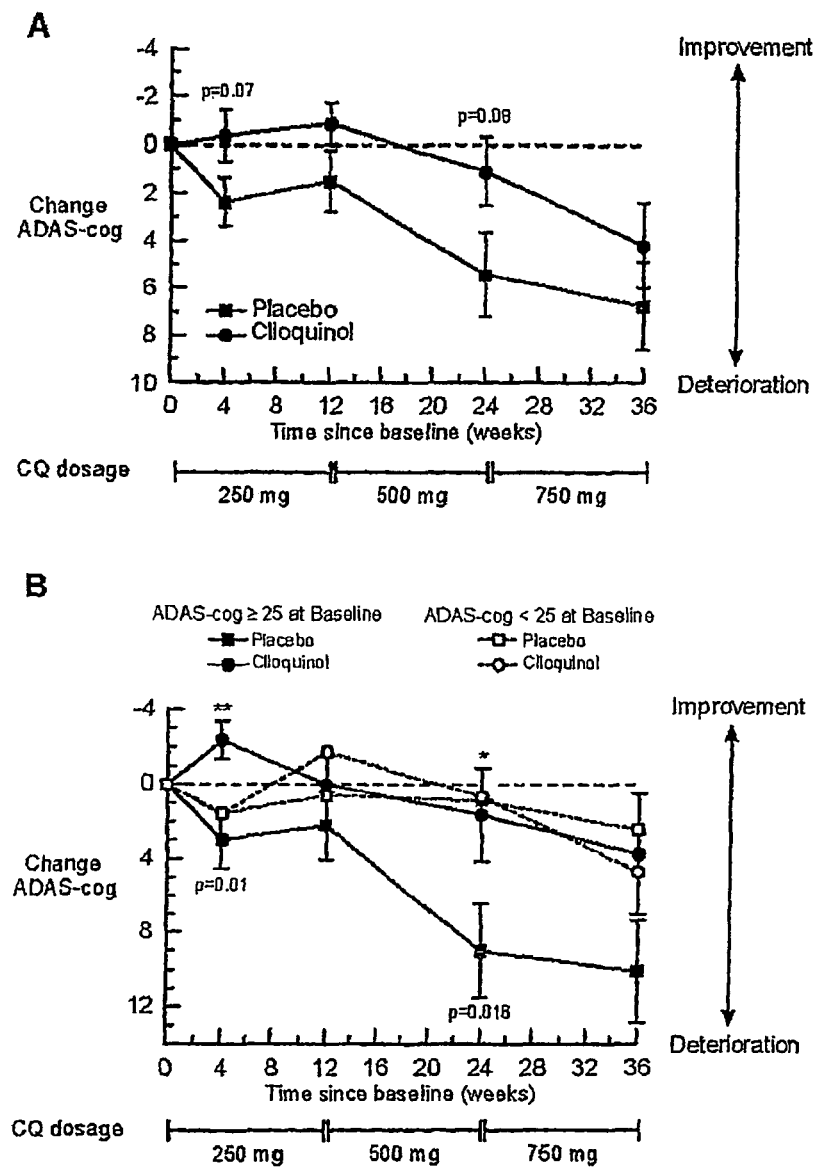
FIG. 8 are graphs showing mean change (±SE) over time from baseline in cognitive abilities (as assessed with ADAS-cog) in (A) two arms of CQ vs placebo and (B) stratification by severity within treatment arms [less-severely affected (ADAS-cog<25), more-severely affected (ADAS-cog≥25) (*p≤0.05; ** p≤0.01)

Clinical Effects:

Changes in the ADAS-cog score at weeks 4, 12, 24 and 36 from baseline were subject to two-way analysis of variance with factors of treatment arm and baseline illness severity. The means of the changes in ADAS-cog score showed greater deterioration in the placebo treated group at each examination interval, compared to the PBT-1-treated group (FIG. 8A). This trend came close to statistical significance at week 4 [F(1,28)=3.55, p=0.070] and week 24 [(F(1,28)=3.31, p=0.080](FIG. 8A). As planned in the protocol, the effect of severity of illness was examined by stratification of the sample into subjects less- or more-severely affected (baseline ADAS-cog values<25, ≥25). Simple effects tests within level of severity showed the trend in the pooled groups to be separable into non-significant results for the less-severe stratum on all weeks and significant differences in the more-severe stratum at weeks 4 [F(1,28)=7.73, p=0.010] and week 24 [F(1,28)=6.63, p=0.016](FIG. 8B). This trend was maintained at week 36 but narrowly escaped statistical significance [F(1,28)=3.62, p=0.068]. In the more-severely affected groups, the difference in mean change from baseline ADAS-cog score of PBT-1 over placebo at weeks 24 and 36 was a difference of 7.37 (95% CI: 1.51-13.24) and 6.36 (95% CI: −0.50-13.23) respectively (FIG. 8B).

Figure 9:
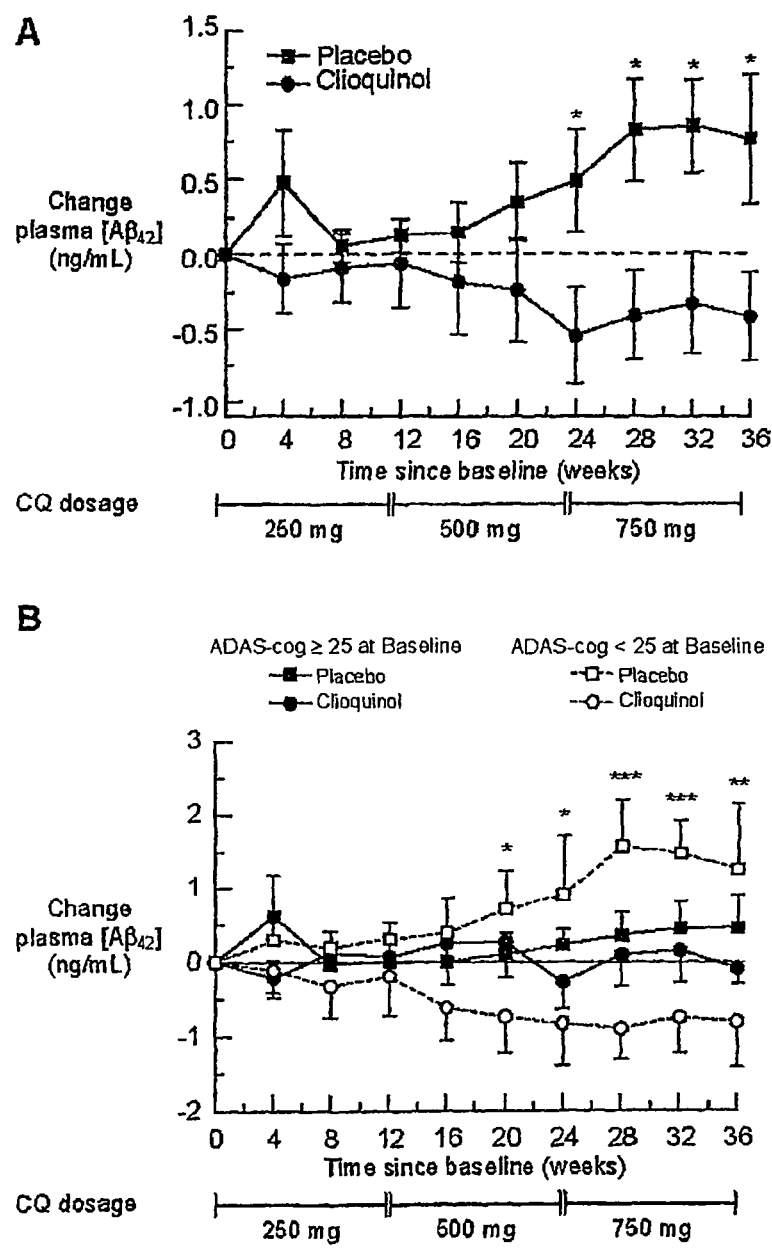
FIG. 9 are graphs showing mean change (±SE) over time from baseline in plasma $Aβ_{42}$ levels in (A) the arms of CQ vs placebo and (B) stratification by severity as in FIG. 8. (***p≤0.001)

Effects on Plasma Aβ, Zn and Cu:

At baseline, there were no significant differences in plasma $A\beta_{42}$ levels between treatment arms or severity strata. The variance in individual levels at baseline in plasma $A\beta_{40/42}$ was large and led to reduced power of the study to detect any significant differences in mean changes between groups. However, reference of individual Aβ levels to baseline reference levels markedly decreased variance, and revealed significant treatment effects. Plasma $A\beta_{42}$ showed a significant decline from baseline in the PBT-1-treated group from week 20 onwards; over the same time, plasma $A\beta_{42}$ in the placebo group increased (FIG. 9A). Stratification by illness severity as above demonstrated that changes were evident only in the less-severely affected (FIG. 9B).

Figure 10:
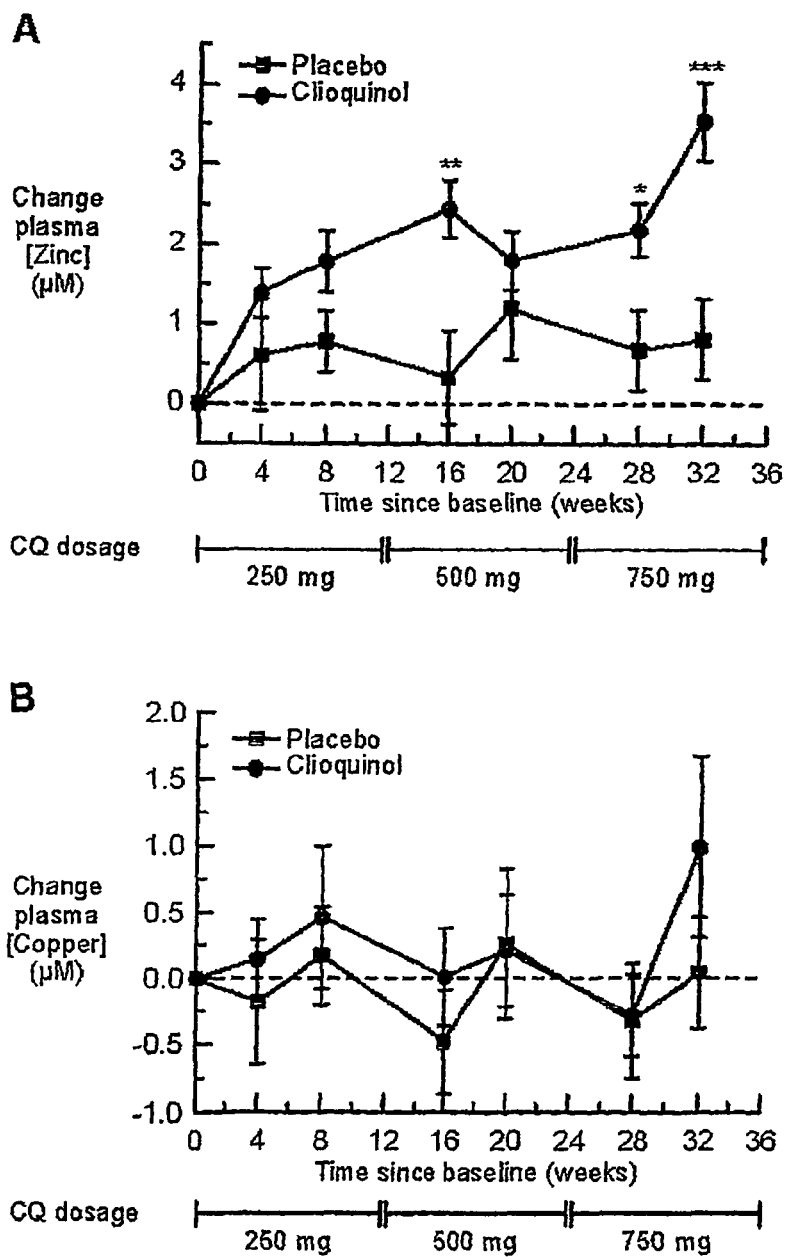
FIG. 10 are graphs showing mean change (±SE) over time from baseline in (A) plasma Zn (B) plasma Cu in the two arms of CQ vs placebo.
Figure 11:
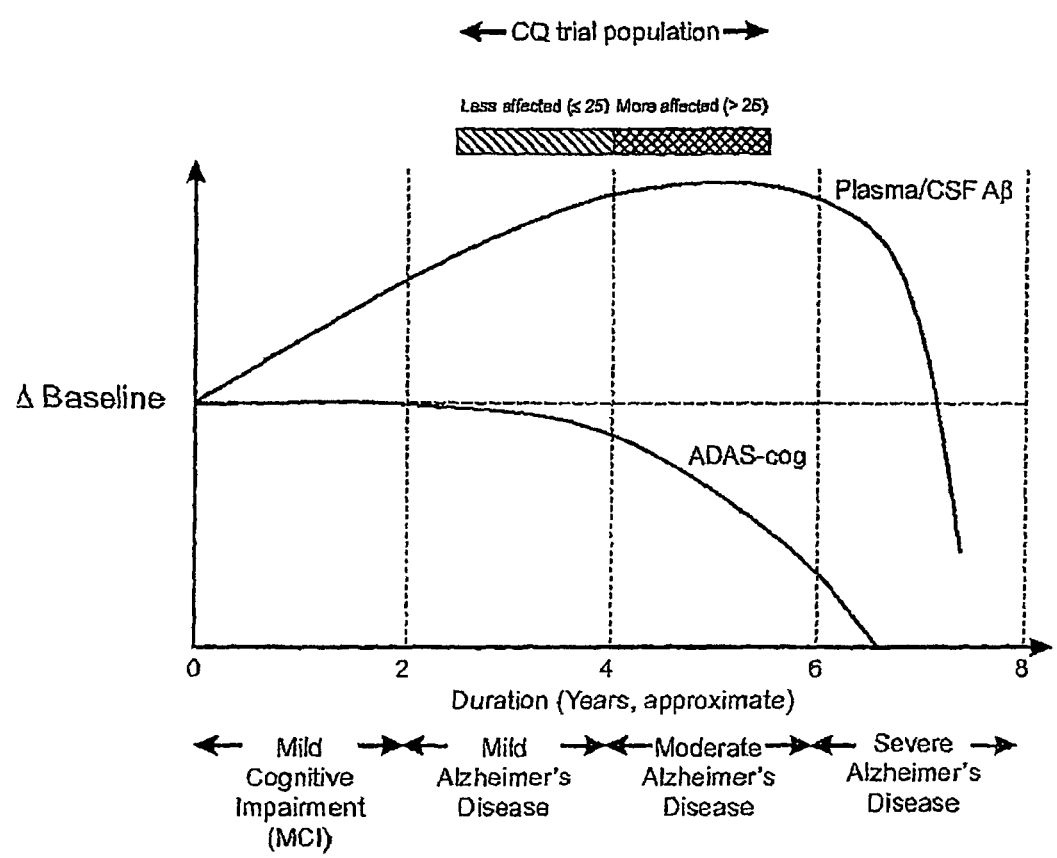
FIG. 11 is a graph showing relative changes in behavioral (ADAS-cog) and biochemical (plasma/CSF Aβ) levels over the course of AD.

Administration of PBT-1 was associated with a significant elevation (≈30%) of total plasma Zn (FIG. 10A) but with no effect on plasma Cu (FIG. 10B). Mean baseline levels of Zn (9.4 µM) in the pooled AD groups were below age-related normative values (Wood and Zheng, 1997). The increase in plasma Zn induced by PBT-1 treatment therefore represented a normalization of levels. In contrast, mean baseline levels of Cu (13.1 µM) were within the age-related normative range (Rahil-Khazen et al., 2000). Correlation of plasma $A\beta_{42/40}$ levels with Zn/Cu levels assayed on the same or subsequent occasions showed no significant associations.

An important result of treatment of AD subjects with PBT-1 is the paradoxical elevation in plasma Zn (FIG. 10A), which is consistent with a restoration in the ZnT3-mediated communication of synaptic zinc with the blood. This also indicates that, in contrast to a typical metal chelator such as desferrioxamine, the mechanism of action of PBT-1 at this dose is not that of a gross tissue chelator. The relatively weak affinity of PBT-1 for the metals appears to be insufficient to cause marked systemic metal depletion in the presence of a re-established equilibrium of metal homeostasis.

Blood Levels of PBT-1:

Steady state pre-dose levels of PBT-1 at total daily dosages of 250, 500 and 750 mg were 4.03±2.10, 6.74±3.70, 7.60±2.15 µg/ml, respectively, and did not show significant correlations with ADAS-cog, metal or Aβ levels assayed on the same or subsequent occasions.

TABLE 14

Baseline demographics and key clinical variables

| Variable | Total Sample (n = 32) | Group Clioquinol (n = 16) | Placebo (n = 16) | P Value |
|---|---|---|---|---|
| Age mean | 72.50 | 73.19 | 71.81 | P = 0.65[†] |
| (SD; min-max) | (8.37; 56-87) | (8.61; 58-87) | (8.35; 56-87) | |
| Sex | 17 | 8 | 9 | P = 1.00[‡] |
| (n; % male) | (53.1%) | (47.1%) | (52.9%) | |
| ApoE status | | | | |
| ApoE4 heterozygote n (%) | 15 | 7 | 8 | P = 1.00[‡] |
| | (46.9%) | (43.8%) | (50.0%) | |
| ApoE4 homozygote n (%) | 3 | 2 | 1 | |
| | (9.4%) | (12.5%) | (6.3%) | |
| Estimated premorbid IQ | 108.1 | 111.4 | 104.9 | P = 0.03[†] |
| NART | (8.86; 91-124) | (8.04; 94-121) | (8.26; 91-124) | |
| mean, (SD; min-max) | | | | |
| ADAS-Cog | 26.31 | 25.56 | 27.06 | P = 0.57[†] |
| | (7.27; 15-46) | (7.67; 15-46) | (7.01; 19-41) | |
| Age of first diagnosis | 70.09 | 70.88 | 69.31 | P = 0.59[†] |
| mean, (SD; min-max) | (7.98; 54-83) | (8.50; 57-83) | (7.61; 54-83) | |
| Duration of illness (years) | 2.41 | 2.31 | 2.56 | P = 0.66[†] |
| mean (SD; min-max) | (1.19; 1-5) | (1.08; 1-4) | (1.32; 1-5) | |

[†]Independent sample t-test (all tests 30 df)
[‡]Exact, two-tailed test.

Example 22

PBT1033 Effects in Transgenic Huntington's Mice (R6/2)

This example describes an in vivo study of PBT1033 in transgenic Huntington's mice (R6/2) using the procedure of Nyuyen, Harby and Massa, 2005. During this study, 44 samples were collected for behavioral tests, including Rotarod performance, clasping tests, body weight and lifespan observations, and 24 samples were utilized for pathology assessments, including brain sectioning and staining for measuring lateral ventricle size, brain weight, whole brain western blotting for mutant Htt aggregate accumulation, and immunocytochemistry for Htt aggregates.

Methods

1. Sample Groups

GROUP A: 10+6 (pathology) R6/2 MICE, treated daily with PBT1033
GROUP B: 10+6 (pathology) R6/2 MICE, treated daily with SSV solution
GROUP C: 12+6 (pathology) wild type (WT) mice, treated daily with PBT1033
GROUP D: 12+6 (pathology) WT mice, treated daily with SSV solution 2. Mice Source The first generation of the colony of transgenic mice R6/2 was ordered. WT males were bred with females that were transplanted with HDexon1/+ ovaries.

From $2^{nd}$ generation, R6/2 positive males were used to breed with WT females. Samples taken were the 3 to 6th generation.

3. PBT1033 in SSV solution was orally administered to mice at 0.6 mg/0.1 ml (100 ml)/20 g. The PBT1033 solution was taken up into a 1-cc syringe attached to a feeding needle and the drug was delivered by oral gavage.

Components of SSV (Standard Suspending Vehicle)

| Composition | Conc. | 500 ml |
| --- | --- | --- |
| NaCl | 0.9% (w/v) | 4.5 g |
| Na-CMC | 0.5% (w/v) | 2.5 g |
| Benzyl alcohol | 0.5% (v/v) | 2.5 ml |
| Tween 80 | 0.4% (v/v) | 2.0 ml |

4. Rotarod was assessed as described by Hockly et al., the contents of which are incorporated by reference, with the modification that the SDI Rota—Rod (San Diego Instruments, San Diego), was set to linearly increase in speed to 40 rpm in 4-min ramp time. Performance is at $4^{th}$, $8^{th}$, $10^{th}$, and $12^{th}$ week, with three days (one for training) per period and three times per day.

5. Body Weight: once per week, start at age 3 weeks.

6. Clasping testing and Behavioral observation: once per week from $5^{th}$ week and daily during the drug treating.

7. Lifespan observation: Group A and B were treated until they died.

8. Brain lateral ventricle size: mouse brain perfusion, sectioning and staining at age 10 weeks. Mice brains were perfused and fixed with 4% PFA and stained with H&E.

9. Whole Brain Western Blotting: whole mouse brain was homogenized in buffer (10 mM Tris HCl (pH 7.4) 11 mM EDTA Na2/1% Triton X100/complete protease inhibitor mixture and then centrifuged at 7000×g for 90 s. The supernatant was boiled in SDS sample buffer for 5 mm at 100° C.

40 micrograms of total protein was run on a 10% SDS gel with a 4% stacking gel. Antibody: anti-GAPDH (1:5000), EM48 anti-Htt antibody (1:1000)

10. Brain weight: brain weighed before freezing at −80° C.

11. Immunohistochemistry was performed in accordance with the procedure in Assay 15, hereinabove.

Summary

Figure 12:
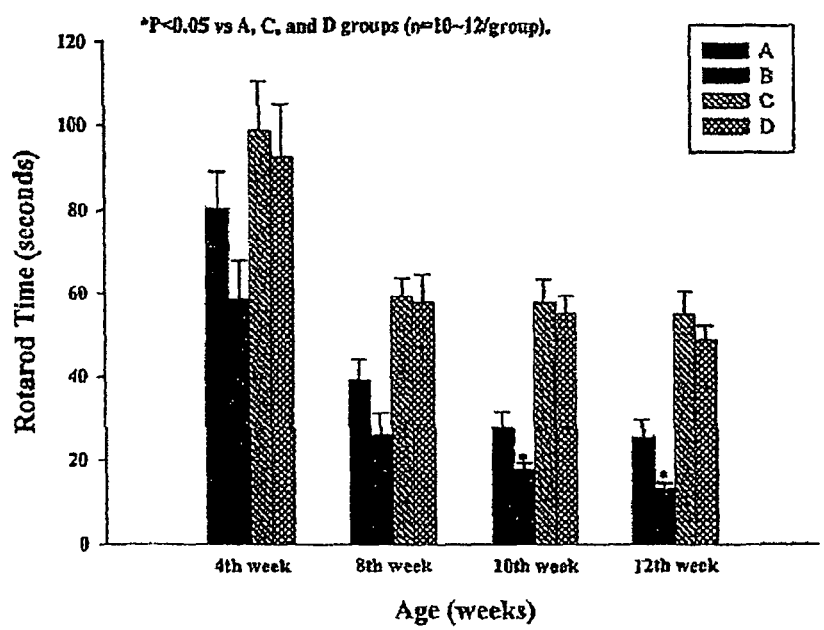
FIGS. 12 and 13 are graphs showing the rotarod time for mice in Groups A and D and Groups A and B, respectively.
Figure 13:
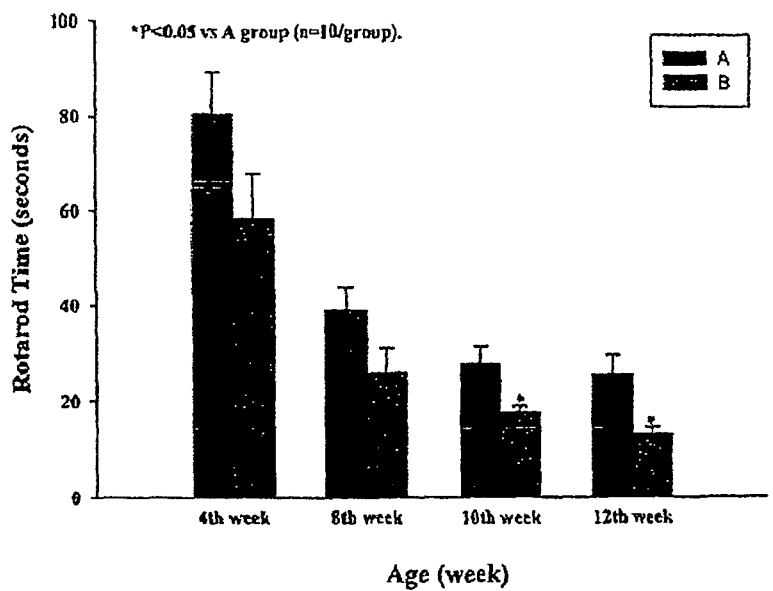

1. There was significant difference for rotarod performance between A and B groups (FIGS. 12 and 13). The rotarod performance time in Group B was less in the 10th week (18±1 seconds, compared with 28±4 seconds in Group A, P<0.05) and 12 week (13±1 seconds in Group B, compared with 26±4 seconds in Group A, P<0.05).

Figure 14:
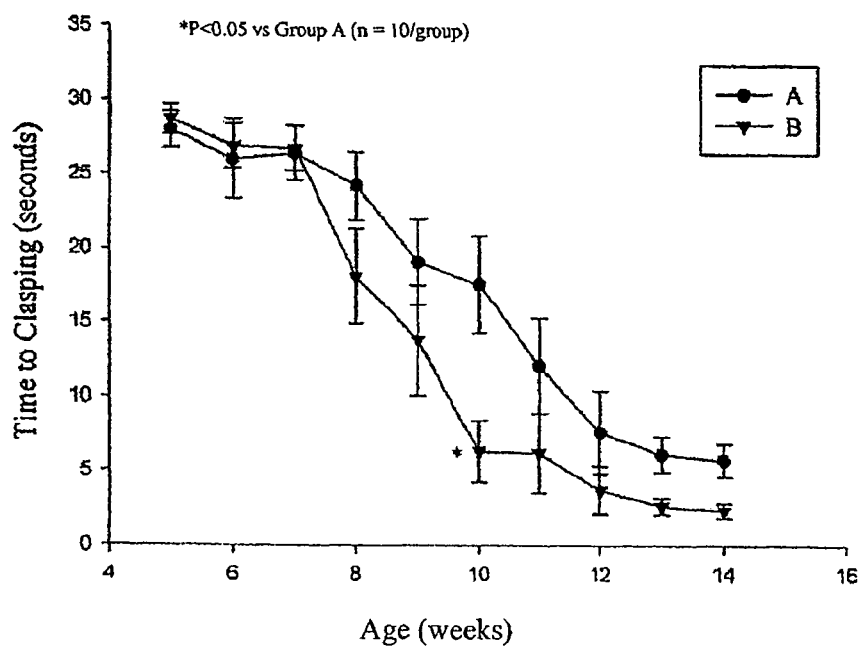
FIG. 14 is a graph showing the time to clasping for mice in Groups A and B.
Figure 15:
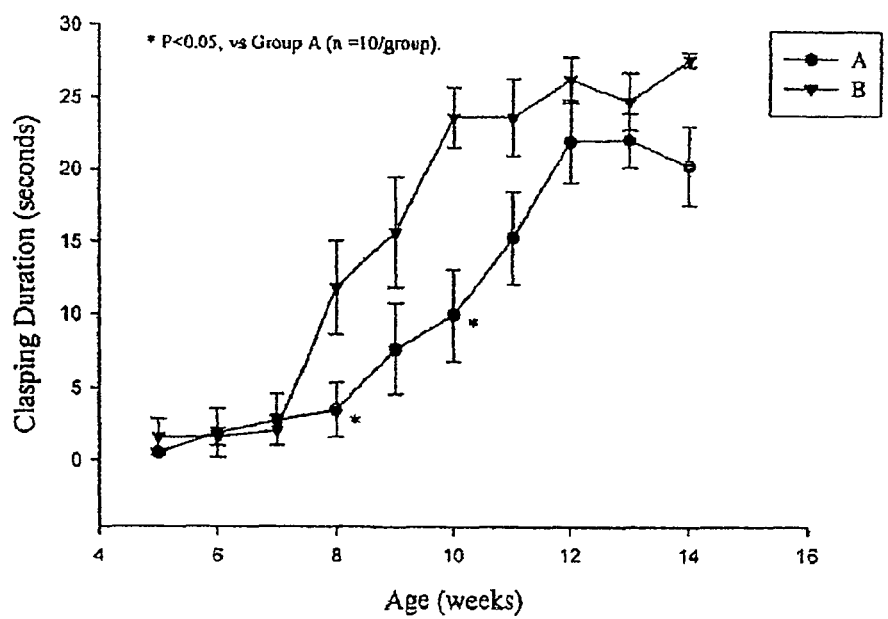
FIG. 15 is a graph showing the clasping duration for mice in Groups A and B.

2. As shown in FIGS. 14 and 15, the clasping latency and duration in Group B were significantly greater than Group A.

Figure 16:
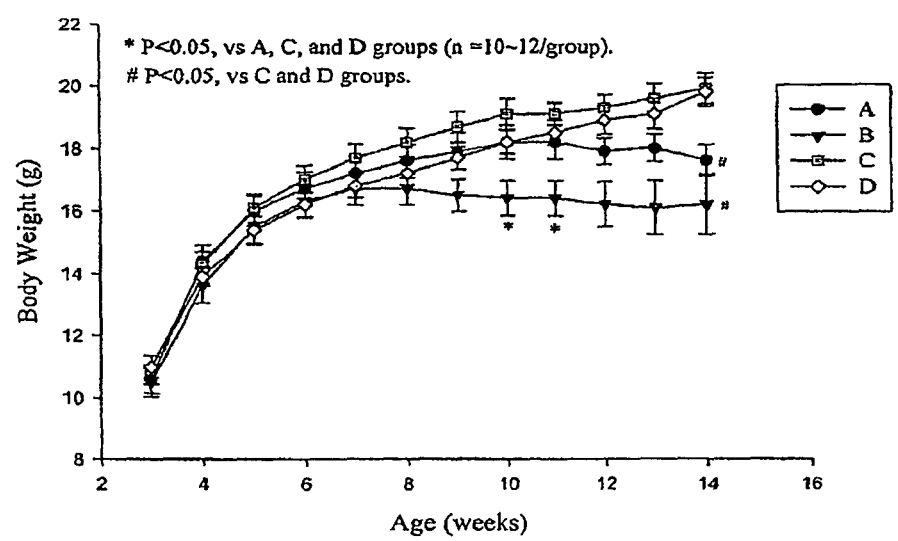
FIG. 16 is a graph showing the body weight of mice in Groups A and B.

3. As shown in FIG. 16, the body weight of mice in Group B was significantly decreased as the week increased (P<0.05, vs A, C, and D groups) of birth.

Figure 17:
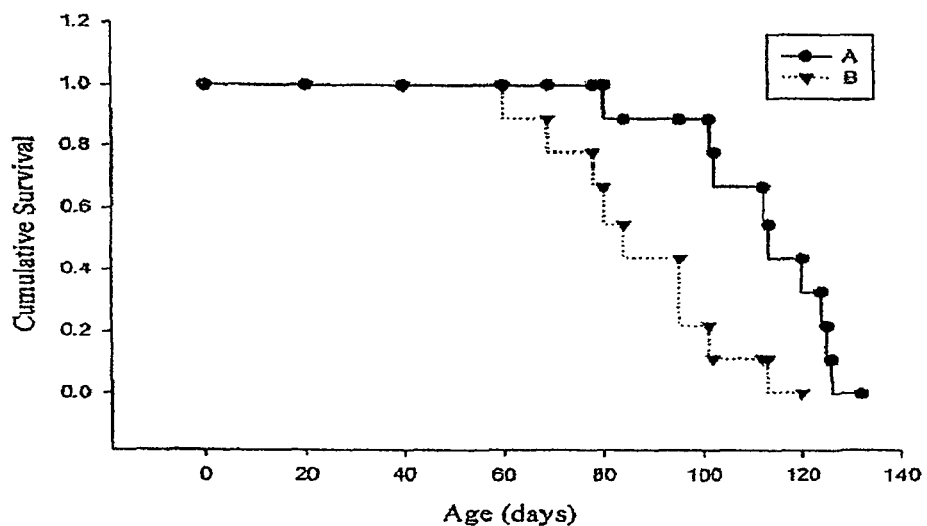
FIG. 17 is a graph showing the cumulative survival of mice in Groups A and B.

4. FIG. 17 shows the life spans of the A and B groups. Animals in Group A survived significantly longer than mice in Group B.

Figure 18:
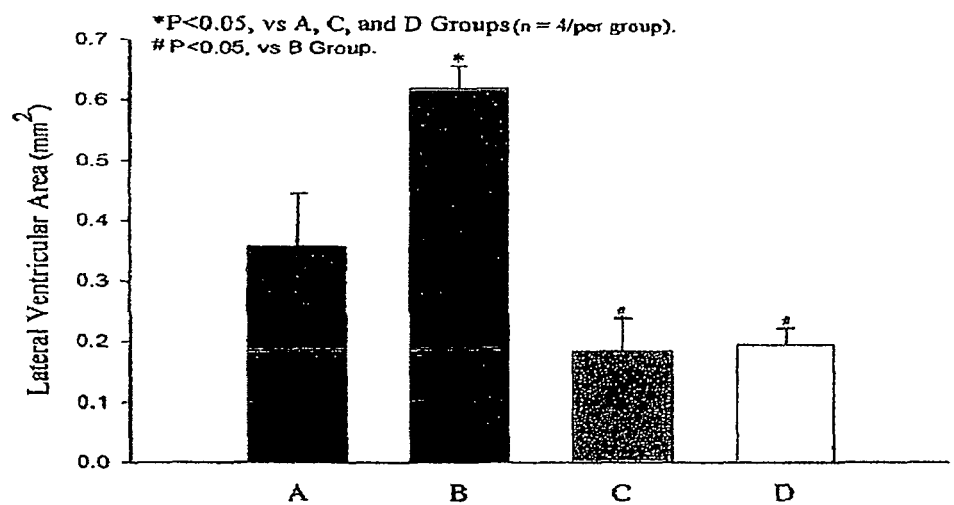
FIG. 18 is a graph showing the lateral ventricular area for mice in Groups A to D.

5. Lateral ventricle area in Group B was significantly larger (0.62±0.037 mm2, P<0.05, compared with A, C, and D groups) (FIG. 18). The lateral ventricle area of Group A was 0.36±0.086 $mm^2$.

Figure 19:
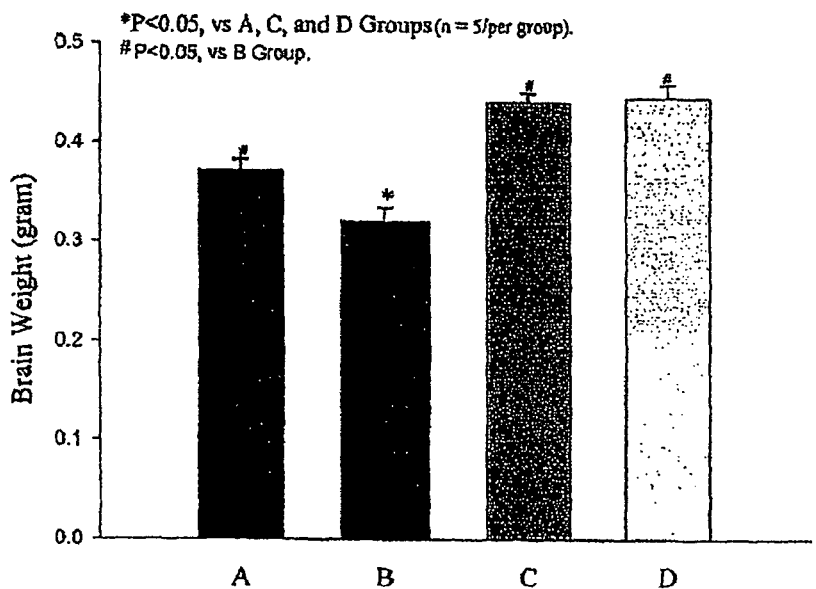
FIG. 19 is a graph showing the brain weight of mice in Groups A to D.

6. Brain Weight data also showed the difference between treated and untreated groups (FIG. 19). The brain weight of group B (0.321±0.0298) was less than group A (0.373±0.0228, P<0.05).

Figure 20:
FIG. 20 is a photo of a Western Blot Analysis of mutant Hungtington protein from mice in Groups A and B, WT and male R6/2 mice.

7. Western analysis shows that mutant Huntingtin (Htt) protein aggregates are detected in untreated HDexon1 mice, but not in treated animals (FIG. 20).

Figure 21:
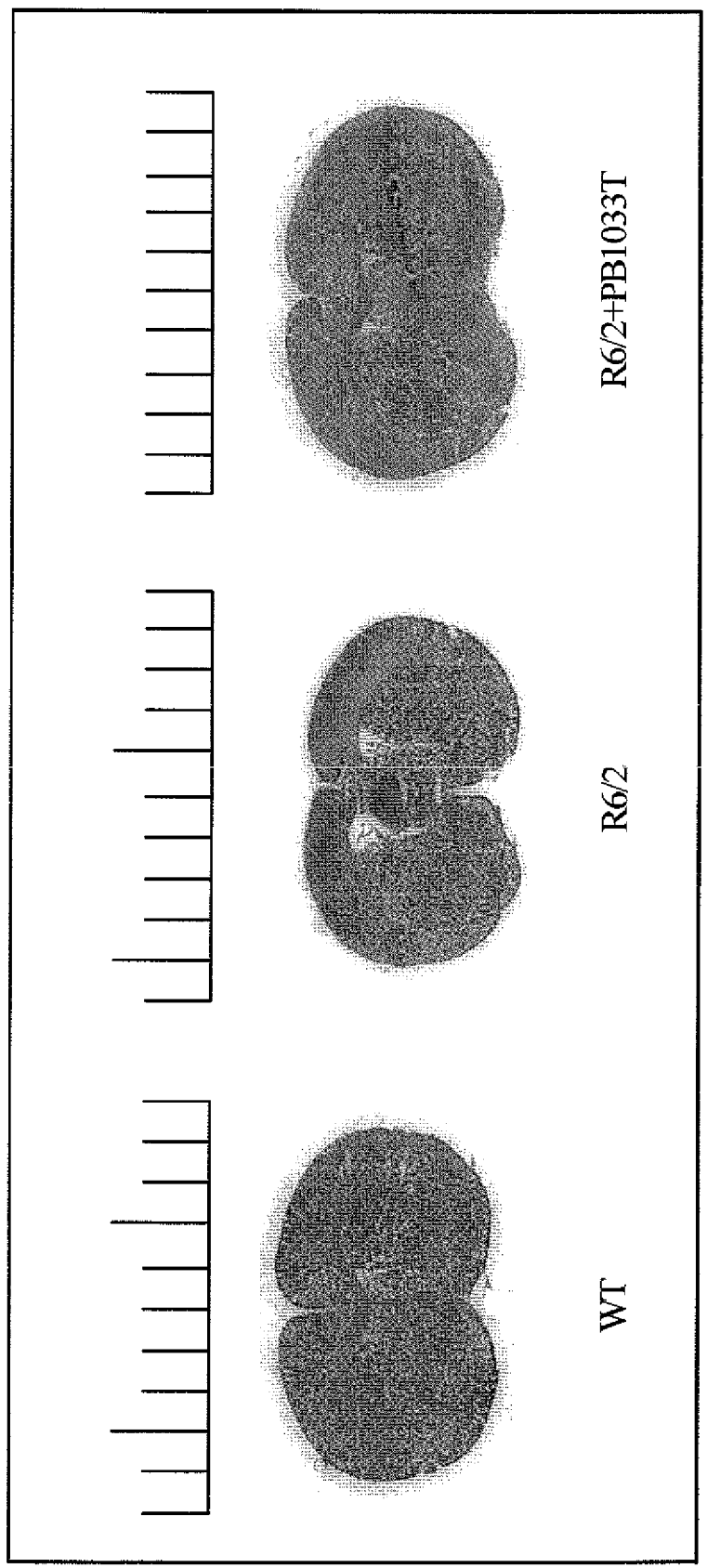
FIG. 21 is a photo showing slices taken from the mice brains for WT, R6/2, and R6/2 mice treated with PBT 1033.
Figure 22:
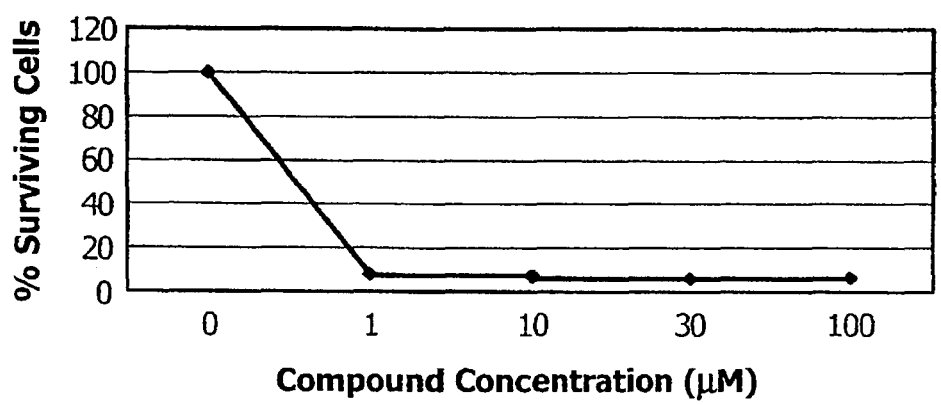
FIG. 22 is a graph showing a cytotoxicity screen of B-1033 and D-105 on C6 cells.
Figure 23:
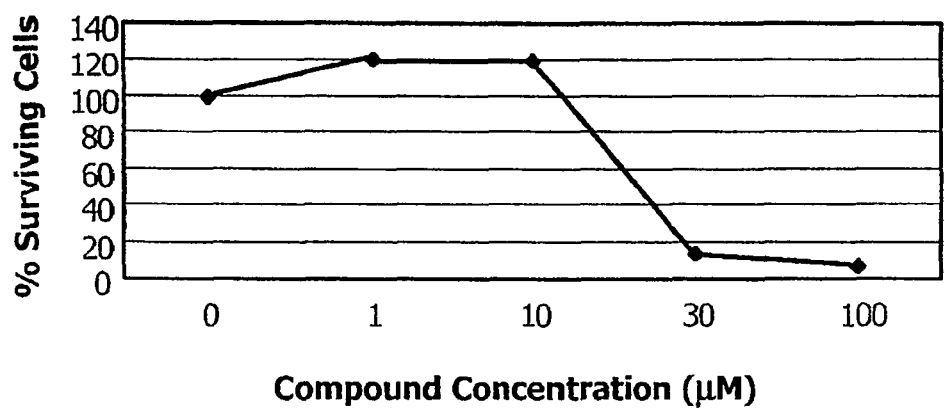
FIG. 23 is a graph showing a cytotoxicity screen of B-1033 and D-105 on U87MG cells.
Figure 24:
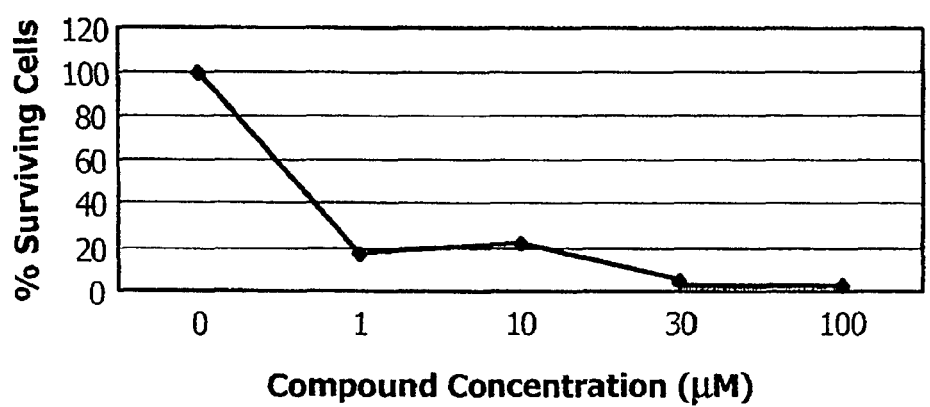
FIG. 24 is a graph showing a cytotoxicity screen of B-1033 and D-105 on SMA 560 cells.

8. FIG. 21 shows the mice brain photos for WT, R6/2 and R6/2 mice treated with PBT1033.

Example 23

Clinical Development of PBT 1033

1033 was administered to healthy volunteers in a 2-part study comprising single dose administration (Stage A) and multidose administration (Stage B). Overall, 1033 was generally well tolerated as a single dose in young male volunteers and up to 7 days of treatment in elderly healthy volunteers.

The objectives of the following trials were to determine the safety, tolerability and pharmacokinetics of single and multiple oral doses of 1033 in healthy volunteers. Double-blind studies were conducted. The protocol included safety measures designed to capture the potential human adverse effects. A total of 65 healthy subjects have been exposed to doses of 1033 (41 single dose, 24 multiple dose).

Disposition of Subjects

Stages A & B

| | | Number of Subjects (N) | | | | | | | | | | |
|---|---|---|---|---|---|---|---|---|---|---|---|---|
| | | | | | | 1033 (mg) | | | | | | |
| Stage | Sex | Placebo | 25 | 50 | 100 | 200 | 300 | 400 | 500 | 600 | 800 | Total |
| A | M | 14 | 5 | 6 | 6 | 6 | 6 | — | 6 | — | 6 | 55 |
| B | M | 4 | — | — | — | 3 | — | 3 | — | 3 | 3 | 16 |
|   | F | 4 | — | — | — | 3 | — | 3 | — | 3 | 3 | 16 |
|   | Total | 8 | — | — | — | 6 | — | 6 | — | 6 | 6 | 32 |

Safety and Tolerability Stage A—Single Dose

In Stage A, fifty five (55) healthy male subjects aged 18-50 years were randomised (3:1) to receive a single oral dose of either placebo or 1033 at one of 7 dose levels (25, 50, 100, 200, 300, 500 or 800 mg).

Analysis from Stage A demonstrated that 1033, when administered as a single oral dose, was well tolerated in healthy male volunteers aged 18 to 50 years. There was no difference in the incidence of adverse events between the 1033 (43.9%) and placebo arms (42.9%).

No clinically significant or relevant changes were observed for clinical laboratory evaluations and physical assessments.

In this study a relationship between the dose range and the number and intensity of the adverse effects could not be established.

Safety and Tolerability Stage B—Multiple Dose

In Stage B, thirty two (32) healthy male and female subjects aged 45-75 years (eight subjects per dose level) were randomised (3:1) to receive a daily oral dose over 7 consecutive days of either placebo or 1033 at one of 4 dose levels (200, 400, 600 or 800 mg). Each dose level comprised of 4 males and 4 females; the randomisation schedule ensuring that 1 subject/sex received placebo and 3 subjects/sex received 1033.

Analysis of Stage B indicates that 1033 was generally well tolerated in healthy elderly subjects.

Example 24

Effect of PBT 1033 Against Glioma Tumours

The following Table provides the property and structure of 1033.

| | In vivo Efficacy and Safety Profile | | | | | |
|---|---|---|---|---|---|---|
| | Cytotoxicity (% viable at 1 and 10 Um)$^a$ | Parent MW/ PSA | ClogP ElogD (E) or ClogD (C) | Toxicity$^b$ at 30 mg/ kg | Mice plasma concentration$^c$ | B:P Ratio$^d$ |
| [Structure: 5,7-dichloro-2-((dimethylamino)methyl)quinolin-8-ol · HCl] | Neuronal cells: 84, 72 M17 cells: 94, 54.3 | 271.1 36.36 | 3.51 (C) 1.07 | None | Up to 500 ng/ml | 12.85 at 5 min, 9.45 at 60 min |

1033 was screened for in vitro efficacy and in vivo efficacy.

Emulsion carrier was used as a control for the in vitro and in vivo test systems. All the agents were tested initially via in vitro testing to determine an efficacy profile with three glioma cell lines and a control cell line. The results are shown in FIGS. 22 to 26.

Experimental Design

In Vitro Efficacy Protocol

The in vitro efficacy of the test articles were analyzed via the MTT cell viability assay.

Figure 25:
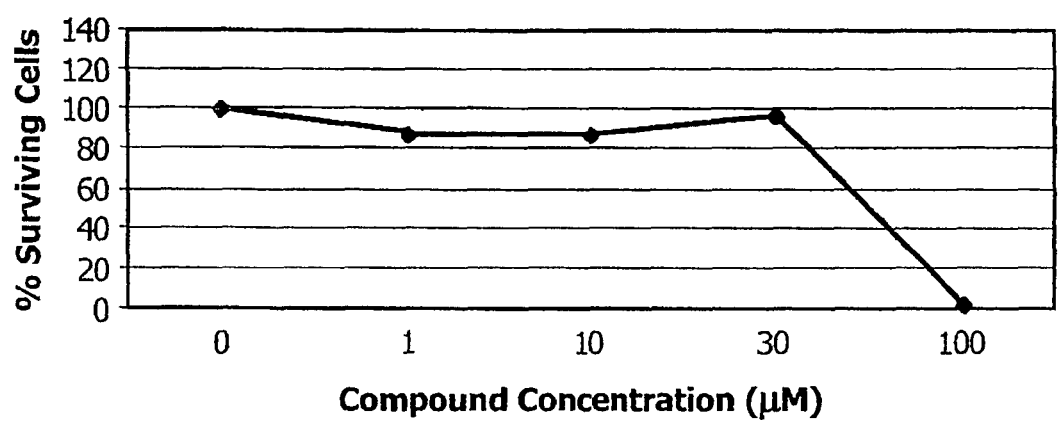
FIG. 25 is a graph showing a cytotoxicity screen of B-1033 and D-105 on 3T3 cells.
Figure 26A:
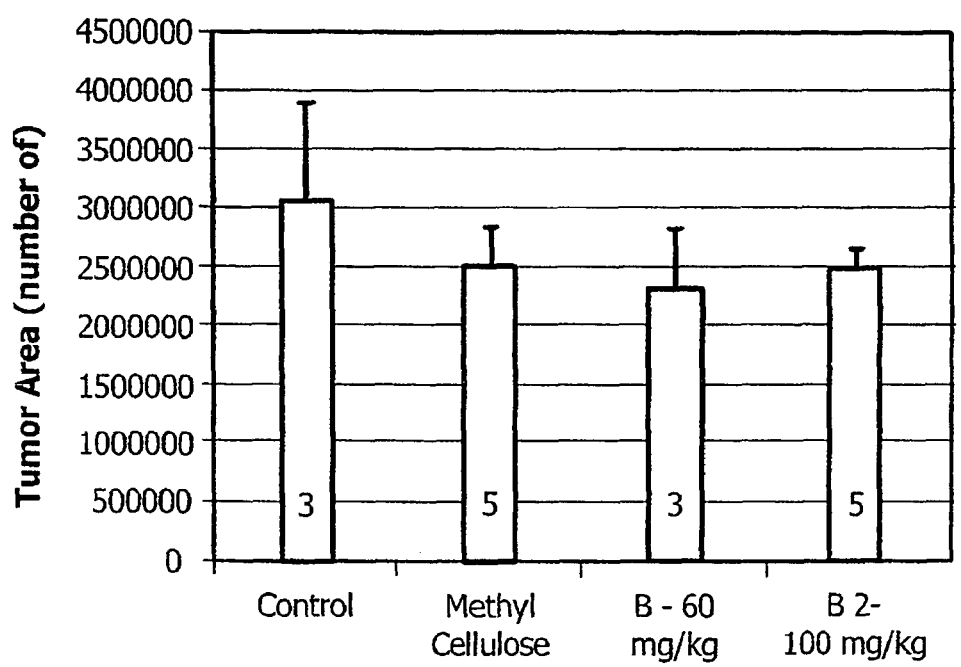
FIG. 26a to d are graphs showing the effects of compound B-1033 in the C6 glioma model (a,c) and the SMA 560 glioma model (b, d).
Figure 26B:
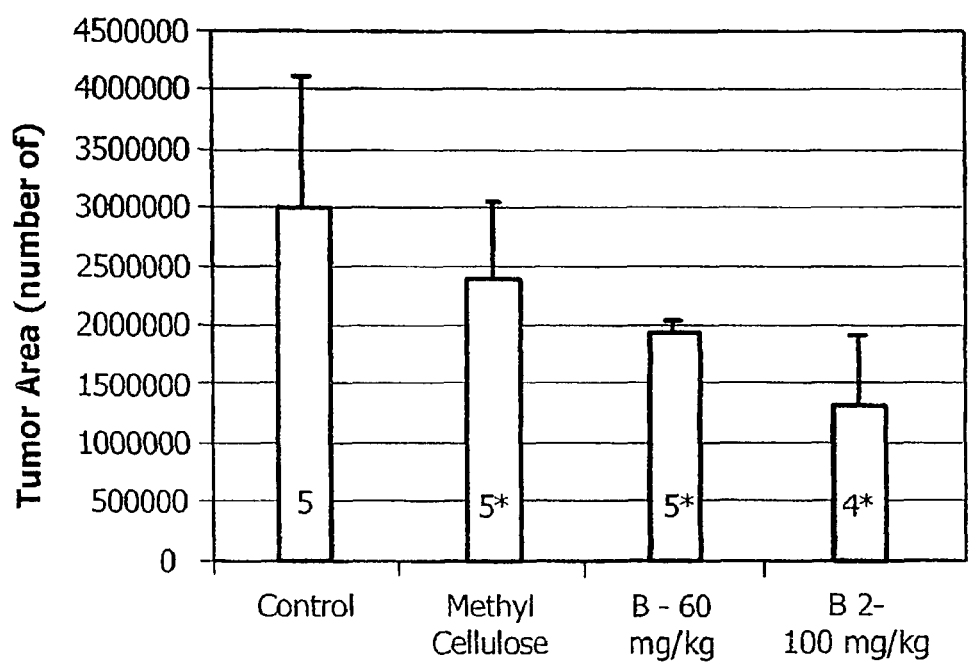
Figure 26C:
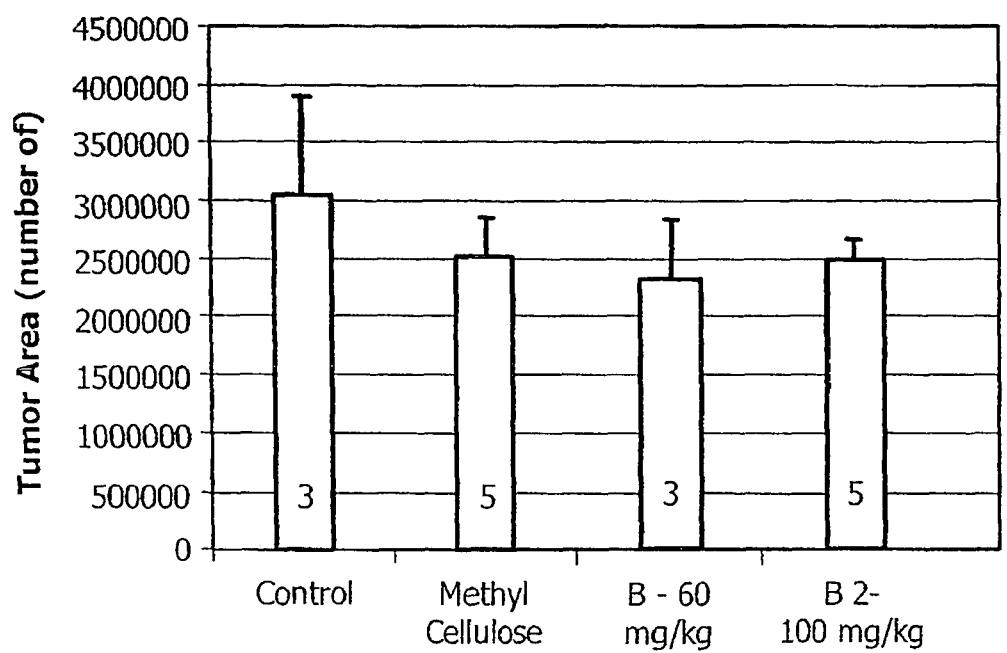
Figure 26D:
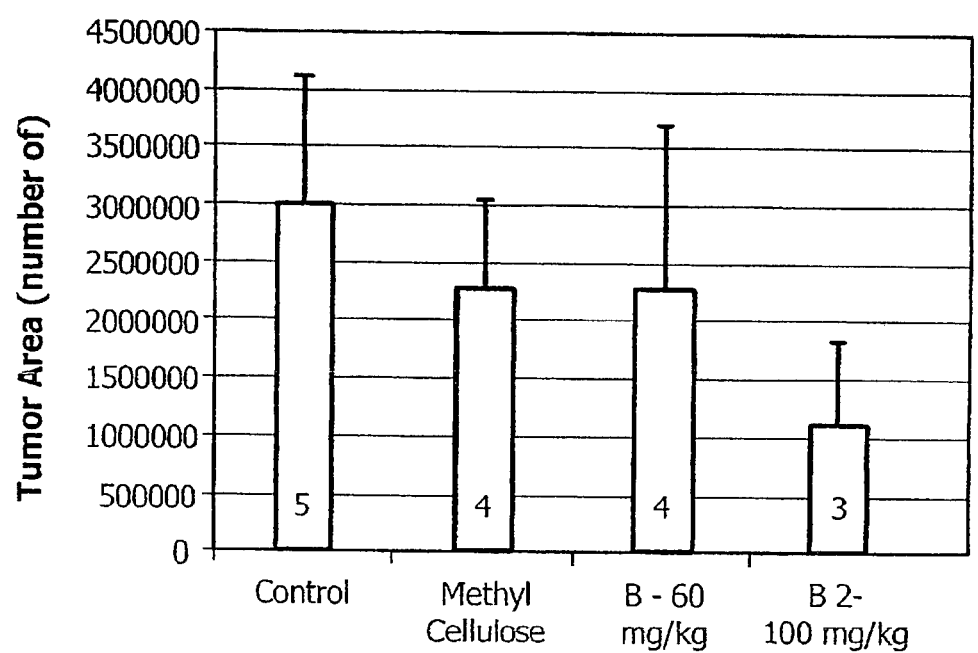

The following cell lines were used to determine cell viability on exposure to the test articles:

C6—rat glioma cell line (FIG. 22), VMDK—mouse glioma cell line (FIG. 24),

U87MG—human glioma cell line (FIG. 23), 3T3—Control cell line (FIG. 25).

Cells were plated in 96 well plates with 100 µl of cell culture medium and be allowed to adhere over 24 hours allowing for approximately 50% confluence. At 24 hours, the cell medium was replaced with fresh cell culture medium containing agents or the carrier emulsions.

The cells will then be incubated and grown for a designated period (72 hours) after which the MTT solution were added to the wells and incubated at 37° C. for 1-2 hours. The absorbance of each well will then be measured with a plate reader at 570 nm. The efficacy profiles were calculated relevant to the cells incubated in the absence of the agents over the course of the experiment.

In Vivo Efficacy Protocol 2 doses were used: at the maximum tolerated dose and one level below the maximum tolerated dose.

3 mouse models are employed:
C6—xenograft mouse model (glioma model)
SMA560—VMDK mouse model (glioma model)
U87MG—nude mouse model C6—CBA Xenograft Model (ATCC Number: CCL-107)
This model is used to screen 1033.

SMA560-VMDK mouse model (ATCC Number: CCL-163)
This model is used to screen 1033 screened previously with the C6 xenograft model.

U87MG Nude mouse model (ATCC Number: CRL-9589)
This model is used to screen 1033.

Initially, CBA mice are used to receive an intracranial inoculation of the C6 glioma cells. Briefly, $1 \times 10^6$ cells are inoculated into the left hemisphere via at day 5 post C6 cell inoculation. The mice receive daily intraperitoneal (ip) administration of test articles in a carrier emulsion or carrier emulsion alone as a control for 8 days until day 12. At day 14, the mice are euthanised via $CO_2$ inhalation and the brain removed for histological processing.

The VMDK mouse strain is then used to screen the identical test articles and carrier emulsions as per the C6 xenograft model in the CBA mice. The VMDK mice received an inoculation of $1 \times 10^5$ SMA560 cells into the left hemisphere via standard methods. At day 5 post SMA560 cell inoculation, the mice receive daily ip administration of agents in a carrier emulsion or carrier emulsion alone as a control for 12 days until day 16. Identical doses of test articles and carrier emulsions as used in the C6 xenograft model are used with the SMA560 model. At day 18, the mice are euthanized via $CO_2$ inhalation and the brain removed for histological processing.

A nude mouse model utilizing the U87MG human glioma cell line is used to screen agents. The nude mouse Nu/nu strain receives an inoculation of $1 \times 10^6$ U87MG cells into the left hemisphere. At day 5 post U87MG cell inoculation, the mice receive daily ip administration of the agent or carrier emulsion alone as a control for 12 days until day 16. At day 18, the mice are euthanized via $CO_2$ inhalation and the brain removed for histological processing.

Haematoxylin and eosin stained sections are used to measure tumor dimensions in order to determine the efficacy of the test agents on tumor growth relative to the control mice.

The results of the effect of compound 1033 is shown in FIGS. 26(a) to (d).

The graphs can be summarized as follows:
Y-axis refers to the tumor area in pixels.

The numbers in the bars refer to the total mice in each group (mice that were found dead very early or brains could not be sampled due to the head being chewed by other mice were not included).

The numbers with the asterix refer to the groups were mice may have been culled 1 or 2 days early due to being ill or found dead. These have been included in the final calculations as their tumors were fairly large and were they were culled close to the final cull point.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Alvarez, A., Alarcón, R., Opaza, C., Campos, E. O., Muñoz, F. J., Calderón, F. H., Dajas, F., Gentry, M. K., Doctor, B. P., De Mello, F., Inestrosa, N. C. (1998) Stable complexes involving acetylcholinesterase and amyloid-β peptide change the biochemical properties of the enzyme and increase the neurotoxicity of alzheimer's fibrils. The Journal of Neuroscience, 18(9):3213-3223

Ariga, T., Kobayashi, K., Hasegawa, A., Kiso, M., Ishida, H., and Miyatake, T. (2001) Characterization of high-affinity binding between gangliosides and amyloid β-protein. Arch. Biochem. Biophys. 388, 225-230

Avdulov, N. A., Chochina, S. V., Igbavboa, U., O'Hare, E. O., Schroeder, F., Cleary, J. P., and Wood, W. G. (1997) Lipid binding to amyloid b-peptide aggregates: preferential binding of cholesterol a. J. Neurochem. 68, 2086-2091

Beyreuther K, Christen Y, Masters C L (eds) Neurodegenerative Disorders: Loss of Function Through Gain of Function. Springer. Berlin. 2001. 189

Brower V. Harnessing the immune system to battle Alzheimer's: Some of the most promising approaches to fight Alzheimer's diseases aim to develop vaccines. EMBO Rep 2002; 3:207-9

Bush A I, Masters C L. Clioquinol's return. Science 2001; 292:2251-2252

Bush A I. Therapeutic targets in the biology of Alzheimer's disease. Current Opinion in Psychiatry 2001; 14:341-348

Carissimi, M. (1972) U.S. Pat. No. 3,682,927

Cherny R A, Atwood C S, Xilinas M E et al. Treatment with a copper-zinc chelator markedly and rapidly inhibits β-amyloid accumulation in Alzheimer's disease transgenic mice. Neuron 2001; 30:665-676

R. C. Corcoran and S. H. Bang, *Tetrahedron Lett.*, 1990, 31, 6757-6758.

Corder, E. H., Saunders, A. M., Strittmatter, W. J., Schmechel, D. E., Gaskell, P. C., Small, G. W., Haines, J. L., and Pericak-Vance, M. A. (1993) Gene dose of apolipoprotein E type 4 allele and the risk of Alzheimer's disease in the late onset familial disease. Science 261, 921-923

Cronin-Golomb A, Sugiura R, Corkin S, Growdon J H. Incomplete achromatopsia in Alzheimer's disease. Neurobiol Aging 1993; 14: 471-477

Curtain, C. C., Ali, F., Volitakis, I., Cherny, R. A., Norton, R. S., Beyreuther, K., Barrow, C. J., Masters, C. L., Bush, A. I., and Barnham, K. J. (2001) Alzheimer's disease amyloid 0 binds copper and zinc to generate an allosterically ordered membrane-penetrating structure containing superoxide dismutase-like subunits. J. Biol. Chem. 276, 20466-20473

Czech, C., Forstl, H., Hentschel, F., Monning, U., Besthorn, C., Geigerkabisch, C., Sattel, H., Masters, C., and Beyruether, K. (1994) Apolipoprotein E-4 gene dose in clinically disgnosed Alzheimer's disease: prevalence, plasma cholesterol levels and cerebrovascular change. Eur. Arch. Psychiatry Clin. Neurosci. 243, 291-292

De Ferrari, G. V., Canales, M. A., Shin, I., Weiner, L. M., Silman, I., Inestrosa, N. C. (2001) A structural motif or acetylcholinesterase that promotes amyloid beta-peptide fibril formation. Biochemistry 40(35):10447-57

Dodart J-C, Bales K R, Gannon K S et al. Immunization reverses memory deficits without reducing brain Aβ burden in Alzheimer's disease model. Nat Neurosci 2002; 5: 452-457

A. Dondoni, G. Fantin, M. Fogagnolo, A. Medici and P. Pedrini, *Synthesis*, 1987, 998 1001.

A. Dondoni, F. L. Merchan, P. Merino, I. Rojo and T. Tejero, *Synthesis*, 1996, 641-646

Durant, G. J., Emmett, J. C., Ganellin, C. R., Roe, A. M. and Slater, R. A. *J. Med. Chem.*, 1976, 19, 923.

Eckert, G. P., Cairns, N. J., Maras, A., Gattaz, W. F., and Muller, W. E. (2000) Cholesterol modulates the membrane-disordering effects of β-amyloid peptides in the hippocampus specific changes in Alzheimer's disease. Dement. Geriatr. Cogn. Disord. 11, 181-186

Fassbender, K., Simons, M., Bergmann, C., Stroick, M., Lutjohann, D., Keller. P., Runz, H., Kuhl, S., Bertsch, T., von Bergmann. K., Hennerici, M., Beyreuther, K., and Hartmann, T. (2001) Simvastatin strongly reduces levels of Alzheimer's disease β-amyloid peptides Aβ 42 and Aβ 40 in vitro and in vivo. Proc. Natl. Acad. Sci. USA. 98, 5856-5861

Fleming, W. C. and Pettit, G. R. *J. Org. Chem.*, 1971, 36, 3490-3493.

Folstein M F, Folstein S E, McHugh P R. Mini-mental state: a practical method for grading the cognitive state of patients for the clinician. J. Psychiatr. Res. 1975; 12:189-198

Frears, E. R., Stephens, D. J., Walters, C. E., Davies, H., and Austen, B. M. (1999) The role of cholesterol in the biosynthesis of b-amyloid. NeuroReport 10, 1699-1705

Friedhoff, L. T., Cullen, E. I., Geoghagen, N. S., and Buxbaum, J. D. (2001) Treatment with controlled-release lovastatin decreases serum concentrations of human β-amyloid (Aβ) peptide. Int. J. Neuropsychopharmacol. 4, 127-130

Gershon, H., Clarke, D. D. and Gershon, M. *Monashafte fur Chemie*, 1999, 130, 653.

Gershon, H. and McNeil, W. M. *J. Heterocycl. Chem.*, 1971, 8, 821.

Gordon, L. M., Curtain, C. C (1988). In: Aloia R. C, Curtain C. C, Gordon L. M. (eds) Advances in Membrane Fluidity 1: Methods for Studying Membrane Fluidity. Alan R. Liss New York, pp 25-89

Hartmann, T. (2001) Cholesterol, Aβ and Alzheimer's disease. Trends Neurosci. 24, S45-S48

Hertel, C., Terzi, E., Hauser, N., Jakob-Rotne, R., Seelig, J., and Kemp, J. A. (1997) Inhibition of the electrostatic interaction between β-amyloid peptide and membranes prevents β-amyloid-induced toxicity. Proc. Natl. Acad. Sci. USA. 94, 9412-9416

Hobara N, Taketa, K. Electrophoretic studies of clioquinol binding to human serum proteins. Biochem Pharmacol 1976; 25: 1601-1606

Hockly, E. Woodman, B., Mahal, A., Lewis, C. M. & Bates, G. (2003), *Brain Res. Bull.* 61, 469-479.

Hope, M. J., Bally, M. B., Webb, G., Cullis, P. R. (1985) Biochim. Biophys. Acta. 812, 55-56

Hsiao, K., Chapman, P., Nilsen, S., Eckman, C., Harigaya, Y., Younkin, S., Yang, F., Cole, G. (1996) Correlative memory deficits, Aβ elevation, and amyloid plaques in transgenic mice Science; 274(5284):99-102.

Huang X, Atwood C S, Hartshorn M A et al. The Aβ peptide of Alzheimer's disease directly produces hydrogen peroxide through metal ion reduction. Biochemistry 1999; 38:7609-7616

Hubbell, W. L. and McConnell, H. M. (1971) J. Amer. Chem. Soc. 93, 314-326

Inestrosa, N. C. Alvarez, A., Perez, C. A., Moreno, R. D., Vicente, M., Linker, C., Casaneuva, O. I., Soto, C., Garrido, J. (1996) Acetylcholinesterase accelerates assembly of amyloid-beta-peptides into Alzheimer's fibrils: possible role of the peripheral site of the enzyme. Neuron 16(4): 881-91

Jensen M, Schröder J, Blomberg M et al. Cerebrospinal fluid Aβ42 is increased early in sporadic Alzheimer's disease and declines with disease progression. Ann Neurol 1999; 45: 504-511

Ji, S. R., Wu, Y., and Sui, S. F. (2002) Cholesterol is an important factor affecting the membrane insertion of β-amyloid peptide (Aβ 1-40), which may potentially inhibit the fibril formation. J. Biol. Chem. 277, 6273-6279

Lee J-Y, Cole T B, Palmiter R D, Suh S W, Koh J-Y. Contribution by synaptic zinc to the gender-disparate plaque formation in human Swedish mutant APP transgenic mice. Proc Natl Acad Sci USA 2002: Early edition.

Mahfoud, R., Garmy, N., Maresca, M., Yahi, N., Puigserver, A, and Fantini, J. (2002) Identification of a common sphingolipid-binding domain in Alzheimer, Prion, and HIV-1 proteins. J. Biol. Chem. 277, 11292-11296

McKhann G, Drachman D, Folstein M F, Katzman R, Price D, Stadlen E. Clinical diagnosis of Alzheimer's disease: Report of the NINCDS-ADRDA work group under the auspices of the Department of Health and Human Services Task Force on Alzheimer's Disease. Neurology 1984; 34:939-944

McLean C A, Cherny R A, Fraser F W et al. Soluble pool of Aβ amyloid as a determinant of severity of neurodegeneration in Alzheimer's disease. Ann Neurol 1999; 46:860-866

Nguyen, T, Hamby, A and Maisa, S. T (2005), "Clinoquinol down-regulates mutant hungtingtin expression in vitro and mitigates pathology in a Huntington's disease mouse model", *PNAS*, Vol 102: No. 33: 11840-11845.

Nunan, J., and Small, D. H. (2000) Regulation of APP cleavage by α-, β- and δ-secretases. FEBS Lett. 483, 6-10

Ostrovskaya, V. M., Krasavin, I. A., Inshakova, V. A., Mamaev, V. P. and Krivopalov, V. P. (1986) SU Patent 1216184 A1.

Petersen, R. C, Stevenas, J. C., Ganguli, M., Tangalos, E. G., Cummings, J. L., and DeKosky, S. T. Practice parameter: Early detection of dementia: Mild cognitive impairment Neurology 2001 56 1133-1142

Rahil-Khazen R, Bolann B J, Ulvik Rj. Trace element reference values in serum determined by inductively coupled plasma atomic emission spectrometry. Clin Chem Lab Med 2000; 38 (8); 765-72.

Regland B, Lehmann W, Abedini I et al. Treatment of Alzheimer's disease with clioquinol. Dement Geriatr Cogn Disord 2001; 12:408-14

Richard, J. A., Breen, G. F., Crawford, L. P., Grinter, T. J., Harris, M. A., Haynes, J. F., Moores, C. J., Saunders, R. N., Share, A. C., Walsgrove, T. C. and Wicks, C. *Organic Process Research & Development*, 1997, 1, 185.

Rogers S L, Farlow M R, Doody R S, Mohs R, Friedhoff L T. A 24-week, double-blind, placebo-controlled trial of donepezil in patients with Alzheimer's disease. Donepezil Study Group. Neurology 1998; 50:136-45

Rosen W G, Mohs R C, Davis K L. A new rating scale for Alzheimer's disease. Am J Psychiatry 1984; 141:1356-64

Schenk, D., Barbour, R., Dunn, W., Gordon, G., Grajeda, H., Guido, T., Hu, K., Huang, J., Johnson-Wood, K., Khan, K., Kholodenko, D., Lee, M., Liao, Z., Lieberburg, I., Motter, R., Mutter, L., Soriano, F., Shopp, G., Vasquez, N., Vandervert, C., Walker, S., Wogulis, M., Yednock, T., Games, D., and Seubert, P. (1999) Immunization with amyloid-β attenuates Alzheimer's disease like pathology in the PDAPP mouse. Nature 400, 173-177

Selkoe, D. J. Alzheimer's disease: genes, proteins and therapy. Physiol Rev 81 (2): 741-766

Shearman M S, Beher D, Clarke E E et al. L-685,458, an aspartyl protease transition state mimic, is a potent inhibitor of amyloid β-protein precursor β-secretase activity. Biochemistry 2000; 29:8698-704

Shrader, W. D. Celebuski, J. Kline S. J. and Johnson, D. Tetrahedron Lett., 1988, 29, 1351-1354.

Shin, I., Silman, I., Weiner, L. M. (1996) Interaction of partially unfolded forms of Torpedo acetylcholinesterase with liposomes. Protein Sci 5(1):42-51

Shiraki, H. The neuropathology of subacute myelo-opticoneuropathy (SMON) in the humans: With speical reference to the quinoform intoxication. Jpn J Med Sci Biol 1975; 28 (suppl): 101-164

Simons M, Schwiirzler F, Liitjohann D et al. Treatment with simvastatin in normocholesterolemic patients with Alzheimer's disease: a 26-week randomised, placebo-controlled, double-blind trial. Ann of Neurol In Press.

Sinha S, Anderson J P, Barbour R et al. Purification and cloning of amyloid precursor protein β-secretase from human brain. Nature 1999; 402:537-40

St George-Hyslop, P. H. (2000) Molecular genetics of Alzheimer's disease. *Biol. Psychiatry* 47, 183-199

T. C. Wang, Y. L. Chen, K. H. Lee and C. C. Tzeng, *Tetrahedron Lett.*, 1996, 37, 6369-6370.

White et al., J Neuroscience, (1998) 18, 6207-6217

Valdez-Gonzalez, T., Inagawa, J., and Ido, T. (2001) Neuropeptides interact with glycolipid receptors: a surface plasmon resonance study. Peptides 22; 1099-1106.

Wright, J. S. Johnson, E. R. and DiLabio, G. A. *J. Am. Chem. Soc* 2001 123 1173-1183.

Yassin M S, Ekblom J, Xilinas M, Gottfries C G, Oreland L. Changes in uptake of vitamin B(12) and trace metals in brains of mice treated with clioquinol. J Neurol Sci 2000; 173:40-44

What is claimed is:

1. A method for the treatment of Alzheimer's disease in a subject which comprises administering to the subject a therapeutically effective amount of a compound of the formula

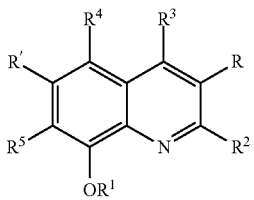

I or pharmaceutically acceptable salts thereof, in which
$R^1$ is H;
$R^2$ is optionally substituted phenyl; optionally substituted naphthyl; optionally substituted tetrahydronaphthyl; optionally substituted biphenyl; optionally substituted heteroaromatic; $CSR^6$; CN; $HCNOR^9$; $HCNNR^9R^{10}$; $OR^{11}$; $SR^{11}$; or $SO_2NR^{13}R^{14}$; in which $R^{13}$ and $R^{14}$ are either the same or different and selected from H, optionally substituted alkyl, optionally substituted alkenyl, optionally substituted aryl or optionally substituted heterocyclyl; and
$R^6$ is H, $C_{1-6}$ alkyl, optionally substituted $C_{2-6}$ alkenyl, hydroxy, optionally substituted aryl, optionally substituted heterocyclyl, $SR^7$ or $NR^7R^8$;
$R^7$ and $R^8$ are either the same or different and selected from H, optionally substituted $C_{1-6}$ alkyl, optionally substituted $C_{2-6}$ alkenyl, optionally substituted aryl and optionally substituted heterocyclyl;

$R^9$ is H, optionally substituted $C_{1-6}$ alkyl, optionally substituted $C_{2-6}$ alkenyl, optionally substituted aryl or optionally substituted heterocyclyl;

$R^{10}$ is hydrogen, methyl, propyl, isopropyl, butyl, isobutyl, sec-butyl, tert-butyl, pentyl, neopentyl, hexyl, cyclopropyl, cyclobutyl, cyclopentyl, cyclohexyl, optionally substituted $C_{2-6}$ alkenyl, optionally substituted aryl or optionally substituted heterocyclyl;

$R^{11}$ is H, optionally substituted $C_{1-6}$ alkyl, optionally substituted $C_{2-6}$ alkenyl, optionally substituted aryl or optionally substituted heterocyclyl;

$R^3$, R and R' are either the same or different and selected from H, optionally substituted $C_{1-6}$ alkyl, optionally substituted $C_{2-6}$ alkenyl, optionally substituted $C_{1-6}$ alkoxy, optionally substituted acyl, hydroxy, optionally substituted amino, optionally substituted thio, optionally substituted sulphonyl, optionally substituted sulphinyl, optionally substituted sulphonylamino, halo, $SO_3H$, amine, CN, $CF_3$, optionally substituted aryl and optionally substituted heterocyclyl; and $R^4$ and $R^5$ are chloro, wherein the optional substituent is $C_{1-6}$ alkyl, $CF_3$, fluorine, chlorine, iodine, cyano, $C_{1-6}$ alkoxy, 5 or 6-membered aryl, heteroaryl, amino or $C_{1-6}$ alkylamino.

2. The method according to claim 1, in which either $R^2$ is optionally substituted phenyl, optionally substituted naphthyl, optionally substituted tetrahydronapthyl, optionally substituted biphenyl, optionally substituted heteroaromatic, or at least one of R, $R^3$ and R' is optionally substituted $C_{1-6}$ alkyl, optionally substituted aryl, optionally substituted heterocyclyl.

3. The method of claim 1, in which the compound of formula I is administered in association with a pharmaceutically acceptable carrier.

4. The method of claim 1, in which the compound of formula I is administered in association with a medicament, said medicament being an inhibitor of the acetyl cholinesterase active site, an antioxidant, an anti-inflammatory agent or an oestrogenic agent.

5. The method of claim 1, in which the compound of formula I is in hydrate form.

6. A method for the treatment of Alzheimer's disease in a subject which comprises administering to the subject a therapeutically effective amount of a compound selected from the group of

PBT 1038

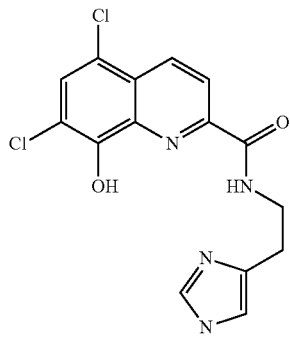

-continued
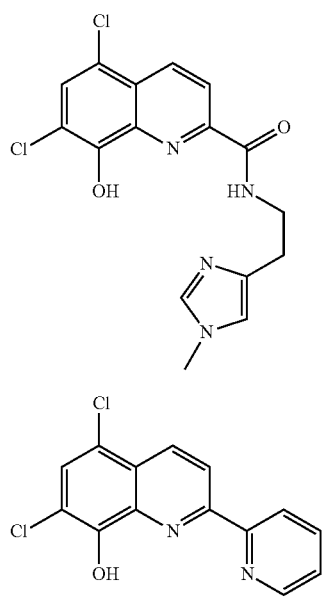
PBT 1050
PBT 1052
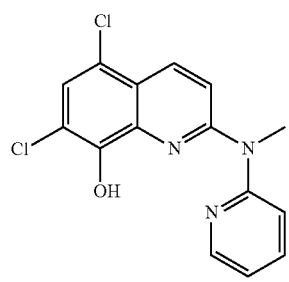
PBT 1056
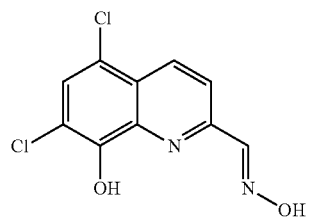
PBT 1031
or pharmaceutically acceptable salts thereof.
* * * * *